United States Patent
Aigner et al.

(10) Patent No.: US 12,012,464 B2
(45) Date of Patent: *Jun. 18, 2024

(54) FACTOR XI ANTIBODIES AND METHODS OF USE

(71) Applicant: NOVARTIS AG, Basel (CH)

(72) Inventors: Maximilian Aigner, Planegg (DE); Alexander Wolfgang Koch, Cambridge, MA (US); Markus Waldhuber, Planegg (DE)

(73) Assignee: NOVARTIS AG, Basel (CH)

( * ) Notice: Subject to any disclaimer, the term of this patent is extended or adjusted under 35 U.S.C. 154(b) by 185 days.

This patent is subject to a terminal disclaimer.

(21) Appl. No.: 17/450,122

(22) Filed: Oct. 6, 2021

(65) Prior Publication Data

US 2022/0162339 A1    May 26, 2022

Related U.S. Application Data

(63) Continuation of application No. 16/472,646, filed as application No. PCT/IB2017/058312 on Dec. 21, 2017, now Pat. No. 11,168,147.

(60) Provisional application No. 62/438,648, filed on Dec. 23, 2016.

(51) Int. Cl.
*C07K 16/36* (2006.01)
*C07K 16/40* (2006.01)

(52) U.S. Cl.
CPC .............. *C07K 16/40* (2013.01); *C07K 16/36* (2013.01); *C07K 2317/21* (2013.01); *C07K 2317/33* (2013.01); *C07K 2317/34* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,439,196 A | 3/1984 | Higuchi |
| 4,447,224 A | 5/1984 | DeCant, Jr. et al. |
| 4,447,233 A | 5/1984 | Mayfield |
| 4,486,194 A | 12/1984 | Ferrara |
| 4,487,603 A | 12/1984 | Harris |
| 4,596,556 A | 6/1986 | Morrow et al. |
| 4,634,665 A | 1/1987 | Axel et al. |
| 4,790,824 A | 12/1988 | Morrow et al. |
| 4,816,397 A | 3/1989 | Boss et al. |
| 4,816,567 A | 3/1989 | Cabilly et al. |
| 4,941,880 A | 7/1990 | Burns |
| 4,946,778 A | 8/1990 | Ladner et al. |
| 4,963,657 A | 10/1990 | Pixley |
| 5,064,413 A | 11/1991 | McKinnon et al. |
| 5,179,017 A | 1/1993 | Axel et al. |
| 5,223,409 A | 6/1993 | Ladner et al. |
| 5,225,539 A | 7/1993 | Winter |
| 5,312,335 A | 5/1994 | McKinnon et al. |
| 5,383,851 A | 1/1995 | McKinnon, Jr. et al. |
| 5,399,163 A | 3/1995 | Peterson et al. |
| 5,403,484 A | 4/1995 | Ladner et al. |
| 5,545,806 A | 8/1996 | Lonberg et al. |
| 5,569,825 A | 10/1996 | Lonberg et al. |
| 5,571,698 A | 11/1996 | Ladner et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,661,806 A | 8/1997 | Lonberg et al. |
| 5,959,083 A | 9/1999 | Bosslet et al. |
| 6,005,091 A | 12/1999 | Blackburn et al. |
| 7,217,794 B2 | 5/2007 | Abdel-Neguid et al. |
| 7,300,922 B2 | 11/2007 | Sullenger et al. |
| 7,459,564 B2 | 12/2008 | Corte et al. |
| 7,501,404 B2 | 3/2009 | Bannister et al. |
| 7,544,699 B2 | 6/2009 | Mjalli et al. |
| 7,626,039 B2 | 12/2009 | Pinto et al. |
| 7,645,799 B2 | 1/2010 | Corte et al. |
| 7,842,708 B2 | 11/2010 | Pinto et al. |
| 8,236,316 B2 * | 8/2012 | Gruber .................. A61P 35/04 530/387.3 |
| 8,268,783 B2 | 9/2012 | Sinha et al. |
| 8,283,330 B2 | 10/2012 | Sullenger et al. |
| 8,324,199 B2 | 12/2012 | Corte et al. |

(Continued)

FOREIGN PATENT DOCUMENTS

| | | |
|---|---|---|
| CN | 1390258 A | 1/2003 |
| EP | 0 125 023 A1 | 11/1984 |

(Continued)

OTHER PUBLICATIONS

US 9,023,796 B2, 05/2015, Lu et al. (withdrawn)
Awad et al., P T. Nov. 2013;38(11):696-701. PMID: 24391389.*
Merlin et al., Front Immunol. Mar. 24, 2020;11:476. doi: 10.3389/fimmu.2020.00476. eCollection 2020. PMID: 32265927.*
Schumacher, William A. et al., "Inhibition of Factor XIa as a New Approach to Anticoagulation," Arterioscler Thromb Vasc Biol. 2010; 30:388-392, DOI:10.1161/ATVBAHA.109.197178.

(Continued)

*Primary Examiner* — Michael Szperka
(74) *Attorney, Agent, or Firm* — Finnegan, Henderson, Farabow, Garrett & Dunner, LLP

(57) ABSTRACT

The present disclosure relates to monoclonal antibodies and antigen binding fragments thereof that bind to human Factor XI and activated Factor XI ("Factor XIa"), and pharmaceutical compositions and methods of treatment comprising the same.

18 Claims, 6 Drawing Sheets

Specification includes a Sequence Listing.

(56) References Cited

U.S. PATENT DOCUMENTS

| | | |
|---|---|---|
| 8,334,372 B2 | 12/2012 | Freier et al. |
| 8,388,959 B2 | 3/2013 | Gruber et al. |
| 8,399,648 B2 | 3/2013 | Gruber et al. |
| 8,455,439 B2 | 6/2013 | Lu et al. |
| 8,455,441 B2 | 6/2013 | Lu et al. |
| 8,568,724 B2 * | 10/2013 | Hack ................. A61P 9/10 424/139.1 |
| 8,586,524 B2 | 11/2013 | Sullenger et al. |
| 8,735,370 B2 | 5/2014 | Freier et al. |
| 8,889,129 B2 | 11/2014 | Lu et al. |
| 8,940,833 B2 | 1/2015 | Schmitt et al. |
| 9,056,106 B2 | 6/2015 | Sinha et al. |
| 9,062,298 B2 | 6/2015 | Lu et al. |
| 9,109,046 B2 | 8/2015 | Sinha et al. |
| 9,125,895 B2 | 9/2015 | Gruber et al. |
| 9,388,401 B2 | 7/2016 | Lu et al. |
| 9,587,233 B2 | 3/2017 | Sinha et al. |
| 9,636,399 B2 | 5/2017 | Gruber et al. |
| 9,637,550 B2 | 5/2017 | Gruber et al. |
| 9,783,614 B2 | 10/2017 | Wilmen et al. |
| 10,053,515 B2 * | 8/2018 | Chen ................. A61P 7/02 |
| 10,221,247 B2 | 3/2019 | Wilmen et al. |
| 10,465,011 B2 * | 11/2019 | Eder ................. C07K 16/36 |
| 10,647,780 B2 | 5/2020 | Ewert et al. |
| 11,168,147 B2 * | 11/2021 | Aigner ................. C07K 16/40 |
| 2003/0083294 A1 | 5/2003 | Sullenger et al. |
| 2004/0180855 A1 | 9/2004 | Schumacher et al. |
| 2005/0037421 A1 | 2/2005 | Honda et al. |
| 2005/0059705 A1 | 3/2005 | Mjalli et al. |
| 2005/0143317 A1 | 6/2005 | Abdel-Megui et al. |
| 2005/0196397 A1 | 9/2005 | Scheiflinger et al. |
| 2006/0088523 A1 | 4/2006 | Andya et al. |
| 2006/0154915 A1 | 7/2006 | Corte et al. |
| 2007/0105832 A1 | 5/2007 | Bannister et al. |
| 2008/0051339 A1 | 2/2008 | Sullenger et al. |
| 2008/0146811 A1 | 6/2008 | Deng et al. |
| 2008/0161373 A1 | 7/2008 | Pinto et al. |
| 2009/0062287 A1 | 3/2009 | Corte et al. |
| 2009/0098119 A1 | 4/2009 | Lu et al. |
| 2010/0022506 A1 | 1/2010 | Pinto et al. |
| 2010/0125052 A1 | 5/2010 | Lu et al. |
| 2010/0137414 A1 | 6/2010 | Freier et al. |
| 2010/0249217 A1 | 9/2010 | Sullenger et al. |
| 2010/0255000 A1 | 10/2010 | Sinha et al. |
| 2010/0331392 A1 | 12/2010 | Monia et al. |
| 2011/0020349 A1 | 1/2011 | Gruber et al. |
| 2011/0021492 A1 | 1/2011 | Corte et al. |
| 2011/0028446 A1 | 2/2011 | Pinto et al. |
| 2011/0159006 A1 | 6/2011 | Hack |
| 2011/0184057 A1 | 7/2011 | Mundy et al. |
| 2012/0083522 A1 | 4/2012 | Monia et al. |
| 2012/0214862 A1 | 8/2012 | Freier et al. |
| 2012/0269788 A1 | 10/2012 | Lu et al. |
| 2013/0129693 A1 | 5/2013 | Sinha et al. |
| 2013/0190384 A1 | 7/2013 | Freier et al. |
| 2013/0274308 A1 | 10/2013 | Freier et al. |
| 2013/0296400 A1 | 11/2013 | Monia et al. |
| 2014/0044773 A1 | 2/2014 | Lu et al. |
| 2014/0079684 A1 | 3/2014 | Lu et al. |
| 2014/0134151 A1 | 5/2014 | Lu et al. |
| 2014/0194600 A1 | 7/2014 | Hack |
| 2014/0275225 A1 | 9/2014 | Sullenger et al. |
| 2014/0275226 A1 | 9/2014 | Sullenger et al. |
| 2015/0025011 A1 | 1/2015 | Sinha et al. |
| 2015/0057228 A1 | 2/2015 | Lu et al. |
| 2015/0099298 A1 | 4/2015 | Wilmen et al. |
| 2015/0343034 A1 | 12/2015 | Pittman et al. |
| 2016/0002617 A1 | 1/2016 | Sinha et al. |
| 2016/0354449 A1 | 12/2016 | Lu et al. |
| 2017/0014492 A1 | 1/2017 | Sinha et al. |
| 2017/0022292 A1 | 1/2017 | Eder et al. |
| 2017/0035798 A1 | 2/2017 | Freier et al. |
| 2017/0355780 A1 | 12/2017 | Chen et al. |
| 2018/0022825 A1 | 1/2018 | Ewert et al. |
| 2018/0112009 A1 | 4/2018 | Wilmen et al. |
| 2018/0118850 A1 | 5/2018 | Hack |
| 2018/0216093 A1 | 8/2018 | Goletz et al. |
| 2018/0355056 A1 | 12/2018 | Eder et al. |
| 2018/0355057 A1 | 12/2018 | Gruber et al. |
| 2018/0362661 A1 | 12/2018 | Chen et al. |
| 2019/0330372 A1 | 10/2019 | Aigner et al. |
| 2020/0115468 A1 | 4/2020 | Eder et al. |
| 2020/0231701 A1 | 7/2020 | Friedman et al. |
| 2020/0308301 A1 | 10/2020 | Ewert et al. |
| 2020/0317816 A1 | 10/2020 | Ewert et al. |
| 2022/0025070 A1 | 1/2022 | Ewert et al. |
| 2022/0162339 A1 | 5/2022 | Aigner et al. |
| 2023/0002507 A1 | 1/2023 | Friedman et al. |

FOREIGN PATENT DOCUMENTS

| | | |
|---|---|---|
| EP | 0 171 496 A2 | 2/1986 |
| EP | 0 173 494 A2 | 3/1986 |
| EP | 0 184 187 A2 | 6/1986 |
| EP | 0 338 841 A1 | 10/1989 |
| EP | 0 517 024 A2 | 12/1992 |
| EP | 2070939 | 6/2009 |
| EP | 2 297 207 B1 | 3/2011 |
| EP | 2364990 A1 | 9/2011 |
| EP | 2915564 | 9/2015 |
| EP | 2453910 | 8/2016 |
| EP | 2414517 | 9/2016 |
| EP | 3078743 | 10/2016 |
| EP | 3121271 | 1/2017 |
| EP | 3 404 045 A1 | 11/2018 |
| JP | S6265693 A | 3/1987 |
| WO | WO 86/01533 | 3/1986 |
| WO | WO 87/02671 | 5/1987 |
| WO | WO 87/04462 | 7/1987 |
| WO | WO 89/01036 | 2/1989 |
| WO | WO 94/29351 | 12/1994 |
| WO | WO 95/017420 A1 | 6/1995 |
| WO | WO 97/26010 A1 | 7/1997 |
| WO | WO 00/042072 | 7/2000 |
| WO | WO 02/064634 A2 | 8/2002 |
| WO | WO 02/100348 A2 | 12/2002 |
| WO | WO 2002/096926 A1 | 12/2002 |
| WO | WO 03/017935 A2 | 3/2003 |
| WO | WO 03/040169 A2 | 5/2003 |
| WO | WO 2004/035607 A2 | 4/2004 |
| WO | WO 2004/043989 A2 | 5/2004 |
| WO | WO 04/089297 A1 | 10/2004 |
| WO | WO 04/103270 A1 | 12/2004 |
| WO | WO 2004/108749 A2 | 12/2004 |
| WO | WO 06/012504 A1 | 2/2006 |
| WO | WO 2006/012504 A2 | 2/2006 |
| WO | WO 2006/040153 A2 | 4/2006 |
| WO | WO 06/076575 A1 | 7/2006 |
| WO | WO 2006/076575 A2 | 7/2006 |
| WO | WO 07/070826 A1 | 6/2007 |
| WO | WO 2009/042962 A2 | 4/2009 |
| WO | WO 2009/061841 A2 | 5/2009 |
| WO | WO 2009/067660 A2 | 5/2009 |
| WO | WO 2009/114677 A1 | 9/2009 |
| WO | WO 2009/141458 A1 | 11/2009 |
| WO | WO 2009/154461 A1 | 12/2009 |
| WO | WO 2010/045509 A2 | 4/2010 |
| WO | WO 2010/056765 A2 | 5/2010 |
| WO | WO 2010/080623 A2 | 7/2010 |
| WO | WO 2010/117729 A1 | 10/2010 |
| WO | WO 2011/008885 A1 | 1/2011 |
| WO | WO 2011/008995 A1 | 1/2011 |
| WO | WO 2012/151575 A2 | 11/2012 |
| WO | WO 2013/167669 A1 | 11/2013 |
| WO | WO 2014/118677 A1 | 8/2014 |
| WO | WO 2016/207858 A1 | 12/2016 |
| WO | WO-2016207858 A1 * | 12/2016 ......... A61K 39/3955 |
| WO | WO 2017/015558 A1 | 1/2017 |
| WO | WO 2017/015619 A1 | 1/2017 |
| WO | WO 2017/021528 A1 | 2/2017 |
| WO | WO 2017/127468 A1 | 7/2017 |
| WO | WO 2017/162791 A1 | 9/2017 |
| WO | WO 2017/203450 A1 | 11/2017 |
| WO | WO 2017/218371 A1 | 12/2017 |

(56) References Cited

FOREIGN PATENT DOCUMENTS

| | | |
|---|---|---|
| WO | WO 2018/053597 A1 | 3/2018 |
| WO | WO 2018/054813 A1 | 3/2018 |
| WO | WO 2018/116255 A1 | 6/2018 |
| WO | WO 2018/116267 A1 | 6/2018 |
| WO | WO 2018/116267 A2 | 6/2018 |
| WO | WO 2018/116267 A3 | 6/2018 |
| WO | WO 2018/134184 A1 | 7/2018 |
| WO | WO 2019/102353 A1 | 5/2019 |
| WO | WO 2020/131935 A1 | 6/2020 |

OTHER PUBLICATIONS

Bagul et al., "Tunnelled catheters for the haemodialysis patient," Eur J Vasc Endovasc Surg. Jan. 2007;33(1):105-12.

Colman, "Effects of Amino Acid Sequence Changes on Antibody-antigen Interations", Research in Immunology 145.1 (1994): 33-36.

International Search Report and Written Opinion of the International Search Authority for International Application No. PCT/IB2018/059143, dated Mar. 27, 2019, 14 pages.

Janeway, "The interaction of the antibody molecule with specifici antigen", Immunobiology: The Immune System in Health and Disease. 5th edition. New York: Garland Sience; 2001 (5 pgs.).

Kaw et al., "Hematology: Issues in the Dialysis Patient: Platelet Dysfunction and End-Stage Renal Disease," Seminars in Dialysis. vol. 19. No. 4. Malden, USA: Blackwell Publishing Inc, 2006.

Lopez et al., "Discrimination of ischemic and hemorrhagic strokes using a multiplexed, mass spectrometry-based assay for serum apolipoproteins coupled to multi-marker ROC algorithm," Proteomics Clin Appl. Apr. 2012;6(3-4):190-200.

Power "Stroke in dialysis and chronic kidney disease," Blood Purif. 2013;36(3-4):179-83.

Schrör "Aspirin and platelets: the antiplatelet action of aspirin and its role in thrombosis treatment and prophylaxis," Semin Thromb Hemost. 1997;23(4):349-56.

Schumacher et al., "Inhibition of Factor XIa as a New Approach to Anticoagulation," Arterioscler Thromb Vasc Biol. 2010; 30:338-392.

Stryer, Biochemistry 4th, WH Freeman, New York. 1995 pp. 18-23.

Tovo et al., "Factor XIa-specific IgG and a reversal agent to probe factor XI function in thrombosis and hemostasis," Sci. Translational Med., Aug. 24, 2016; 353(8), pp. 1-14 DOI: https://doi.org/10.1126/scitranslmed.aaf4331.

Li Zhenyu, "Study on the Development and Function of a Monoclonal Antibody to FVIII-C2 Domain Inhibit FVIII", 2009, China Academic Journal Electronic Publishing House.

Akiyama, Hideki, et al., "Mechanism of Activation of Coagulation factor XI by by Factor XIIa Studied with monoclonal Antibodies", J. Clin. Invest, 78:1631-1637. 1986.

Al-Horani, Rami A. et al., "Designing Allosteric Inhibitors of Factor XIa. Lessons from the Interactions of Sulfated Pentagalloylglucopyranosides", Journal of Medicinal Chemistry, ACS Publications, 2014, 57, pp. 4805-4818.

Al-Horani & Umesh, "Factor XIa inhibitors: A review of the patent literature", Expert opinion on Therapeutic Patents, 26(3):323-345. 2016.

Argade, Malaika D., "Allosteric inhibition of Human Factor XIa: Discovery of Monosulfated Benzofurans as a Class of Promising Inhibitors", Journal of Medicinal Chemistry, ACS Publications, 2014, 57, pp. 3559-3569.

Baglia, F., et al. "A Binding Site for Thrombin in the Apple 1 Domain of Factor XI", The Journal of Biological Chemistry, 1996 271(7):3652-3658.

Berge, Stephen M. et al., "Pharmaceutical Salts", Journal of Pharmaceutical Sciences, 1977, 66(1):1-19.

Bern et al., Treatment of factor XI inhibitor using recombinant factor VIIa, Haemophilia, 11:20-25. 2005.

Buchmueller "The Anti-Factor XIa Antibody BAY 1213790 is a Novel Anticoagulant that Shows Strong Antithrombotic Efficacy without an Increase Risk of Bleeding in Rabbit Model," International Society on Thrombosis and Haemostasis, Jul. 8-13, 2017, Berlin, Germany.

Chin et al., "Isolation of high-affinity, neutralizing anti-idiotype antibodies by phage and ribosome displayfor application in immunogenicity and pharmacokinetic analyses," Journal of Immunological Methods vol. 416, Jan. 2015, pp. 49-58; https://doi.org/10.1016/j.jim.2014.10.013.

David et al., "Factor XIa-specific IgG and a reversal agent to probe factor XI function in thrombosis and hemostasis", Sci. Transl. Med., vol. 8 353ra112 (2016).

De La Cadena, et al., "Naturally Occurring human Antibodies Against Two Distinct Functional Domains in the Heavy Chain of FXI/FXIa", Blood, 72(5):1748-1754. 1988.

Duebel ed "Handbook of Therapeutic Antibodies," (2007) Chapter 6, pp. 119-144, ISBN: 978-3-527-31453-9, XP007913671.

Edwards et al.,, "The Remarkable Flexibility of the Human Antibody Repertoire; Isolation of Over One Thousand Different Antibodies to a Single Protein, BLyS," J. Mol. Biol. (2003) 334, 103-118, available online at www.sciencedirect.com; © 2003 Elsevier Ltd., 15 pgs.

"Efficacy and Safety of MAA868 in Patients with Atrial Fibrillation", ClinicalTrials.gov, U.S. National Library of Medicine [online], https://www.clinicaltrials.gov/ct2/show/NCT033984?term=maa868&rank=1.

Eigenbrot et al., "Structural Insight into How an Anti-Idiotypic Antibody Against D3H44 (Anti-Tissue Factor Antibody) Restores Normal Coagulation," Journal of Molecular Biology, 331(2):433-446. (Aug. 2003).

Emsley, Jonas et al., "Structure and function of factor XI", Blood, vol. 115, No. 13, Apr. 1, 2010, pp. 2569-2577.

Fanger, Peter M. et al., "Bispecific Antibodies", Critical Reviews in Immunology, 1992, 12(3,4):101-124.

Fradera et al., "High-Resolution crystal structures of facrot XIa coagulation factor in complex with nobasic high-affinity synthetic inhibitors", Acta Cryst. F68, 404-408 (2012).

Fujikawa, et al., "Amino Acid Sequence of Human factor XI, a Blood Coagulation Factor with Four Tandem Repeats That Are Highly Homologous with Plasma Prekallikrein", Biochemistry, 25:2417-2424. 1986.

Gailani, David et al., "Model for a factor IX activation complex on blood platelets: dimeric conformation of factor XIa is essential", Blood, 2001, 97(10):3117-3122.

Gailani, D. et al., "A murine model of factor XI deficiency", Blood Coagulation and Fibrinolysis, 1997, vol. 8, pp. 134-144.

Gailani, D. et al., "The Intrinsic pathway of coagulation: a target for treating thromboembolic disease?" Journal of Thrombosis and Haemostasis, 2007, 5:1106-1112.

Goel et al., "Plasticity within the Antigen-Combining Site May Manifest as Molecular Mimicry in the Humoral Immune Response," J Immunol. Dec. 15, 2004;173(12):7358-67. doi: 10.4049/jimmunol. 173.12.7358.

Goldsmith and Silverman, "Inhibitors of plasma thromboplastin antecedent (factor XI): Studies on mechanism of inhibition", J Lab. Clin Med. 106(3):279-285. 1985.

Greinacher et al., "Reversal of Anticoagulants: An Overview of Current Developments," Thrombosis andHaemostasis, 113(5):931-942. (May 2015).

Gruber, Andras et al., "Antithrombotic factor XI antibody inhibition of the intrinsic pathway", Blood, 2001 98(11):42a.

Gruber and Hanon, "Factor XI-dependence of surface- and tissue factor-initiated thrombus propagation in primates", Blood, 102(3):953-955. 2003.

Hack, C.E. et al., "Disruption of the internal thioester bond in the third component of complement (C3) results in the exposure of neodeterminants also present on activation products of C3. An analysis with monoclonal antibodies", Journal of Immunology, 1988, 141:1602-1609.

Halvoet et al., "Measurement of Free, one-Chain Tissue-Type Plasminogen Activator in Human Plasma With an Enzyme-Linked Immunosorbent Assay Based on an Active Site-Specific Murine Monoclonal Antibody", Blood, 69(1):284-289. 1987.

(56) References Cited

OTHER PUBLICATIONS

Holliger, Philipp, et al., "Diabodies: Small bivalent and bispecific antibody fragments", *Proc Natl. Acad. Sci.*, 1993, 90:6444-6448.
https://www.clinicaltrials.gov/ct2/show/NCT03393481?term=maa868&rank=2.
https://www.clinicaltrials.gov/ct2/show/NCT03398434?term=maa868&rank=1.
International Search Report for PCT/IB2017/058312 dated Mar. 13, 2018.
International Search Report and Written Opinion of the International Search Authority received in International Application No. PCT/US2019/066949, dated Apr. 1, 2020, 16 pgs.
Janeway et al., "*Immunobiology: The Immune System in Health and Disease,*" Third Edition, © 1997 by Current Biology Ltd./Garland Publishing Inc., 13 pgs.
Jin et al., "Crystal Structures of the FXIa Catalytic Domain in Complex with Ecotin Mutants Reveal Substrate-like Interactions", Journal of Biological Chemistry, 280(6):4704-4712 (2005).
Jin, Lei et al., "Mutation of surface residues to promote crystallization of activated factor XI as a complex with benzamidine: an essential sep for the iterative structure-based design of factor XI inhibitors", *Acta Cryst.* (2005) D61, pp. 1418-1425.
Kanyavuz et al., "Breaking the Law: Unconventional Strategies for Antibody Diversification," *NatureReviews Immunology*, vol. 19, Jun. 2019, 13 pgs.
Kipriyanov, Sergey M. et al., "Generation and Production of Engineered Antibodies", *Molecular Biotechnology*, 2004, 26:39-60.
Knappik et al., "Fully synthetic human combinatorial antibody libraries (HuCAL) based on modular consensus frameworks and CDRs randomized with trinucleotides," *J Mol Biol.* Feb. 11, 2000;296(1):57-86. doi: 10.1006/jmbi.1999.3444.
Koch, Alexander W., "MAA868, a novel FXI antibody with a unique binding mode, shows durable effects on markers of anticoagulation in humans", *Blood*, 2019, 133(13): 1507-1516.
Kolyadko et al., "Molecular Mechanisms of Thrombosis, Fundamental and Applied Aspects of theContact Activation," 2014, *Biochemistry (Moscow) Supplement Series A: Membrane and Cell Biology* 8, 279-289.
Konings et al., "Ongoing Contact Activation in Patients with Hereditary Angioedema", Plos One, 8(8):1-9. 2013.
Kravtsov et al., "Factor XI contributes to thrombin generation in the absence of factor XII", Blood, 114(2): 452-458. 2009.
Lloyd et al., "Modelling the Human Immune Response: Performance of a 1011 Human Antibody Repertoire Against a Broad Panel of Therapeutically Relevant Antigens," *Protein Engineering, Design, &Selection*, vol. 22, No. 3, pp. 159-168, 2009; © The Arthur 2008, published by Oxford University Press, 9pgs.
Lou et al., "Affinity Maturation by Chain Shuffling and Site Directed Mutagenesis," 2010. pp. 377-379 Antibody Engineering vol. 1, Ch. 25; DOI 10.1007/978-3-642-01144-3_25, Springer-Verlag Berlin Heidelberg 2010, R. Kontermann and S. Duebel (eds.).
Matafonov, A. et al., "Evidence for factor IX-independent roles for factor XIa in blood coagulation", *Journal of Thrombosis and Haemostasis*, 2013, 11:2118-2127.
Mendez, Michael J. et al., "Functional transplant of megabase human immunoglobulin loci recapitulates human antibody response in mice", *Nature Genetics*, 1997, 15:146-156.
Minnema, et al., "Activation of Clotting Factors XI and IX in Patients With Acute Myocardial Infarction", Arterioscler Thromb Vasc Biol, 20:2489-2493. 2000.
Minnema M.C. et al., "Activation of Clotting Factor XI Without Detectable Contact Activation in Experimental Human Endotoxemia", *Blood*, 1998, 92(9):3294-3301.
Minnema et al., "Activation of the contact System of Coagulation Does Not Contribute to the Hemostatic Imbalance in Hypertriglyceridemia", Arterioscler Throm Vasc Biol. 19:2548-2553. 1999.
Minnema et al., "Enhancement of Rabbit Jugular Vein thrombolysis by neutralization of factor XI in Vivo Evidence for a Role of Factor XI as an Anti-fibrinolytic Factor", J. Clin. Invest., 101(1):10-14. 1998.
Mohammed, Bassem M. et al., "An Update on Factor XI Structure and Function", *Thromb Res.*, Jan. 2018; 161:94-105 (32 pages).
Morgan et al., "Acquired Factor XI Inhibitors in Two Patients with Hereditary Factor XI Deficiency", Thromb Haemostas, 51(3):371-375. 1984.
Naito and Fujikawa, "Activation of Human Blood Coagulation Factor XI Independent of Factor XII", The Journal of Biological Chemistry, 266(12):7353-7358. 1991.
Navaneetham et al., "Structural and Mutational Analyses of the Molecular Interactions between the Catalytic Domain of Factor XIa and the Kunitz Protease Inhibitor Domain of Protease Nexin 2", Journal of Biological Chemistry, 280(43):36165-36175 (2005).
Nishikado et al., "Murine Monoclonal Antibodies to Human Factor XI", Thrombosis Research, 42:225-234. 1986.
Ogawa, Taketoshi et al., "Exosite-mediated Substrate Recognition of Factor XI by Factor XIa", *Journal of Biological Chemistry*, 2005, 280(25):23523-23530.
Ohkubo et al., "Characterization of a Panel of Monoclonal Antibodies to Human Coagulation Factor XI and Detection of Factor XI in Hep G2 Cell Conditioned Medium", Thrombosis and Haemostasis, 63(3):4170423. 1990.
Papagrigoriou, Evangelos et al., "Crystal Structure of the factor XI zymogen reveals a pathway for transactivation", *Nature Structural & Molecular Biology*, vol. 13, No. 6, Jun. 2006, pp. 557-558.
PCT International Search Report and Written Opinion for International Application No. PCT/IB2017/053066 dated Sep. 1, 2017, 16 pgs.
PCT International Search Report for International Application No. PCT/IB2017/058345 dated Jun. 19, 2018, 21 pgs.
Peyvandi, Flora et al., "Factor XI deficiency in Iranians: its clinical manifestations in comparison with those of classic hemophilia", *Haemtologica*, 2002, 87(5):512-514.
"Prevention of Thromboembolic Events in Total Knee Replacement Positions", ClinicalTrials.gov, U.S. National Library of Medicine [online], https://www.clinicaltrials.gov/ct2/show/NCT03393481?term=maa868&rank=2.
Puy, Cristina et al., "Activated factor XI increases the procoagulant activity of the extrinsic pathway by inactivating tissue factor pathway inhibitor", *Blood*, 2015, 125(9):1488-1496.
Py Leung et al., "Inhibition of Factor XII-Mediated Activation of Factor XI Provides Protection Against Experimental Acute Ischemic Stroke in Mice", *Translational Stroke Research*, Sep. 2012;3(3):381-9. doi: 10.1007/s12975-012-0186-5.
Reagents, "Suplemmental Methods and Data", (Jan. 13, 2015), URL: http://www.bloodjournal.org/content/bloodjournal/suppl/2015/01/13/blood-2014-10-604587.DC1/blood-2014-10-604587-1.pdf.
Renne, T. et al., "Characterization of the H-kininogen-binding Site on Factor XI", *The Journal of Biological Chemistry*, 2002, 277(7):4892-4899.
Renne, Thomas et al., "Defective thrombus formation in mice lacking coagulation factor XII", *The Journal of Experimental Medicine*, 2005, 202(2):271-281.
Renne et al., "Factor XI deficiency in animal models", Journal of Thrombosis and Haemostasis, 7(Suppl. 1):79-83. 2009.
Rudikoff et al., "Single Amino Acid Substitution Altering Antigen-Binding Specificity," *Proc. Natl. Acad. Sci. USA*, Mar. 1982, 79(6): 1979-1983.
St. Groth, S. Fazekas et al., "Production of Monoclonal Antibodies: Strategy and Tactics", *Journal of Immunological Methods*, 1980, 35:1-21.
Salomon et al., "Prevalence, causes, and characterization of factor XI inhibitors in patients with inherited factor XI deficiency", Blood, 101(12):4783-4788. 2003.
Samuel et al., "Solution structure of the A4 domain of factor XI sheds light on the mechanism of zymogen activation", PNAS, 104(40):15693-15698. 2007.
Scott et al., "Amidolytic Assay of Human Factor Xi in Plasma: Comparison With a coagulant Assay and a new Rapid Radioimmunoassay", Blood, 63(1):42-50. 1984.

(56) References Cited

OTHER PUBLICATIONS

Sela-Culang et al., "The structural Basis of Antibody-Antigen Recognition," 2013, *Frontiers In Immunology* (13 pgs.) doi: 10.3389/fimmu.2013.00302.

Shumacher et al., "Antithrombotic and hemostatic effects of a small molecule factor XIa inhibitor in rats", European Journal of Pharmacology, 570:167-174. 2007.

Sie et al., "An Acquired Antithrombin Autoantibody Directed toward the Catalytic Center of the Enzyme", J. Clin. Invest., 88:290-296. 1991.

Sinha et al., "Functional Characterization of Human Blood Coagulation factor XIa Using Hybridoma Antibodies", The journal of Biological Chemistry, 260(19):10714-10719. 1985.

Sinha, Dipali et al., "Macromolecular Substrate-Binding Exosites on Both the Heavy and Light Chains of Factor XIa Mediate the Formation of the Michaelis Complex Required for Factor IX-Activation", *Biochemistry*, 2007, 46, 9830-9839.

Smeenk, Ruud J. et al., "Is Anticardiolipin Activity a Cross-Reaction of Anti-DNA or a Separate Entity?", *Arthritis and Rheumatism*, 1987, 30(6): 607-617.

Spronk et al., "Monitoring thrombin generation: Is addition of corn trypsin inhibitor needed", Throm Haemost, 101:1156-1162. 2009.

Stern et al., "Acquired Antibody to Factor XI in a Patient with Congenital factor XI Deficiency", J. Clin. Invest., 69:1270-1276. 1982.

Strejan, G.H. et al., "Suppression of Chronic-Relapsing Experimental Allergic Encephalomyelitis in Strain-13 Guinea Pigs by Administration of Liposome-Associated Myelin Basic Protein", *Journal of Neuroimmunology*, 1984, 7:27-41.

Su, Ya-Chi et al., "The Role of Factor XIa (FXIa) Catalytic Domain Exosite Residues in Substrate Catalysis and Inhibition by the Kunitz Protease Inhibitor Domain of Protease Nexin 2", *The Journal of Biological Chemistry*, vol. 286, No. 36, Sep. 9, 2011, pp. 31904-31914.

Sun, Yuehui et al., "Identification of a Factor IX Binding Site on the Third Apple Domain of Activated Factor XI", *The Journal of Biological Chemistry*, 1996, 271(46):29023-29028.

Tait, Jonathan F. et al., "Primary Structure Requirements for the Binding of Human High Molecular Weight Kininogen to Plasma Prekallikrein and Factor XI", *Journal of Biological Chemistry*, 1987, 262(24): 11651-11656.

Takahashi, M. et al., Inhibition of factor XI reduced thrombus formation in rabbit jugular vein under endothelial denudation and/or blood stasis, Thrombosis Research, 2010, 125(5):464-470.

Tans, Guido et al., Studies on the effect of serine protease inhibitors on activated contact factors Application in amidolytic assays for factor $XII_a$, plasma kallikrein and factor $XI_a$, *Eur. J. Biochem*, 164, pp. 637-642 (1987).

Thomas et al., "First Evaluation of the Safety, Pharmacokinetics and Pharmacodynamics of BAY 1213790, a Full Human IgG1 Antibody Targeting Coagulation Factor XIa, in Healthy Young Men," *International Societyon Thrombosis and Haemostasis*, Jul. 8-13, 2017, Berlin, Germany. URL: https://www.postersessiononline.eu/173580348_eu/congresos/ISTH2017/aula/-PB_834_ISTH2017.pdf.

Tornetta et al., "Isolation of Human Anti-Idiotypic Antibodies by Phage Display for Clinical Immune Response Assays," *J Immunol Methods*. Dec. 1, 2007;328(1-2):34-44. doi: 10.1016/j.jim.2007.08.008. Epub Sep. 4, 2007.

Tucker, Erik et al., "Inhibition of Factor XI decreases thrombin production and prevents vascular occlusion in experimental thrombosis in primates", *Blood*, 2007 110(11):1-5.

Tucker et al., "Prevention of vascular graft occlusion and thrombus-associated thrombin generation by inhibition of factor XI", Blood, 113(4):936-944. 2009.

Van Der Graaf, Fedde et al., "Isolation and Functional Characterization of the Active Light Chain of Activated Human Blood Coagulation Factor XI", *The Journal of Biological Chemistry*, 1983, vol. 258, No. 16, pp. 9669-9675.

Van Montfoort and Meijers, "Anticoagulation beyond direct thrombin and factor Xa inhibitors: indications for targeting the intrinsic pathway", Thrombosis and Haemostasis, 110(2):223-232. 2013.

Van Montfoort, "Factor XI as target for antithrombotic therapy", Thesis. 2014.

Van Montfoort, Maurits L. et al., "Two novel inhibitory anti-human factor XI antibodies prevent cessation of blood flow in a murine venous thrombosis model", *Thrombosis and Haemostasis*, 2013, 110:1065-1073.

Wong, Szu et al., "A novel DFP tripeptide motif interacts with the coagulation factor XI apple 2 domain", *Blood*, vol. 127, No. 23, Jun. 9, 2016, pp. 2915-2923.

Wu, Yan et al., "Structural insight into distinct mechanisms of protease inhibition by antibodies", PNAS, Dec. 11, 2017, vol. 104, No. 50, pp. 19784-19789.

Wuillemin et al., "Activation of the Intrinsic Pathway of Coagulation in Children with Meningococcal Septic Shock", Thrombosis and Haemostasis, 74(6):1436-41. 1995.

Wuillemin, et al., "Thrombin-mediated activation of endogenous factor XI in plasma in the presence of physiological glycosaminoglycans occurs only with high concentrations of thrombin", British Journal of Haematology, 92:466-472. 1996.

Yamashita, A. et al., "Factor XI contributes to thrombus propagation on injured neointima of the rabbit iliac artery", *Journal of Thrombosis and Haemostasis*, 2006, 4:1496:1501.

Yang, Mark X. et al., "Crystalline monoclonal antibodies for subcutaneous delivery", *PNAS*, 2003 100(12):6934-6939.

Zhu et al., "FXIa and platelet polyphosphate as therapeutic targets during human blood clotting on collagen/tissue factor surfaces under flow," *Blood* 2015, 126(12): 1494-1502.

Zucker et al., "Induction of an inhibitor antibody to factor XI in a patient with severe inherited factor XI deficiency by Rh immune globulin", Blood, 111(3):1306-1308. 2008.

\* cited by examiner

FACTOR XI ANTIBODIES AND METHODS OF USE

This application is a continuation of application Ser. No. 16/472,646, filed Jun. 21, 2019, which is a 371 of PCT/162017/058312, filed Dec. 21, 2017 and claims the benefit of U.S. Provisional Application No. 62/438,648 filed on Dec. 23, 2016, all of which are hereby incorporated by reference in their entirety, including the Sequence Listing, which was submitted electronically in ASCII format.

SEQUENCE LISTING

The instant application contains a Sequence Listing which has been submitted electronically in ASCII format and is hereby incorporated by reference in its entirety. Said ASCII copy, created on Dec. 18, 2017, is named PAT057548-WO-PCT_SL.txt and is 82,506 bytes in size.

BACKGROUND

Thrombosis refers to thrombus formation inside blood vessels, subsequent to a combination of hereditary and acquired risk factors, known as thrombophilia or hypercoagulable states. Vessel wall damage, stasis, increased platelets reactivity and activation of clotting factors are some of the fundamental features of thrombosis. Thrombosis can occur in both venous and arterial circulation and can result in the development of deep vein thrombosis (DVT), pulmonary embolism, and stroke. If a thrombus occurs in the arterial system, down-stream ischemia can occur, leading to acute coronary syndromes (ACS), ischemic stroke, and acute limb ischemia. Thrombus formation in the venous system typically leads to deep venous thrombosis, pulmonary embolism and chronic thromboembolic pulmonary hypertension. Clots may also form in the left atrial appendage in patients with atrial fibrillation (AF), and dislodged thrombi may result in potentially devastating complications, i.e. thromboembolic stroke and systemic embolism. The currently available antithrombotic medications, including low molecular weight heparin (LMWH), thrombin inhibitors, and Factor Xa (FXa) inhibitors, are all associated with a significant risk of bleeding (Weitz J. I. (2010) Thromb. Haemost. 103, 62). The development of an antithrombotic agent that does not affect hemostasis, and therefore does not result in bleeding complications, would be highly desirable.

Current anticoagulants are either injected or taken orally. The injectable anticoagulant LMWH is widely used and offers an improved therapeutic profile over formerly applied unfractionated heparin. For the past few decades the most commonly used oral anticoagulant has been warfarin. Warfarin has a narrow therapeutic window that requires frequent monitoring of the coagulation status, and shows a variety of drug-drug interactions. More recently, orally available direct FXa and thrombin inhibitors entered the anticoagulant market and are increasingly applied.

LMWHs, FXa inhibitors, and thrombin inhibitors are all efficacious in the prevention of post-operative venous thromboembolic disease, in the treatment of spontaneous DVT and pulmonary embolism, and in the stroke prevention in atrial fibrillation. However, these anticoagulants are also associated with bleeding complications that were generally comparable to those observed with the older drugs warfarin and unfractionated heparin. In the ADVANCE-2 clinical trial, the FXa inhibitor apixaban (Eliquis) was compared to the LMWH enoxaparin in patients after total knee replacement. While acute apixaban therapy was more effective at preventing venous thromboembolic disease than enoxaparin, both agents were associated with a significant risk of bleeding. Clinically relevant bleeding occurred in 4% of patients receiving apixaban and in 5% of patients treated with enoxaparin (Lassen, M. R., et al (2009) N. Engl. J. Med. 361, 594).

In the RE-LY trial, the direct thrombin inhibitor dabigatran (Pradaxa) was compared to warfarin in patients with atrial fibrillation and a risk of stroke (Connolly, S. J., et al. (2009) N. Engl. J. Med. 361, 1139). Chronic dabigatran therapy was associated with a significantly lower risk of stroke or systemic embolism. However, major bleeding complications occurred in 3.1% of patients receiving 150 mg per day of dabigatran and in 3.4% of patients receiving warfarin (p=0.31).

Atrial fibrillation (AF) remains the most common cardiac arrhythmia in clinical practice, accounting for approximately one third of hospitalizations for cardiac dysrhythmias. Currently, it is estimated to affect more than 6 million patients in Europe and approximately 2.3 million in the United States, and this number continues to grow rapidly because of the increasing proportion of the aging population. It is estimated that approximately 5% of the population over the age of 65 years, and 10% of people aged over 80 years, will develop AF, however, the prevalence of AF is increasing beyond what is explained by age alone. AF risk factors such as hypertension, congestive heart failure, left ventricular hypertrophy, coronary artery disease and diabetes mellitus, and obstructive sleep apnea are also on the rise. As such, the number of affected individuals with AF is expected to increase two to three times over the next three decades in western populations. (Kannel and Benjamin (2008) Med Clin North Am. 2008; 92:17-40; Bunch, et al. (2012) J Innovations of Card Rhythm Manag 2012; 3: 855-63).

The principal risk of AF is a four- to five fold increase in embolic stroke. The attributable risk for stroke associated with AF increases steeply with age to 23.5% at ages 80 to 89. AF is associated with a doubling of mortality in both genders (Kannel and Benjamin 2008). AF is also independently associated with cognitive decline and all forms of dementia (Marzona, et al. (2012) CMAJ 2012; 184: 329-36; Geita et al 2013; Bunch et al 2012).

Most patients with AF require life-long anticoagulation therapy to prevent cardioembolic stroke and systemic embolism. The CHA2DS2-VASc risk score is a validated and widely used stratification tool to predict thromboembolic risk in atrial fibrillation patients and to identify patients who should benefit from anticoagulation therapy (LIP 2011; Camm, et al. (2012) Eur Heart J 2012; 33: 2719-2747); the accumulated evidence shows that CHA2DS2-VASc is at least as accurate as or possibly better than, scores such as CHADS2 in identifying patients who develop stroke and thromboembolism and definitively better at identifying 'truly low-risk' patients with AF. It is estimated that 85 to 90% of AF patients will require anticoagulation therapy.

In a meta-analysis comprising 6 trials which evaluated the effect of vitamin K antagonists (VKA) in reducing stroke and systemic embolism, a highly significant risk reduction in stroke incidence (relative risk reduction of 67% for stoke) was observed. All-cause mortality was significantly reduced (26%) by adjusted-dose VKA vs. control (Hart, Pearce, and Aguilar (2007) Ann Intern Med 2007; 146:857-867). An international normalized ratio (INR) target between 2 and 3 was associated with best benefit-risk ratio (Hylek et al (2003) N Engl J Med; 349:1019-1026) and universally adopted by international and national guidelines.

In the recent years new oral anticoagulants (NOAC) also referred to as direct oral anticoagulants (DOAC) have been approved and introduced to clinical practice. These drugs are at least as effective or even better than warfarin for reducing thrombo-embolic disease (Connolly, et al. (2009) N Engl J Med; 361:1139-51; Connolly, et al. (2011) N Engl J Med; 364:806-17; Patel, et al. (2011) N Engl J Med 2011; 365: 883-91). NOAC were also associated with large reductions in the most devastating complications of warfarin namely hemorrhagic stroke and intracranial hemorrhage. Major bleeding events were similar or slightly lower than well conducted warfarin therapy. In addition NOAC are associated with a lower potential for drug-drug interaction than warfarin and could be used without routine monitoring; this is expected to ease their use in everyday medical practice.

Despite recent improvements, bleeding risk continues to be high with the use of anticoagulants. For instance, the annual incidence of major and clinically relevant non major bleeding was 14.9% and the annual incidence of major bleeding events was 3.6% in patients treated with rivaroxaban in the ROCKET study (Patel et al 2011). The annual incidence of major bleeding was >5% in patients at a high risk for bleeding defined as HAS Bled risk score≥3 (Gallego, et al. (2012) Carc Arrhythm Electrophysiol.; 5:312-318). Major bleeding is a particularly relevant clinical outcome; for instance in the ROCKET study, once major bleeding has occurred, all-cause mortality rate was 20.4% in the rivaroxaban group and 26.1% in the warfarin group. Once major bleeding events have occurred stroke and systemic embolism occurred in 4.7% and 5.4% of patients in rivaroxaban and warfarin groups, respectively (Piccini, et al. (2014) Eur Heart J; 35:1873-80). Hospital stay, transfusion of blood products and resources utilization were also severely impacted by the occurrence of major bleeding. Bleeding risk is also a major reason for not receiving anticoagulants in eligible patients. In the Euro Heart Survey on Atrial Fibrillation comprising data from 182 hospitals in 35 countries and 5333 ambulant and hospitalized AF patients, only 67% of eligible patients received oral anticoagulant at discharge (Nieuwlaat, et al (2005) Eur Heart J; 26, 2422-2434).

A high unmet medical need therefore exists for a safer therapy which can reduce AF thromboembolic complications such as stroke, systemic embolism, cognitive decline and mortality with comparable efficacy as existing therapy but with a lower bleeding liability.

SUMMARY

The present disclosure relates to monoclonal antibodies binding to human coagulation Factor XI and XIa (activated Factor XI)(hereinafter, sometimes referred to as "FXI", "FXIa," and similar terms), and pharmaceutical compositions comprising the same and methods of treatment comprising administering the same. The development of an anti-thrombotic agent that is efficacious in the prevention and treatment of thrombosis or thromboembolic disease/disorder (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, systemic embolism) but carries no or only minimal bleeding risk would meet a sizable unmet medical need. Also provided herein are methods of managing bleeding or bleeding risk in patients treated with, or administered, an anti-FXI antibody described herein.

In specific aspects, antibodies (e.g., human, chimeric, humanized monoclonal antibodies) provided herein bind with similarly high affinity to the catalytic domain (CD) of human FXIa and FXI and induces an inactive protease domain conformation in FXIa.

The isolated anti-FXI and/or anti-FXIa antibodies described herein, e.g., the full IgGs described herein with two binding sites, bind FXI and/or FXIa with an equilibrium dissociation constant ($K_D$) of less than or equal to 100 μM. For example, the isolated antibodies described herein may bind to human FXI and/or FXIa with a $K_D$ of less than or equal to 100 μM, less than or equal to 50 μM, less than or equal to 45 μM, less than or equal to 40 μM, less than or equal to 35 μM, less than or equal to 20 μM, or less than or equal to 10 μM. More specifically, the isolated antibodies described herein may also bind human FXI and/or FXIa with a $K_D$ of less than or equal to 0.2 μM, as measured by solution equilibrium titration assay (SET) for AM4.

The isolated anti-FXI and/or FXIa antibodies and antigen binding fragments described herein can be used to inhibit the direct or indirect activation of Factor IX (also known as FIX), Factor X (FX), and/or thrombin, and/or the binding to platelet receptors, and thereby can prevent activation of the intrinsic and/or common coagulation pathways.

The isolated anti-FXI and/or FXIa antibodies and antigen binding fragments described herein can be used to inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 10 nM, or less than or equal to 5.2 nM. More specifically, an isolated antibody or antigen binding fragments thereof as described herein can inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 20 nM, or less than or equal to 18 nM. More specifically, an isolated antibody or antigen binding fragments thereof as described herein can inhibit the direct or indirect activation of Factor IX (also known as FIX), Factor X (FX), and/or thrombin with an $IC_{50}$ of less than or equal to 100 nM, less than or equal to 50 nM, less than or equal to 35 nM, less than or equal to 25 nM, less than or equal to 10 nM, or less than or equal to 5 nM. In a specific embodiment, an anti-FXI antibody described herein, or antigen binding fragment thereof, inhibits FXIa-mediated activation of its native substrate FIX with an $IC_{50}$ of less than or equal to 2 nM, e.g., 1.8 nM.

The isolated anti-FXI and/or anti-FXIa antibodies, or antigen binding fragments thereof, may be used to inhibit (e.g., block the activation of) the intrinsic and/or common coagulation pathways, e.g., via inhibiting FXI and/or FXIa-mediated activation of FIX. The isolated anti-FXIa antibodies, or antigen binding fragments thereof, may therefore be used to prevent clotting or the propogation of clotting. The isolated antibodies, or antigen binding fragments thereof, may be used to prevent, treat, or ameliorate such coagulation disorders as deep vein thrombosis and stroke (e.g., ischemic stroke) by inhibiting FXI-mediated activation of FIX.

In specific embodiments, anti-FXI and/or anti-FXIa antibodies, or antigen binding fragments thereof, are capable of prolonging the clotting time (e.g., time until a blood clot starts to form) of human plasma in a concentration-dependent manner as determined by the aPTT assay, for example as described in the Examples Section. In a specific embodiment, clotting time (aPTT) was doubled compared to baseline at a total anti-FXI antibody (e.g., antibody AM1, AM2, AM3, or AM4) concentration in the range of 10 nM to 20 nM, for example approximately 11 nM, 13 nM or 14 nM (for example, as described in Example 5), as determined by an aPTT assay. In particular embodiments, anti-FXI and/or anti-FXIa antibodies, or antigen binding fragments thereof, are capable of prolonging the clotting time of human plasma in a concentration-dependent manner with an IC50 in the range of 5 nM to 20 nM, for example approximately 13 nM, as determined by the aPTT assay, for example as described in the Examples Section.

In specific aspects, anti-FXI and/or anti-FXIa antibodies, or antigen binding fragments thereof, described herein is capable of reducing the amount of thrombin, in a concentration-dependent manner, in a thrombin generation assay (TGA) in human plasma, which measures the effect of FXIa inhibition on the thrombing→FXIa feed-forward loop in the presence of very low tissue factor (TF) concentrations. In particular embodiments, anti-FXI and/or anti-FXIa antibodies, or antigen binding fragments thereof, described herein is capable of reducing the amount of thrombin in a thrombin generation assay (TGA) in human plasma with an $IC_{50}$ value in the range of 5 nM to 10 nM, for example approximately 5 nM, 6 nM or 9 nM, and a residual thrombin concentration of approximately 85 nM to 185 nM, for example as described in the Examples Section.

In specific aspects, provided herein are antibodies (e.g., antibodies in Table 2 such as AM1, AM2, AM3, or AM4 or antibodies comprising the HCDRs 1-3 and LCDRs 1-3 of antibody AM1, AM2, AM3, or AM4), or antigen binding fragments thereof, which specifically binds to the catalytic domain of human FXI and/or FXIa.

The isolated anti-FXI and/or FXIa antibodies, or antigen binding fragments thereof, as described herein can be monoclonal antibodies, human or humanized antibodies, chimeric antibodies, single chain antibodies, Fab fragments, Fv fragments, F(ab')2 fragments, or scFv fragments, and/or IgG isotypes (e.g., IgG1 such as human IgG1). In specific embodiments, anti-FXI and/or anti-FXIa antibodies described herein are recombinant human antibodies. In specific embodiments, anti-FXI and/or anti-FXIa antibodies described herein are human IgG1/lambda (λ) antibodies. In specific embodiments, anti-FXI and/or anti-FXIa antibodies described herein are human IgG1/lambda (λ) antibodies comprising an Fc domain engineered to reduce the potential for effector function (e.g., ADCC and/or CDC), for example a human Fc domain comprising D265A and/or P329A substitutions.

The isolated anti-FXI and/or FXIa antibodies, or antigen binding fragments thereof, as described herein can also include a framework in which an amino acid has been substituted into the antibody framework from the respective human VH or VL germline sequences.

Another aspect of the present disclosure includes an isolated antibody or antigen binding fragments thereof having the full heavy and light chain sequences of Fabs described in Table 2. In a particular aspect, the isolated antibody or antigen binding fragments thereof described in Table 2 does not comprise the heavy and light chain sequences of an antibody described in Table 1, e.g., antibody NOV1401. More specifically, the isolated antibody or antigen binding fragment thereof can comprise the heavy and light chain sequences of antibody AM1, AM2, AM3, or AM4.

In a further aspect provided herein is an isolated antibody or antigen binding fragments thereof comprising the heavy and light chain variable domain sequences of antibodies/Fabs described in Table 2. In a particular aspect, the isolated antibody or antigen binding fragments thereof described in Table 2 does not comprise the heavy chain variable domain and light chain variable domain sequences of an antibody described in Table 1, e.g., antibody NOV1401. More specifically, the isolated antibody or antigen binding fragment thereof can comprise the heavy and light chain variable domain sequences of antibody AM1, AM2, AM3, or AM4.

A further aspect provided herein includes an isolated antibody or antigen binding fragments thereof comprising the heavy chain variable domain CDR (i.e., HCDR1, HCDR2, and HCDR3) and light chain variable domain CDR (i.e., LCDR1, LCDR2, and LCDR3) sequences of antibodies described in Table 2, such as Kabat CDRs, IMGT CDRs, Chothia CDRs, or combined CDRs. More specifically, the isolated antibody or antigen binding fragment thereof can comprise the HCDR1, HCDR2, HCDR3, LCDR1, LCDR2, and LCDR3 sequences of antibody AM1, AM2, AM3, or AM4, for example as presented in Table 2, such as Kabat CDRs, IMGT CDRs, Chothia CDRs, or combined CDRs.

The present disclosure also relates to an isolated nucleic acid comprising a sequence encoding a VL polypeptide and/or a VH polypeptide for antibodies and fragments thereof described herein, for example, described in Table 2, such as antibody AM1, AM2, AM3, and AM4. The present disclosure also relates to an isolated nucleic acid comprising a sequence encoding a light chain polypeptide and/or a heavy chain polypeptide for antibodies and fragments thereof described herein, for example, described in Table 2, such as antibody AM1, AM2, AM3, and AM4.

The present disclosure relates to a vector that includes one or more of the nucleic acid molecules described herein. In particular aspects, provided herein is a population of vectors which comprise nucleic acid sequences encoding a VL polypeptide and a VH polypeptide for antibodies and fragments thereof described herein, for example, described in Table 2, such as antibody AM1, AM2, AM3, and AM4. In particular aspects, provided herein is a population of vectors which comprise nucleic acid sequences encoding a light chain polypeptide and a heavy chain polypeptide for antibodies and fragments thereof described herein, for example, described in Table 2, such as antibody AM1, AM2, AM3, and AM4.

The present disclosure also relates to an isolated host cell that includes a recombinant DNA sequence encoding a heavy chain of the antibody described herein, and a second recombinant DNA sequence encoding a light chain of the antibody described herein, wherein said DNA sequences are operably linked to a promoter and are capable of being expressed in the host cell. It is contemplated that the antibody can be a human monoclonal antibody. It is also contemplated that the host cell is a non-human mammalian cell.

The present disclosure also relates to an isolated host cell that includes a recombinant DNA sequence encoding a VH of the antibody described herein, and a second recombinant DNA sequence encoding a VL of the antibody described herein, wherein said DNA sequences are operably linked to a promoter and are capable of being expressed in the host cell. It is contemplated that the antibody can be a human monoclonal antibody. In one embodiment, it is also contemplated that the host cell is a non-human mammalian cell.

The present disclosure also relates to a method of reducing FXI and/or FXIa expression, and/or intrinsic and/or common coagulation pathway activation, wherein the method includes the step of contacting a cell with an effective amount of a composition comprising the isolated antibody or antigen binding fragments thereof described herein.

The present disclosure also relates to a method of inhibiting the binding of FXI and/or FXIa to FIX, wherein the method includes the step of contacting a cell with an effective amount of a composition comprising the isolated antibody or antigen binding fragments thereof described herein.

In one aspect, it is contemplated that the cell is a human cell. It is further contemplated that the cell is in a subject. In one embodiment, it is contemplated that the cell is a platelet. In a particular embodiment, it is further contemplated that the subject is human.

The present disclosure also relates to a method of treating, improving, or preventing a thromboembolic disease or condition in a subject, wherein the method includes the step of administering to the subject an effective amount of a composition comprising the antibody or antigen binding fragments thereof described herein (e.g., antibody AM1, AM2, AM3, or AM4). In one aspect, the thromboembolic disease is a thrombotic disorder (e.g., thrombosis, thrombic stroke, atrial fibrillation, stroke prevention in atrial fibrillation (SPAF), deep vein thrombosis, venous thromboembolism, and pulmonary embolism). In specific embodiments, it is contemplated that the subject is human.

In particular aspects, any of the foregoing isolated antibodies or antigen binding fragments thereof may be a monoclonal antibody or antigen binding fragments thereof.

Non-limiting embodiments of the present disclosure are described in the following aspects:

1. An isolated anti-FXI antibody or antigen-binding fragment thereof that binds within the catalytic domain of FXI and/or FXIa comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein
    the HCDR1 comprises an amino acid sequence selected from the group consisting of SEQ ID NOs: 3, 6, 7, and 9;
    the HCDR2 comprises an amino acid sequence selected from the group consisting of:
    (i) X1-I-X2-X3-X4-X5-X6-X7-T-X8-YADSVKG (SEQ ID NO: 59), wherein X1 is any amino acid or is T or S, X2 is any amino acid or is D or E, X3 is any amino acid or is Y or S, X4 is any amino acid or is S, Y, or W, X5 is any amino acid or is S, D, or G, X6 is any amino acid or is Q, T, or D, X7 is any amino acid or is D or E, and X8 is any amino acid or is Y, H or D, wherein HCDR2 is not SEQ ID NO: 4,
    (ii) X1-X2-X3-X4-X5-X6 (SEQ ID NO: 60), wherein X1 is any amino acid or is E or D, X2 is any amino acid or is Y or S, X3 is any amino acid or is Y, S or W, X4 is any amino acid or is S, D, or G, X5 is any amino acid or is D, T, or Q, and X6 is any amino acid or is D or E, wherein HCDR2 is not SEQ ID NO: 8, and
    (iii) I-X1-X2-X3-X4-X5-X6-T (SEQ ID NO: 61), wherein X1 is any amino acid or is E or D, X2 is any amino acid or is Y or S, X3 is any amino acid or is S, Y, or W, X4 is any amino acid or is S, D, or G, X5 is any amino acid or is D, T, or Q, and X6 is any amino acid or is D or E, wherein HCDR2 is not SEQ ID NO: 10;
    the HCDR3 comprises an amino acid sequence selected from the group consisting of SEQ ID NOs: 5 and 11;
    the LCDR1 comprises an amino acid sequence selected from the group consisting of SEQ ID NOs: 16, 19, and 22;
    the LCDR2 comprises an amino acid sequence selected from the group consisting of SEQ ID NOs: 17 and 20; and
    the LCDR3 comprises an amino acid sequence selected from the group consisting of SEQ ID NOs: 18 and 21.

2. The antibody or antigen-binding fragment of aspect 1, wherein
    (i) the HCDR1 comprises the amino acid sequence of SEQ ID NO: 3;
    (ii) the HCDR2 comprises the amino acid sequence X1-I-X2-X3-X4-X5-X6-X7-T-X8-YADSVKG (SEQ ID NO: 59), wherein X1 is any amino acid or is T or S, X2 is any amino acid or is D or E, X3 is any amino acid or is Y or S, X4 is any amino acid or is S, Y, or W, X5 is any amino acid or is S, D, or G, X6 is any amino acid or is Q, T, or D, X7 is any amino acid or is D or E, and X8 is any amino acid or is Y, H or D, and wherein HCDR2 is not SEQ ID NO: 4;
    (iii) the HCDR3 comprises the amino acid sequence of SEQ ID NO: 5;
    (iv) the LCDR1 comprises the amino acid sequence of SEQ ID NO: 16;
    (v) the LCDR2 comprises the amino acid sequence of SEQ ID NO: 17; and
    (vi) the LCDR3 comprises the amino acid sequence of SEQ ID NO: 18.

3. The antibody or antigen-binding fragment of aspect 1, wherein
    (i) the HCDR1 comprises the amino acid sequence of SEQ ID NO: 6;
    (ii) the HCDR2 comprises the amino acid sequence X1-I-X2-X3-X4-X5-X6-X7-T-X8-YADSVKG (SEQ ID NO: 59), wherein X1 is any amino acid or is T or S, X2 is any amino acid or is D or E, X3 is any amino acid or is Y or S, X4 is any amino acid or is S, Y, or W, X5 is any amino acid or is S, D, or G, X6 is any amino acid or is Q, T, or D, X7 is any amino acid or is D or E, and X8 is any amino acid or is Y, H or D, and wherein HCDR2 is not SEQ ID NO: 4;
    (iii) the HCDR3 comprises the amino acid sequence of SEQ ID NO: 5;
    (iv) the LCDR1 comprises the amino acid sequence of SEQ ID NO: 16;
    (v) the LCDR2 comprises the amino acid sequence of SEQ ID NO: 17; and
    (vi) the LCDR3 comprises the amino acid sequence of SEQ ID NO: 18.

4. The antibody or antigen-binding fragment of aspect 1, wherein
    (i) the HCDR1 comprises the amino acid sequence of SEQ ID NO: 7;

(ii) the HCDR2 comprises the amino acid sequence X1-X2-X3-X4-X5-X6 (SEQ ID NO: 60), wherein X1 is any amino acid or is E or D, X2 is any amino acid or is Y or S, X3 is any amino acid or is Y, S or W, X4 is any amino acid or is S, D, or G, X5 is any amino acid or is D, T, or Q, and X6 is any amino acid or is D or E, and wherein HCDR2 is not SEQ ID NO: 8;
(iii) the HCDR3 comprises the amino acid sequence of SEQ ID NO: 5;
(iv) the LCDR1 comprises the amino acid sequence of SEQ ID NO: 19;
(v) the LCDR2 comprises the amino acid sequence of SEQ ID NO: 20; and
(vi) the LCDR3 comprises the amino acid sequence of SEQ ID NO: 21.

5. The antibody or antigen-binding fragment of aspect 1, wherein
(i) the HCDR1 comprises the amino acid sequence of SEQ ID NO: 9;
(ii) the HCDR2 comprises the amino acid sequence I-X1-X2-X3-X4-X5-X6-T of (SEQ ID NO: 61), wherein X1 is any amino acid or is E or D, X2 is any amino acid or is Y or S, X3 is any amino acid or is S, Y, or W, X4 is any amino acid or is S, D, or G, X5 is any amino acid or is D, T, or Q, and X6 is any amino acid or is D or E, and wherein HCDR2 is not SEQ ID NO: 10;
(iii) the HCDR3 comprises the amino acid sequence of SEQ ID NO: 11;
(iv) the LCDR1 comprises the amino acid sequence of SEQ ID NO: 22;
(v) the LCDR2 comprises the amino acid sequence of SEQ ID NO: 20; and
(vi) the LCDR3 comprises the amino acid sequence of SEQ ID NO: 18.

6. An isolated anti-FXI antibody or antigen-binding fragment thereof that binds within the catalytic domain of FXI and/or FXIa comprising (i) a heavy chain variable region (VH) comprising complementarity determining regions HCDR1, HCDR2, and HCDR3, and (ii) a light chain variable region (VL) comprising complementarity determining regions LCDR1, LCDR2, and LCDR3, wherein
the HCDR1 comprises an amino acid sequence selected from the group consisting of SEQ ID NOs: 3, 6, 7, and 9;
the HCDR2 comprises an amino acid sequence selected from the group consisting of SEQ ID NOs: 27, 28, 29, 38, 39, 40, 45, 46, and 47;
the HCDR3 comprises an amino acid sequence selected from the group consisting of SEQ ID NOs: 5 and 11;
the LCDR1 comprises an amino acid sequence selected from the group consisting of SEQ ID NOs: 16, 19, and 22;
the LCDR2 comprises an amino acid sequence selected from the group consisting of SEQ ID NOs: 17 and 20; and
the LCDR3 comprises an amino acid sequence selected from the group consisting of SEQ ID NOs: 18 and 21.

7. The antibody or antigen-binding fragment of aspect 6, wherein
(i) the HCDR1 comprises the amino acid sequence of SEQ ID NO: 3, the HCDR2 comprises the amino acid sequence of SEQ ID NO: 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
(ii) the HCDR1 comprises the amino acid sequence of SEQ ID NO: 6, the HCDR2 comprises the amino acid sequence of SEQ ID NO: 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
(iii) the HCDR1 comprises the amino acid sequence of SEQ ID NO: 7, the HCDR2 comprises the amino acid sequence of SEQ ID NO: 46, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21; or (iv) the HCDR1 comprises the amino acid sequence of SEQ ID NO: 9, the HCDR2 comprises the amino acid sequence of SEQ ID NO: 47, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

8. The antibody or antigen-binding fragment of aspect 6, wherein
(i) the HCDR1 comprises the amino acid sequence of SEQ ID NO: 3, the HCDR2 comprises the amino acid sequence of SEQ ID NO: 38, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
(ii) the HCDR1 comprises the amino acid sequence of SEQ ID NO: 6, the HCDR2 comprises the amino acid sequence of SEQ ID NO: 38, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
(iii) the HCDR1 comprises the amino acid sequence of SEQ ID NO: 7, the HCDR2 comprises the amino acid sequence of SEQ ID NO: 39, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21; or
(iv) the HCDR1 comprises the amino acid sequence of SEQ ID NO: 9, the HCDR2 comprises the amino acid sequence of SEQ ID NO: 40, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

9. The antibody or antigen-binding fragment of aspect 6, wherein
   (i) the HCDR1 comprises the amino acid sequence of SEQ ID NO: 3, the HCDR2 comprises the amino acid sequence of SEQ ID NO: 27, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
   (ii) the HCDR1 comprises the amino acid sequence of SEQ ID NO: 6, the HCDR2 comprises the amino acid sequence of SEQ ID NO: 27, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
   (iii) the HCDR1 comprises the amino acid sequence of SEQ ID NO: 7, the HCDR2 comprises the amino acid sequence of SEQ ID NO: 28, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21; or
   (iv) the HCDR1 comprises the amino acid sequence of SEQ ID NO: 9, the HCDR2 comprises the amino acid sequence of SEQ ID NO: 29, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

10. The antibody or antigen-binding fragment of aspect 6, wherein the HCDR1 comprises the amino acid sequence of SEQ ID NO: 3, the HCDR2 comprises the amino acid sequence of SEQ ID NO: 27, 38, or 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18.

11. The antibody or antigen-binding fragment of aspect 6, wherein the HCDR1 comprises the amino acid sequence of SEQ ID NO: 6, the HCDR2 comprises the amino acid sequence of SEQ ID NO: 27, 38, or 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18.

12. The antibody or antigen-binding fragment of aspect 6, wherein the HCDR1 comprises the amino acid sequence of SEQ ID NO: 7, the HCDR2 comprises the amino acid sequence of SEQ ID NO: 28, 39, or 46, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21.

13. The antibody or antigen-binding fragment of aspect 6, wherein the HCDR1 comprises the amino acid sequence of SEQ ID NO: 9, the HCDR2 comprises the amino acid sequence of SEQ ID NO: 29, 40, or 47, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

14. An isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 selected from Table 2, and wherein the VL comprises complementarity determining regions LCDR1, LCDR2, and LCDR3 selected from Table 2.

15. The antibody or antigen-binding fragment of aspect 14, wherein the VH comprises Combined HCDR1, HCDR2, and HCDR3 and the VL comprises Combined LCDR1, LCDR2, and LCDR3.

16. The antibody or antigen-binding fragment of aspect 14, wherein the VH comprises Kabat HCDR1, HCDR2, and HCDR3 and the VL comprises Kabat LCDR1, LCDR2, and LCDR3.

17. The antibody or antigen-binding fragment of aspect 14, wherein the VH comprises Chothia HCDR1, HCDR2, and HCDR3 and the VL comprises Chothia LCDR1, LCDR2, and LCDR3.

18. The antibody or antigen-binding fragment of aspect 14, wherein the VH comprises IMGT HCDR1, HCDR2, and HCDR3 and the VL comprises IMGT LCDR1, LCDR2, and LCDR3.

19. An isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 of antibody AM1, and wherein the VL comprises complementarity determining regions LCDR1, LCDR2, and LCDR3 of antibody AM1.

20. An isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 of antibody AM2, and wherein the VL comprises complementarity determining regions LCDR1, LCDR2, and LCDR3 of antibody AM2.

21. An isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 of antibody AM3 or AM4, and wherein the VL comprises complementarity determining regions LCDR1, LCDR2, and LCDR3 of antibody AM3 or AM4.

22. The antibody or antigen-binding fragment of aspect 6, wherein the VH comprises the amino acid sequence of SEQ ID NOs: 30, 41, and 48; and the VL comprises the amino acid sequence of SEQ ID NO: 34 or 55.

23. The antibody or antigen-binding fragment of aspect 22, wherein the VH comprises the amino acid sequence of SEQ ID NO: 48 and the VL comprises the amino acid sequence of SEQ ID NO: 55.

24. The antibody or antigen-binding fragment of aspect 22, wherein the VH comprises the amino acid sequence of SEQ ID NO: 48 and the VL comprises the amino acid sequence of SEQ ID NO: 34.

25. The antibody or antigen-binding fragment of aspect 22, wherein the VH comprises the amino acid sequence of SEQ ID NO: 41 and the VL comprises the amino acid sequence of SEQ ID NO: 34.

26. The antibody or antigen-binding fragment of aspect 22, wherein the VH comprises the amino acid sequence of SEQ ID NO: 30 and the VL comprises the amino acid sequence of SEQ ID NO: 34.

27. The antibody or antigen-binding fragment of aspect 6, wherein the heavy chain comprises the amino acid sequence of SEQ ID NOs: 32, 43, 50, or 53; and the light chain comprises the amino acid sequence of SEQ ID NO: 57 or 36.

28. The antibody or antigen-binding fragment of aspect 22, wherein the heavy chain comprises the amino acid sequence of SEQ ID NO: 53 and the light chain comprises the amino acid sequence of SEQ ID NO: 57.

29. The antibody or antigen-binding fragment of aspect 22, wherein the heavy chain comprises the amino acid sequence of SEQ ID NO: 50 and the light chain comprises the amino acid sequence of SEQ ID NO: 36.

30. The antibody or antigen-binding fragment of aspect 22, wherein the heavy chain comprises the amino acid sequence of SEQ ID NO: 43 and the light chain comprises the amino acid sequence of SEQ ID NO: 36.

31. The antibody or antigen-binding fragment of aspect 22, wherein the heavy chain comprises the amino acid sequence of SEQ ID NO: 32 and the light chain comprises the amino acid sequence of SEQ ID NO: 36.

32. The antibody or antigen-binding fragment of aspect 6, wherein the VH comprises an amino acid sequence that is at least 90% identical to amino acid sequence of SEQ ID NOs: 30, 41, and 48; the VL comprises an amino acid sequence that is at least 90% to the amino acid sequence of SEQ ID NO: 34 or 55, and wherein the VH does not comprise the amino acid sequence of SEQ ID NO: 12 and the VL does not comprise the amino acid sequence of SEQ ID NO: 23.

33. The antibody or antigen-binding fragment of aspect 6, wherein the VH comprises an amino acid sequence that is at least 95% identical to amino acid sequence of SEQ ID NOs: 30, 41, and 48; the VL comprises an amino acid sequence that is at least 95% to the amino acid sequence of SEQ ID NO: 34 or 55, and wherein the VH does not comprise the amino acid sequence of SEQ ID NO: 12 and the VL does not comprise the amino acid sequence of SEQ ID NO: 23.

34. The antibody or antigen-binding fragment of any one of aspects 1-33, which is a monoclonal human antibody.

35. The antibody or antigen-binding fragment of any one of aspects 1-33, which is a monoclonal humanized antibody.

36. The antibody or antigen-binding fragment of any one of aspects 1-35, which is a human IgG1 isotype antibody.

37. The antibody or antigen-binding fragment of any one of aspects 1-35, which is a human IgG2 or IgG4 isotype antibody.

38. The antibody or antigen-binding fragment of any one of aspects 1-33, which is a single chain antibody, a Fab fragment, a Fv fragment, a F(ab')2 fragment, or a scFv fragment.

39. A pharmaceutical composition comprising an antibody or antigen-binding fragment thereof of any one of aspects 1-38 and a pharmaceutically acceptable carrier.

40. A method of treating or managing or reducing the risk of a thromboembolic disorder comprising administering to a subject in need thereof an effective amount of a pharmaceutical composition comprising an antibody or antigen-binding fragment according to any one of aspects 1-38.

41. The method of aspect 40, wherein the subject is afflicated with, or is at risk of developing, one or more of stroke associated with atrial fibrillation and deep vein thrombosis.

42. The method of aspect 40, wherein the subject is afflicated with, or at risk of developing, stroke associated with atrial fibrillation.

43. The method of aspect 40, wherein the subject is afflicted with atrial fibrillation.

44. A method of preventing, treating or managing or reducing the risk of stroke comprising administering to a subject in need thereof, an effective amount of a pharmaceutical composition comprising an antibody or antigen-binding fragment according to any one of aspects 1-38.

45. The method of aspect 44, wherein the subject is afflicted with atrial fibrillation.

46. A method of treating or managing or reducing the risk of a thromboembolic disorder comprising administering to a subject in need thereof an effective amount of a pharmaceutical composition comprising an antibody or fragment according to any one of aspects 1-38 in combination with one or more statin therapies.

47. A method of managing or reducing bleeding or bleeding risk in a subject treated or administered an anti-FXI antibody or antigen-binding fragment of any one of aspects 1-38, comprising the step of administering to the subject in need thereof, an anti-idiotype antibody or fragment thereof that specifically binds to the anti-FXI antibody and blocks the anti-FXI antibody from binding to FXI, and wherein the anti-idiotype antibody or fragment thereof reverses the anti-coagulant activity of the anti-FXI antibody.

48. The method of aspect 47, wherein the anti-idiotype antibody or fragment thereof is administered to the subject once or twice to temporarily reverse the anti-coagulant effect of the anti-FXI antibody.

49. A method of managing or reducing bleeding or bleeding risk in a subject treated or administered an anti-FXI antibody or antigen-binding fragment of any one of aspects 1-38, said method comprises temporarily reversing of the anticoagulant effect for a sufficient time to manage the bleeding by one of the following: (i) fluid replacement using colloids, crystalloids, human plasma or plasma proteins such as albumin; (ii) transfusion with packed red blood or whole blood; or (iii) administration of fresh frozen plasma (FFP), prothrombin complex concentrates (PCC), activated PCC (APCC), such as, factor VIII inhibitor, and/or recombinant activated factor VII.

50. The method of any one of aspects 40-46, comprising administering to the subject one, two, three, four or five doses of an anti-idiotype antibody or fragment thereof that specifically binds to the anti-FXI antibody and blocks the anti-FXI antibody from binding to FXI, and wherein the anti-idiotype antibody or fragment thereof reverses the anti-coagulant activity of the anti-FXI antibody.
51. The method of any one of aspects 40-46, comprising temporarily reversing of the anticoagulant effect for a sufficient time to manage the bleeding by one of the following: (i) fluid replacement using colloids, crystalloids, human plasma or plasma proteins such as albumin; (ii) transfusion with packed red blood or whole blood; or (iii) administration of fresh frozen plasma (FFP), prothrombin complex concentrates (PCC), activated PCC (APCC), such as, factor VIII inhibitor, and/or recombinant activated factor VII.
52. A method for reversing the anticoagulant effect of an anti-FXI antibody or antigen-binding fragment of any one of aspects 1-38 in a patient being treated with the anti-FXI/FXIa antibody or antigen-binding fragment thereof, comprising administering an effective amount of an anti-idiotype antibody or fragment thereof that specifically binds to the anti-FXI antibody.
53. An anti-idiotype antibody or fragment thereof that specifically binds to the anti-FXI antibody of any one of aspects 1-38, which blocks the anti-FXI antibody from binding to FXI, and wherein the anti-idiotype antibody or fragment thereof reverses the anti-coagulant activity of the anti-FXI antibody by at least 30% or by at least 40%.
54. A medicament comprising an antibody or antigen-binding fragment thereof according to any one of aspects 1-38.
55. A polynucleotide comprising nucleic acid sequences encoding a VL, VH or a VL and VH of the antibody or antigen-binding fragment of any one of aspects 1-38.
56. The polynucleotide of aspect 55, which encodes a heavy chain, light chain, or a heavy chain and light chain of the antibody or antigen-binding fragment of any one of aspects 1-38.
57. The polynucleotide of aspect 55 comprising a nucleic acid sequence set forth in Table 2.
58. A vector comprising the polynucleotide according to any one of aspects 55-57.
59. A host cell comprising the vector of aspect 58.
60. The host cell of aspect 59, which is a eukaryotic cell.
61. The host cell of aspect 59, which is a mammalian cell.
62. A method of producing an anti-FXI/FXIa antibody or fragment thereof, comprising the step of culturing the host cell of any one of aspects 59-61 under conditions suitable for expression of the anti-FXI/FXIa antibody or fragment thereof.
63. The method of aspect 62, further comprising purifying the anti-FXI/FXIa antibody or fragment thereof.
64. A method to reduce the risk of stroke and/or systemic embolism in a patient with atrial fibrillation, comprising administering to the patient a therapeutically effective amount of an antibody or antigen-binding fragment according to any one of aspects 1-38.
65. The method of aspect 64, wherein the patient has non-valvular atrial fibrillation.
66. The method of aspect 64 or 65, wherein the patient has a demonstrated high risk of bleeding.
67. A method of reducing the risk of stroke and/or systemic embolism in a patient with chronic kidney disease, comprising administering to the patient a therapeutically effective amount of an antibody or antigen-binding fragment according to any one of aspects 1-38.
68. The method of aspect 67, wherein patient has end stage renal disease (ESRD).
69. The method of aspect 67, wherein the patient has ESRD and is undergoing dialysis.
70. The method of aspect 69, wherein the patient has non-valvular atrial fibrillation.
71. The method of aspect 70, wherein the patient has a demonstrated high risk of bleeding.
72. The pharmaceutical composition according to aspect 39 or the medicament according to aspect 54 for use in a method of treating or managing or reducing the risk of a thromboembolic disorder in a subject.
73. The pharmaceutical composition or the medicament according to any one of the preceding aspects, wherein the subject is afflicated with, or is at risk of developing, one or more of stroke associated with atrial fibrillation and deep vein thrombosis.
74. The pharmaceutical composition or the medicament according to any one of the preceding aspects, wherein the subject is afflicated with, or at risk of developing, stroke associated with atrial fibrillation.
75. The pharmaceutical composition or the medicament according to any one of the preceding aspects, wherein the subject is afflicted with atrial fibrillation.
76. The pharmaceutical composition according to aspect 39 or the medicament according to aspect 54 for use in a method of preventing, treating or managing or reducing the risk of stroke in a subject.
77. The pharmaceutical composition or the medicament according to aspect 76, wherein the subject is afflicted with atrial fibrillation.
78. The pharmaceutical composition according to aspect 39 or the medicament according to aspect 54 for use in a method of treating or managing or reducing the risk of a thromboembolic disorder comprising administering the pharmaceutical composition or the medicament to a subject in need thereof in combination with one or more statin therapies.
79. Use of the antibody or antigen-binding fragment according to any one of aspects 1-38 in the preparation of a medicament for treating or managing or reducing the risk of a thromboembolic disorder.

Terminology

Unless defined otherwise, all technical and scientific terms used herein have the same meaning as commonly understood by those of ordinary skill in the art to which this present disclosure pertains.

The terms "FXI protein," "FXI antigen," and "FXI" are used interchangeably, and refers to the Factor XI protein in different species. Factor XI is the mammalian plasma coagulation factor XI, a glycoprotein present in human plasma at a concentration of 25-30 nM as a zymogen that when converted by limited proteolysis to an active serine protease, participates in the intrinsic pathway of blood coagulation.

The terms "FXIa protein," "FXIa antigen," and "FXIa", are used interchangeably, and refers to the activated FXI protein in different species. The zymogen Factor XI is converted into its active form, the coagulation factor XIa (FXIa), either via the contact phase of blood coagulation or through thrombin-mediated activation on the platelet surface. During this activation of factor XI, an internal peptide bond is cleaved in each of the two chains, resulting in the activated factor XIa, a serine protease composed of two heavy and two light chains held together by disulfide bonds. This serine protease FXIa converts the coagulation Factor IX into IXa, which subsequently activates coagulation Factor X (Xa). Xa then can mediate coagulation Factor II/Thrombin activation. For example, human FXI has the sequence as set out in Table 1 (SEQ ID NO:1), and has been described in previous reports and literature (Mandle R J Jr, et al. (1979) Blood; 54(4):850; NCBI Reference Sequence: AAA51985).

In the context of this disclosure, the terms "FXI" and "FXIa" (and the like) include mutants and variants of the natural FXI and FXIa protein, respectively, which have substantially the same amino acid sequence as that of the native primary structure (amino acid sequence) described in the above-mentioned reports.

The term "catalytic domain," "serine protease catalytic domain," and similar terms as used herein, means amino acids Ile370 to Val607, as counted from the Glu1 at the N-terminus of the mature protein that is in circulation. It can also be described as residues 388-625 at the C-terminus of FXI. As used herein, the term "active site" means the catalytic triad comprised of the amino acids His413, Asp462 and Se557. (Bane and Gailani (2014) Drug Disc. 19(9)).

The term "antibody" as used herein means a whole antibody and any antigen binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen binding portion" or "antigen binding fragment" of an antibody, as used herein, refers to one or more fragments of an intact antibody that retain the ability to specifically bind to a given antigen (e.g., Factor XIa (FXIa)). Antigen binding functions of an antibody can be performed by fragments of an intact antibody. Examples of binding fragments encompassed within the term antigen binding portion or antigen binding fragment of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain or a VL domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen binding portions or fragments of an antibody. These antibody fragments are obtained using conventional techniques known to those of skill in the art, and the fragments are screened for utility in the same manner as are intact antibodies.

Antigen binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen binding fragments thereof (e.g., a Fab fragment) generally refers to an antibody, or antigen binding fragment, having a $K_D$ of $10^{-9}$M or less (e.g., a $K_D$ of $10^{-10}$ M or less, a $K_D$ of $10^{-11}$M or less, a $K_D$ of $10^{-12}$M or less, a $K_D$ of $10^{-13}$M or less, a $K_D$ of $10^{-14}$M or less, etc.).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant.

The phrase "specifically (or selectively) binds" to an antibody (e.g., a FXI and/or FXIa-binding antibody) refers to a binding reaction that is determinative of the presence of a cognate antigen (e.g., a human FXI and/or FXIa or cynomolgus FXI and/or FXIa) in a heterogeneous population of proteins and other biologics. The phrases "an antibody recognizing an antigen" and "an antibody specific for an antigen" are used interchangeably herein with the term "an antibody which binds specifically to an antigen".

The term "FXI and/or FXIa mediated" refers to the fact that FXI and/or FXIa mediates the intrinsic and/or common coagulation pathways by directly or indirectly activating Factor IX (also known as FIX), Factor X (FX), and/or thrombin, and/or by binding to platelet receptors.

The term "hemostasis" represents the principal mechanisms for arresting the flow of blood at sites of injury and restoring vascular patency during wound healing, respectively. During normal hemostasis and pathological thrombosis, three mechanisms become activated simultaneously: primary hemostasis meaning the interactions of activated platelets with the vessel wall, the formation of fibrin, and a process termed as fibrinolysis.

The terms "coagulation and coagulation cascade," "cascade model of coagulation," and the like, refer to the protein based system which serves to stabilize a clot that has formed to seal up a wound. The coagulation pathway is a proteolytic cascade. Each enzyme of the pathway is present in the plasma as a Zymogen (in an inactive form), which on activation undergoes proteolytic cleavage to release the active factor from the precursor molecule. The coagulation cascade functions as a series of positive and negative feedback loops which control the activation process. The ultimate goal of the pathway is to produce thrombin, which can then convert soluble fibrinogen into fibrin that forms a clot.

The process of generation of thrombin can be divided into three phases: the intrinsic and extrinsic pathways, which provide alternative routes for the generation of an active clotting factor: FXa (Activated Factor-X), and the final common pathway, which results in thrombin formation (Hoffman M. M. and Monroe D. M. (2005) Curr Hematol Rep. 4:391-396; Johne J, et al. (2006) Biol Chem. 387:173-178).

"Platelet aggregation" refers to the process whereby when a break in a blood vessel occurs, substances are exposed that normally are not in direct contact with the blood flow. These substances (primarily collagen and von Willebrand factor) allow the platelets to adhere to the broken surface. Once a platelet adheres to the surface, it releases chemicals that attract additional platelets to the damaged area, referred to as platelet aggregation. These two processes are the first responses to stop bleeding.

A "thromboembolic disorder," or similar terms as used herein, refer to any number of conditions or diseases in which the intrinsic and/or common coagulation pathways are aberrantly activated or are not naturally deactivated (e.g., without therapeutic means). These conditions include but are not limited to thrombic stroke, atrial fibrillation, stroke prevention in atrial fibrillation (SPAF), deep vein thrombosis, venous thromboembolism, and pulmonary embolism. These can also include catheter-related conditions (e.g., Hickman catheter in oncology patients) in which catheters become thrombosed, and extracorporeal membrane oxygenation (ECMO), in which the tubing develops clots.

A "thromboembolic," or similar terms as used herein, can also refer to any number of the following, which the anti-FXI and/or FXIa Abs or antigen binding fragments thereof of the present disclosure can be used to prevent or treat:

thromboembolism in subjects with suspected or confirmed cardiac arrhythmia such as paroxysmal, persistent or permanent atrial fibrillation or atrial flutter;

stroke prevention in atrial fibrillation (SPAF), a subpopulation of which is AF patients undergoing percutaneous coronary interventions (PCI);

acute venous thromboembolic events (VTE) treatment and extended secondary VTE prevention in patients at high risk for bleeding;

cerebral and cardiovascular events in secondary prevention after transient ischemic attack (TIA) or non-disabling stroke and prevention of thromboembolic events in heart failure with sinus rhythm;

clot formation in left atrium and thromboembolism in subjects undergoing cardioversion for cardiac arrhythmia;

thrombosis before, during and after ablation procedure for cardiac arrhythmia;
   venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;

thrombosis on any artificial surface in the veins like catheter or pacemaker wires;

pulmonary embolism in patients with or without venous thrombosis;

Chronic Thromboembolic Pulmonary Hypertension (CTEPH);

arterial thrombosis on ruptured atherosclerotic plaque, thrombosis on intra-arterial prosthesis or catheter and thrombosis in apparently normal arteries, this includes but not limited to acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;

thrombosis and thromboembolism in patients undergoing percutaneous coronary interventions (PCI);

cardioembolic and cryptogenic strokes;

thrombosis in patients with invasive and non-invasive cancer malignancies;

thrombosis over an indwelling catheter;

thrombosis and thromboembolism in severely ill patients;

cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;

thromboembolism in patients with valvular heart disease with or without atrial fibrillation;

thromboembolism over valvular mechanic or biologic prostheses;

thromboembolism in patients who had native or artificial cardiac patches, arterial or venous conduit tubes after heart repair of simple or complex cardiac malformations;

venous thrombosis and thromboembolism after knee replacement surgery, hip replacement surgery, and orthopedic surgery, thoracic or abdominal surgery;

arterial or venous thrombosis after neurosurgery including intracranial and spinal cord interventions;

congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;

thrombosis and thromboembolism in chronic kidney disease; and thrombosis and thromboembolism in patients undergoing hemodialysis and in patients undergoing extra-corporal membrane oxygenation.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the present disclosure. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Two antibodies are said to "compete" if one antibody is shown to bind the same epitope as the second antibody in a competitive binding assay, by any of the methods well known to those of skill in the art.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the present disclosure may include amino acid residues not encoded by human sequences (e.g., mutations introduced by random or site-specific mutagenesis in vitro or by somatic mutation in vivo).

The term "human monoclonal antibody" refers to antibodies displaying a single binding specificity which have variable regions in which both the framework and CDR regions are derived from human sequences. In one embodiment, the human monoclonal antibodies are prepared using phage display methods for screening libraries of human immunoglobulin genes.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, John Wiley & Sons, Inc. (Ringbou ed., 2003)).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=-4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" refers to an antibody that is substantially free of other antibodies having different antigenic specificities (e.g., an isolated antibody that specifically binds FXI and/or FXIa is substantially free of antibodies that specifically bind antigens other than FXI and/or FXIa). An isolated antibody that specifically binds FXI and/or FXIa may, however, have cross-reactivity to other antigens. Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. Methods for determining the $K_D$ of an antibody include measuring surface plasmon resonance using a biosensor system such as a Biacore™ system, or measuring affinity in solution by solution equilibrium titration (SET).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, the term refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates (e.g.: mammals and non-mammals) such as, non-human primates (e.g.: cynomolgus monkey), sheep, rabbit, dog, cow, chickens, amphibians, and reptiles. Except when noted, the terms "patient" or "subject" are used herein interchangeably. As used herein, the terms "cyno" or "cynomolgus" refer to the cynomolgus monkey (Macaca fascicularis).

As used herein, the term "treating" or "treatment" of any disease or disorder (e.g., a thromboembolic disorder) refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

"Prevention" as it relates to indications described herein, including, e.g., a thromboembolic disorder, means any action that prevents or slows a worsening in e.g., a thromboembolic disease parameters, as described below, in a patient at risk for being afflicted with a thromboembolic disorder or at risk for said worsening.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, such as an adeno-associated viral vector (AAV, or AAV2), wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present disclosure is intended to include such other forms of expression vectors, such as viral vectors (e.g., replication defective retroviruses, adenoviruses and adeno-associated viruses), which serve equivalent functions.

BRIEF DESCRIPTION OF THE DRAWINGS

FIG. 1A shows the ELISA curves for antibody binding to human plasma-derived FXI and FXIa. FIG. 1B shows the ELISA curves for antibody binding to cynomolgus monkey and rabbit FXI. FIG. 1C shows the ELISA curves for antibody binding to human pre-kallikrein and human kallikrein.

DETAILED DESCRIPTION

Figure 1A:
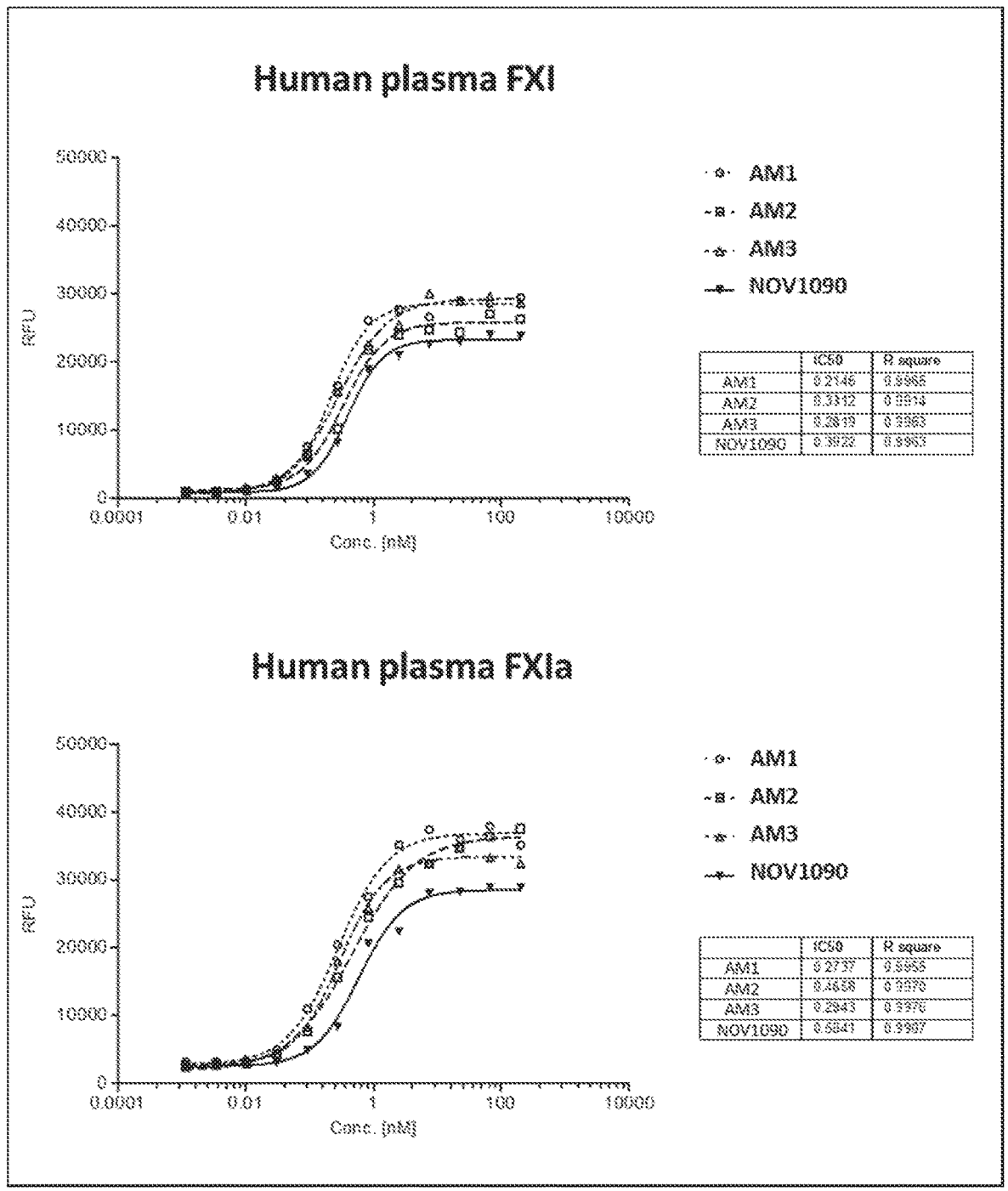
FIGS. 1A-C show ELISA binding curves for FXIa antibodies, NOV1090 and three affinity matured antibodies AM1, AM2 and AM3 derived from NOV1090.

The present disclosure is based, in part, on the discovery of antibody molecules that specifically bind to FXI and/or FXIa and inhibit its biological activities, and in particular of antibody molecules that specifically bind to zymogen FXI and FXIa and inhibit its biological activities. The present disclosure relates to both full IgG format antibodies as well as antigen-binding fragments thereof, such as Fab fragments (e.g., antibodies AM1, AM2, AM3, and AM4).

Accordingly, the present disclosure provides antibodies that specifically bind to FXI and/or FXIa (e.g., human, rabbit, and cynomolgus monkey FXI and/or FXIa), pharmaceutical compositions, production methods, and methods of use of such antibodies and compositions.

Factor XI

FXI holds important roles in both intrinsic and extrinsic coagulation pathways and in bridging the initiation and amplification phases of plasmatic hemostasis. Both Factor XIIa and thrombin can activate FXI, resulting in a sustained thrombin generation and fibrinolysis inhibition. FXI plays a minor role in normal hemostasis in a high tissue factor environment "after vessel injury" whereas it appears to play a key role in thrombosis. Severe Factor XI deficiency is associated with a lower incidence of ischemic stroke and venous thromboembolic events (Salomon et al 2008; Salomon, et al. (2011) Thromb Haemost.; 105:269-73). Bleeding manifestations in subjects with severe factor XI deficiency are infrequent, often mild, injury-induced and affect preferably tissues with increased fibrinolytic activity such as the oral mucosa, nasal mucosa and urinary tract (Salomon et al 2011). Bleeding in critical organs is extremely rare or not existing.

Plasma coagulation is a sequential process by which coagulation factors in the blood interact and are activated, ultimately resulting in fibrin generation and clot formation. In the classical cascade model of coagulation, the process of fibrin generation can be initiated by two distinct pathways, i.e., the intrinsic and the extrinsic pathway, respectively (Mackman, 2008).

In the extrinsic pathway, vessel injury allows extravascular tissue factor (TF) to interact with and activate factor VII (FVII), which sequentially leads to the activation of factor X and prothrombin. The active thrombin ultimately converts soluble fibrinogen into fibrin. The extrinsic pathway is central for hemostasis, interfering with coagulation factors in this pathway results in a risk of bleeding.

In the intrinsic pathway, factor XII may in some cases be activated by a process referred to as contact activation. Generation of activated factor XIIa leads to the sequential activations of factor XI and factor IX. As factor IXa activates factor X, the extrinsic and intrinsic pathways converge at this stage (at the common pathway). Thrombin activity is boosted by amplifying its own generation through a feed-forward loop in which thrombin activates factor XI independently of factor XII. This feed-forward loop contributes to sustained thrombus growth but is only minimally involved in hemostasis, as the strong activation by extravascular tissue factor is sufficient to clot formation. The intrinsic pathway therefore is not substantially involved in hemostasis (Gailani and Renné (2007) Arterioscler Thromb Vasc Biol. 2007, 27(12):2507-13, Müller, Gailani, and Renné 2011).

Preclinical studies using a variety of approaches to inhibit FXI or FXIa across a variety of species have contributed to the validation of this target. FXI−/− mice are resistant to experimental venous (Wang, et al. (2006) J Thromb Haemost; 4:1982-8) and arterial (Wang, et al. (2005) J Thromb Haemost; 3:695-702) thrombosis. Treatment of mice with an antibody (Ab, 14E11) that blocks the activation of FXI by FXIIa resulted in inhibition of experimental thrombosis (Cheng, et al. (2010) Blood, 116:3981-9) and reduced cerebral infarct size in a mouse model of ischemic stroke (Leung, et al. (2012) Transl Stroke Res 2012; 3:381-9). In baboons administered an anti-FXI Ab that blocks binding and activation of FIX by FXIa, reduced growth of platelet-rich thrombi was observed on collagen-coated vascular grafts (Tucker, et al. (2009) Blood 2009; 113:936-44), and similar results were found with 14E11 in this model (Cheng 2010). Excessive bleeding was not noted in any of these studies.

Blocking FXI synthesis with antisense oligonucleotides in mice (Zhang, et al. (2010) Blood 2010; 116:4684-92), cynomolgus monkeys (Younis, et al. (2012) Blood 2012; 119:2401-8), and baboons (Crosby, et al. (2013) Arterioscler Thromb Vasc Biol 2013; 33:1670-8) resulted in antithrombotic and anticoagulant effects without excessive bleeding. Moreover, similar effects have been produced by blocking FXIa with low molecular weight inhibitors in venous and arterial models of thrombosis in rats (Schumacher, et al. (2007) Eur J Pharmacol 2007; 570:167-74) and rabbits (Wong, et al. (2011) J Thromb Thrombolysis 2011; 32:129-37).

Patients with severe FXI deficiency rarely bleed spontaneously and they show only mild trauma-induced bleeding, except in tissues with high fibrinolytic activity. The rarity of severe FXI deficiency necessitates the use of population studies for revealing the thrombotic profile of these patients relative to the general population. Notably, such studies report the incidence of ischemic stroke (Salomon 2008) and deep vein thrombosis (DVT) (Salomon, et al. (2011) Blood 2008; 111: 4113-17) to be reduced in these patients. Thus, the number of ischemic strokes (N=1) observed in 115 patients with severe FXI deficiency was less (p<0.003) than the expected incidence (N=8.6) in the general population of Israel, while the incidence of DVT (N=0) was lower (p<0.019) in patients with severe FXI deficiency than expected in the control population (N=4.7). Conversely, individuals with FXI levels above the 90th percentile had a two-fold risk of developing DVT (Meijers, et al. (2000) N Engl J Med. 2000; 342:696-701).

Recently, patients undergoing total knee replacement, a procedure that predisposes to DVT, were treated with FXI antisense therapy or standard of care (enoxaparin). The antisense group (300 mg) showed a 7-fold decreased incidence in venous thrombosis and fewer (not significant) bleeding events compared to standard of care (Buller et al, (2014) N Engl J Med. 372(3):232-40. doi: 10.1056/NEJMoa1405760. Epub 2014 Dec. 7).

FXI/FXIa Antibodies & Antigen Binding Fragments

The present disclosure provides antibodies (e.g., monoclonal antibodies, such as human monoclonal antibodies) that specifically bind to human FXI and/or FXIa. In some embodiments, the present disclosure provides antibodies that specifically bind to human, rabbit, and cynomolgus monkey FXI and/or FXIa. Antibodies provided herein include, but are not limited to, human monoclonal antibodies and Fabs, for example isolated as described in the Examples.

In one aspect, isolated antibodies, or antigen binding fragments thereof, bind to active FXI (FXIa) and leads upon binding to the active FXI (FXIa) catalytic domain to FXIa changing its conformation to an inactive conformation. In another aspect, said isolated antibodies or antigen binding fragments thereof further induce a change in which the N-terminal 4 residues, loops 145, 188 and 220 of said inactive conformation are shifted and/or disordered compared to the active conformation.

In one aspect, isolated antibodies, or antigen binding fragments thereof, bind to FXI (e.g., human FXI) and upon binding to FXI prevent the FXI catalytic domain from assuming an active conformation, in which loops 145, 188 and 220 are ordered as in the structure of the FXIa catalytic domain.

In one aspect, isolated antibodies, or antigen binding fragments thereof, bind to FXI and upon binding to FXI prevents the FXI catalytic domain from assuming an active conformation, in which the N-terminal 4 residues, loops 145, 188 and 220 are ordered as in the structure of the FXIa catalytic domain.

In one aspect, isolated antibodies, or antigen binding fragments thereof, bind to FXI and upon binding to FXI prevents the FXI catalytic domain from assuming an active conformation by inducing conformational changes in the zymogen structure, further leading to an inhibited FXI conformation closely related to that observed when binding to FXIa.

In one aspect, isolated antibodies, or antigen binding fragments thereof, bind to FXI and/or FXIa and upon binding to FXI and/or FXIa and forming an antibody: antigen complex with the catalytic domain of FXI and/or FXIa cause a shift and/or disorientation of loops 145, 188 and 220 when compared with the uncomplexed structure of the catalytic domain of active Factor XI (FXIa).

In one aspect, isolated antibodies, or antigen binding fragments thereof, bind to FXI and/or FXIa upon binding to FXI and/or FXIa and forming an antibody: antigen complex with the catalytic domain of FXI and/or FXIa causes a shift and/or disorientation of the N-terminal 4 residues, loops 145, 188 and 220 when compared with the uncomplexed structure of the catalytic domain of active Factor XI (FXIa).

In one aspect, isolated antibodies, or antigen binding fragments thereof, bind to active FXI (FXIa) and cause the FXI (FXIa) catalytic domain to change its conformation to an inactive conformation, in which loops 145, 188 and 220 are shifted and/or disoriented compared to the active conformation.

In one aspect, isolated antibodies, or antigen binding fragments thereof, bind to FXI and prevent the catalytic domain from assuming an active conformation by inducing a conformational changes in the zymogen structure, thereby leading to an inhibited FXI conformation closely related to that observed when binding to FXIa.

In specific aspects, the present disclosure provides antibodies that specifically bind a FXI and/or FXIa protein (e.g., human, rabbit, and cynomolgus monkey FXI and/or FXIa), wherein the antibodies comprise sequences selected from those described in Table 2. In a particular aspect, antibodies provided herein comprise sequences selected from those described in Table 2, but do not contain sequences (e.g., CDRs or variable region sequences) described in Table 1.

In a particular aspect, provided herein is an isolated anti-FXI antibody or antigen-binding fragment thereof that binds within the catalytic domain of FXI and/or FXIa comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein
  HCDR1 comprises an amino acid sequence selected from the group consisting of SEQ ID NOs: 3, 6, 7, and 9;
  HCDR2 comprises an amino acid sequence selected from the group consisting of:
    (i) SEQ ID NO: 59 (X1-I-X2-X3-X4-X5-X6-X7-T-X8-YADSVKG), wherein X1 is any amino acid or is T or S, X2 is any amino acid or is D or E, X3 is any amino acid or is Y or S, X4 is any amino acid or is S, Y, or W, X5 is any amino acid or is S, D, or G, X6 is any amino acid or is Q, T, or D, X7 is any amino acid or is D or E, and X8 is any amino acid or is Y, H or D, wherein HCDR2 is not SEQ ID NO: 4,
    (ii) SEQ ID NO: 60 (X1-X2-X3-X4-X5-X6), wherein X1 is any amino acid or is E or D, X2 is any amino acid or is Y or S, X3 is any amino acid or is Y, S or W, X4 is any amino acid or is S, D, or G, X5 is any amino acid or is D, T, or Q, and X6 is any amino acid or is D or E, wherein HCDR2 is not SEQ ID NO: 8, and
    (iii) SEQ ID NO: 61 (I-X1-X2-X3-X4-X5-X6-T), wherein X1 is any amino acid or is E or D, X2 is any amino acid or is Y or S, X3 is any amino acid or is S, Y, or W, X4 is any amino acid or is S, D, or G, X5 is any amino acid or is D, T, or Q, and X6 is any amino acid or is D or E, wherein HCDR2 is not SEQ ID NO: 10;
  HCDR3 comprises an amino acid sequence selected from the group consisting of SEQ ID NOs: 5 and 11;
  LCDR1 comprises an amino acid sequence selected from the group consisting of SEQ ID NOs: 16, 19, and 22;
  LCDR2 comprises an amino acid sequence selected from the group consisting of SEQ ID NOs: 17 and 20; and
  LCDR3 comprises an amino acid sequence selected from the group consisting of SEQ ID NOs: 18 and 21.

In a particular aspect, provided herein is an isolated anti-FXI antibody or antigen-binding fragment thereof that binds within the catalytic domain of FXI and/or FXIa comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein
  (i) HCDR1 comprises the amino acid sequence of SEQ ID NO: 3;
  (ii) HCDR2 comprises the amino acid sequence of SEQ ID NO: 59 (X1-I-X2-X3-X4-X5-X6-X7-T-X8-YADSVKG), wherein X1 is any amino acid or is T or S, X2 is any amino acid or is D or E, X3 is any amino acid or is Y or S, X4 is any amino acid or is S, Y, or W, X5 is any amino acid or is S, D, or G, X6 is any amino acid or is Q, T, or D, X7 is any amino acid or is D or E, and X8 is any amino acid or is Y, H or D, and wherein HCDR2 is not SEQ ID NO: 4;
  (iii) HCDR3 comprises the amino acid sequence of SEQ ID NO: 5;
  (iv) LCDR1 comprises the amino acid sequence of SEQ ID NO: 16;
  (v) LCDR2 comprises the amino acid sequence of SEQ ID NO: 17; and
  (vi) LCDR3 comprises the amino acid sequence of SEQ ID NO: 18. In specific embodiments, the HCDR2 comprises the amino acid sequence of SEQ ID NO: 59 (X1-I-X2-X3-X4-X5-X6-X7-T-X8-YADSVKG), wherein X1 is T or S, X2 is D or E, X3 is Y or S, X4 is S, Y, or W, X5 is S, D, or G, X6 is Q, T, or D, X7 is D or E, and X8 is Y, H or D, and wherein HCDR2 is not SEQ ID NO: 4.

In a particular aspect, provided herein is an isolated anti-FXI antibody or antigen-binding fragment thereof that binds within the catalytic domain of FXI and/or FXIa comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein
  (i) HCDR1 comprises the amino acid sequence of SEQ ID NO: 6;
  (ii) HCDR2 comprises the amino acid sequence of SEQ ID NO: 59 (X1-I-X2-X3-X4-X5-X6-X7-T-X8-YADSVKG), wherein X1 is any amino acid or is T or S, X2 is any amino acid or is D or E, X3 is any amino acid or is Y or S, X4 is any amino acid or is S, Y, or W, X5 is any amino acid or is S, D, or G, X6 is any amino acid or is Q, T, or D, X7 is any amino acid or is D or E, and X8 is any amino acid or is Y, H or D, and wherein HCDR2 is not SEQ ID NO: 4;
  (iii) HCDR3 comprises the amino acid sequence of SEQ ID NO: 5;
  (iv) LCDR1 comprises the amino acid sequence of SEQ ID NO: 16;
  (v) LCDR2 comprises the amino acid sequence of SEQ ID NO: 17; and
  (vi) LCDR3 comprises the amino acid sequence of SEQ ID NO: 18. In further specific aspects, the HCDR2 comprises the amino acid sequence of SEQ ID NO: 59 (X1-I-X2-X3-X4-X5-X6-X7-T-X8-YADSVKG), wherein X1 is T or S, X2 is D or E, X3 is Y or S, X4 is S, Y, or W, X5 is S, D, or G, X6 is Q, T, or D, X7 is D or E, and X8 is Y, H or D, and wherein HCDR2 is not SEQ ID NO: 4.

In a particular aspect, provided herein is an isolated anti-FXI antibody or antigen-binding fragment thereof that binds within the catalytic domain of FXI and/or FXIa comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein
  (i) HCDR1 comprises the amino acid sequence of SEQ ID NO: 7;
  (ii) HCDR2 comprises the amino acid sequence of SEQ ID NO: 60 (X1-X2-X3-X4-X5-X6), wherein X1 is any amino acid or is E or D, X2 is any amino acid or is Y or S, X3 is any amino acid or is Y, S or W, X4 is any amino acid or is S, D, or G, X5 is any amino acid or is D, T, or Q, and X6 is any amino acid or is D or E, and wherein HCDR2 is not SEQ ID NO: 8;
  (iii) HCDR3 comprises the amino acid sequence of SEQ ID NO: 5;
  (iv) LCDR1 comprises the amino acid sequence of SEQ ID NO: 19;
  (v) LCDR2 comprises the amino acid sequence of SEQ ID NO: 20; and
  (vi) LCDR3 comprises the amino acid sequence of SEQ ID NO: 21. In further specific embodiments, the HCDR2 comprises the amino acid sequence of SEQ ID NO: 60 (X1-X2-X3-X4-X5-X6), wherein X1 is E or D, X2 is Y or S, X3 is Y, S or W, X4 is S, D, or G, X5 is D, T, or Q, and X6 is D or E, and wherein HCDR2 is not SEQ ID NO: 8;

In a particular aspect, provided herein is an isolated anti-FXI antibody or antigen-binding fragment thereof that binds within the catalytic domain of FXI and/or FXIa comprising a heavy chain variable region (VH) comprising complementarity determining regions HCDR1, HCDR2, and HCDR3, and a light chain variable region (VL) comprising complementarity determining regions LCDR1, LCDR2, and LCDR3, wherein
- (i) HCDR1 comprises the amino acid sequence of SEQ ID NO: 9;
- (ii) HCDR2 comprises the amino acid sequence of SEQ ID NO: 61 (I-X1-X2-X3-X4-X5-X6-T), wherein X1 is any amino acid or is E or D, X2 is any amino acid or is Y or S, X3 is any amino acid or is S, Y, or W, X4 is any amino acid or is S, D, or G, X5 is any amino acid or is D, T, or Q, and X6 is any amino acid or is D or E, and wherein HCDR2 is not SEQ ID NO: 10;
- (iii) HCDR3 comprises the amino acid sequence of SEQ ID NO: 11;
- (iv) LCDR1 comprises the amino acid sequence of SEQ ID NO: 22;
- (v) LCDR2 comprises the amino acid sequence of SEQ ID NO: 20; and
- (vi) LCDR3 comprises the amino acid sequence of SEQ ID NO: 18. In further specific aspects, the HCDR2 comprises the amino acid sequence of SEQ ID NO: 61 (I-X1-X2-X3-X4-X5-X6-T), wherein X1 is E or D, X2 is Y or S, X3 is S, Y, or W, X4 is S, D, or G, X5 is D, T, or Q, and X6 is D or E, and wherein HCDR2 is not SEQ ID NO: 10

In a particular aspect, provided herein is an isolated anti-FXI antibody or antigen-binding fragment thereof that binds within the catalytic domain of FXI and/or FXIa comprising (i) a heavy chain variable region (VH) comprising complementarity determining regions HCDR1, HCDR2, and HCDR3, and (ii) a light chain variable region (VL) comprising complementarity determining regions LCDR1, LCDR2, and LCDR3, wherein the HCDR1 comprises an amino acid sequence selected from the group consisting of SEQ ID NOs: 3, 6, 7, and 9;
- the HCDR2 comprises an amino acid sequence selected from the group consisting of SEQ ID NOs: 27, 28, 29, 38, 39, 40, 45, 46, and 47;
- the HCDR3 comprises an amino acid sequence selected from the group consisting of SEQ ID NOs: 5 and 11;
- the LCDR1 comprises an amino acid sequence selected from the group consisting of SEQ ID NOs: 16, 19, and 22;
- the LCDR2 comprises an amino acid sequence selected from the group consisting of SEQ ID NOs: 17 and 20; and the LCDR3 comprises an amino acid sequence selected from the group consisting of SEQ ID NOs: 18 and 21.

In a specific embodiment, provided herein is an antibody or antigen-binding fragment thereof that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein
- (i) the HCDR1 comprises the amino acid sequence of SEQ ID NO: 3, the HCDR2 comprises the amino acid sequence of SEQ ID NO: 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
- (ii) the HCDR1 comprises the amino acid sequence of SEQ ID NO: 6, the HCDR2 comprises the amino acid sequence of SEQ ID NO: 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
- (iii) the HCDR1 comprises the amino acid sequence of SEQ ID NO: 7, the HCDR2 comprises the amino acid sequence of SEQ ID NO: 46, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21; or (iv) the HCDR1 comprises the amino acid sequence of SEQ ID NO: 9, the HCDR2 comprises the amino acid sequence of SEQ ID NO: 47, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

In a certain aspect, provided herein is an antibody or antigen-binding fragment thereof that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein
- (i) the HCDR1 comprises the amino acid sequence of SEQ ID NO: 3, the HCDR2 comprises the amino acid sequence of SEQ ID NO: 38, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
- (ii) the HCDR1 comprises the amino acid sequence of SEQ ID NO: 6, the HCDR2 comprises the amino acid sequence of SEQ ID NO: 38, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
- (iii) the HCDR1 comprises the amino acid sequence of SEQ ID NO: 7, the HCDR2 comprises the amino acid sequence of SEQ ID NO: 39, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21; or (iv) the HCDR1 comprises the amino acid sequence of SEQ ID NO: 9, the HCDR2 comprises the amino acid sequence of SEQ ID NO: 40, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

In a specific aspect, provided herein is an antibody or antigen-binding fragment thereof that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein
  (i) the HCDR1 comprises the amino acid sequence of SEQ ID NO: 3, the HCDR2 comprises the amino acid sequence of SEQ ID NO: 27, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
  (ii) the HCDR1 comprises the amino acid sequence of SEQ ID NO: 6, the HCDR2 comprises the amino acid sequence of SEQ ID NO: 27, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;
  (iii) the HCDR1 comprises the amino acid sequence of SEQ ID NO: 7, the HCDR2 comprises the amino acid sequence of SEQ ID NO: 28, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21; or
  (iv) the HCDR1 comprises the amino acid sequence of SEQ ID NO: 9, the HCDR2 comprises the amino acid sequence of SEQ ID NO: 29, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

In a particular aspect, provided herein is an antibody or antigen-binding fragment thereof that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the HCDR1 comprises the amino acid sequence of SEQ ID NO: 3, the HCDR2 comprises the amino acid sequence of SEQ ID NO: 27, 38, or 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18.

In a specific aspect, provided herein is an antibody or antigen-binding fragment thereof that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the HCDR1 comprises the amino acid sequence of SEQ ID NO: 6, the HCDR2 comprises the amino acid sequence of SEQ ID NO: 27, 38, or 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18;

In a specific aspect, provided herein is an antibody or antigen-binding fragment that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the HCDR1 comprises the amino acid sequence of SEQ ID NO: 7, the HCDR2 comprises the amino acid sequence of SEQ ID NO: 28, 39, or 46, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21.

In a particular aspect, provided herein is an antibody or antigen-binding fragment thereof that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the HCDR1 comprises the amino acid sequence of SEQ ID NO: 9, the HCDR2 comprises the amino acid sequence of SEQ ID NO: 29, 40, or 47, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18.

In a certain aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 selected from Table 2, and wherein the VL comprises complementarity determining regions LCDR1, LCDR2, and LCDR3 selected from Table 2.

In a particular aspect, provided herein is an antibody or antigen-binding fragment thereof that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the VH comprises Combined HCDR1, HCDR2, and HCDR3 of antibody AM1, AM2, AM3, or AM4, and the VL comprises Combined LCDR1, LCDR2, and LCDR3 of antibody AM1, AM2, AM3, or AM4.

In a particular aspect, provided herein is an antibody or antigen-binding fragment that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the VH comprises Kabat HCDR1, HCDR2, and HCDR3 of antibody AM1, AM2, AM3, or AM4, and the VL comprises Kabat LCDR1, LCDR2, and LCDR3 of AM1, AM2, AM3, or AM4.

In a particular aspect, provided herein is an antibody or antigen-binding fragment that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the VH comprises Chothia HCDR1, HCDR2, and HCDR3 or antibody AM1, AM2, AM3, or AM4, and the VL comprises Chothia LCDR1, LCDR2, and LCDR3 of antibody AM1, AM2, AM3, or AM4.

In a particular aspect, provided herein is an antibody or antigen-binding fragment that binds within the catalytic domain of FXI and/or FXIa comprising (a) a heavy chain variable region (VH) comprising complementarity determining regions HCDR1, HCDR2, and HCDR3, and (b) a light chain variable region (VL) comprising complementarity determining regions LCDR1, LCDR2, and LCDR3, wherein the VH comprises IMGT HCDR1, HCDR2, and HCDR3 of antibody AM1, AM2, AM3, or AM4, and the VL comprises IMGT LCDR1, LCDR2, and LCDR3 of antibody AM1, AM2, AM3, or AM4.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 of antibody AM2, and wherein the VL comprises complementarity determining regions LCDR1, LCDR2, and LCDR3 of antibody AM2.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 of antibody AM3 or AM4, and wherein the VL comprises complementarity determining regions LCDR1, LCDR2, and LCDR3 of antibody AM3 or AM4.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises complementarity determining regions HCDR1, HCDR2, and HCDR3 of antibody AM1, and wherein the VL comprises complementarity determining regions LCDR1, LCDR2, and LCDR3 of antibody AM1.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises the amino acid sequence of SEQ ID NOs: 30, 41, and 48; and the VL comprises the amino acid sequence of SEQ ID NO: 34 or 55.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises the amino acid sequence of SEQ ID NO: 48 and the VL comprises the amino acid sequence of SEQ ID NO: 55.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises the amino acid sequence of SEQ ID NO: 48 and the VL comprises the amino acid sequence of SEQ ID NO: 34.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises the amino acid sequence of SEQ ID NO: 41 and the VL comprises the amino acid sequence of SEQ ID NO: 34.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises the amino acid sequence of SEQ ID NO: 30 and the VL comprises the amino acid sequence of SEQ ID NO: 34.

In a specific aspect, provided herein is an isolated anti-FXI antibody or antigen-binding fragment thereof that binds within the catalytic domain of FXI and/or FXIa comprising a heavy chain and a light chain, wherein the heavy chain comprises the amino acid sequence of SEQ ID NOs: 32, 43, 50, or 53; and the light chain comprises the amino acid sequence of SEQ ID NO: 57 or 36.

In a specific aspect, provided herein is an isolated anti-FXI antibody or antigen-binding fragment thereof that binds within the catalytic domain of FXI and/or FXIa comprising a heavy chain and a light chain, wherein the heavy chain comprises the amino acid sequence of SEQ ID NO: 53 and the light chain comprises the amino acid sequence of SEQ ID NO: 57.

In a specific aspect, provided herein is an isolated anti-FXI antibody or antigen-binding fragment thereof that binds within the catalytic domain of FXI and/or FXIa comprising a heavy chain and a light chain, wherein the heavy chain comprises the amino acid sequence of SEQ ID NO: 50 and the light chain comprises the amino acid sequence of SEQ ID NO: 36.

In a specific aspect, provided herein is an isolated anti-FXI antibody or antigen-binding fragment thereof that binds within the catalytic domain of FXI and/or FXIa comprising a heavy chain and a light chain, wherein the heavy chain comprises the amino acid sequence of SEQ ID NO: 43 and the light chain comprises the amino acid sequence of SEQ ID NO: 36.

In a specific aspect, provided herein is an isolated anti-FXI antibody or antigen-binding fragment thereof that binds within the catalytic domain of FXI and/or FXIa comprising a heavy chain and a light chain, wherein the heavy chain comprises the amino acid sequence of SEQ ID NO: 32 and the light chain comprises the amino acid sequence of SEQ ID NO: 36.

TABLE 1

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| Human FXI full-length protein sequence (NCBI Reference Sequence: AAA51985) | 1 | MIFLYQVVHF ILFTSVSGEC VTQLLKDTCF EGGDITTVFT<br>PSAKYCQVVC TYHPRCLLFT FTAESPSEDP TRWFTCVLKD<br>SVTETLPRVN RTAAISGYSF KQCSHQISAC NKDIYVDLDM<br>KGINYNSSVA KSAQECQERC TDDVHCHFFT YATRQFPSLE<br>HRNICLLKHT QTGTPTRITK LDKVVSGFSL KSCALSNLAC<br>IRDIFPNTVF ADSNIDSVMA PDAFVSGRIC THHPGCLFFT<br>FFSQEWPKES QRNLCLLKTS ESGLPSTRIK KSKALSGFSL<br>QSCRHSIPVF CHSSFYHDTD FLGEELDIVA AKSHEACQKL<br>CTNAVRCQFF TYTPAQASCN EGKGKCYLKL SSNGSPTKIL<br>HGRGGISGYT LRLCKMDNEC TTKIKPRIVG GTASVRGEWP<br>WQVTLHTTSP TQRHLCGGSI IGNQWILTAA HCFYGVESPK<br>ILRVYSGILN QSEIKEDTSF FGVQEIIIHD QYKMAESGYD<br>IALLKLETTV NYTDSQRPIC LPSKGDRNVI YTDCWVTGWG<br>YRKLRDKIQN TLQKAKIPLV TNEECQKRYR GHKITHKMIC<br>AGYREGGKDA CKGDSGGPLS CKHNEVWHLV GITSWGEGCA<br>QRERPGVYTN VVEYVDWILE KTQAV |
| Human FXI full-length nucleotide sequence (NCBI Reference Sequence: NM_000128.3) | 2 | AGGCACACAG GCAAAATCAA GTTCTACATC TGTCCCTGTG<br>TATGTCACTT GTTTGAATAC GAAATAAAAT TAAAAAAATA<br>AATTCAGTGT ATTGAGAAAG CAAGCAATTC TCTCAAGGTA<br>TATTTCTGAC ATACTAAGAT TTTAACGACT TTCACAAATA<br>TGCTGTACTG AGAGAGAATG TTACATAACA TTGAGAACTA<br>GTACAAGTAA ATATTAAAGT GAAGTGACCA TTTCCTACAC<br>AAGCTCATTC AGAGGAGGAT GAAGACCATT TTGGAGGAAG<br>AAAAGCACCC TTATTAAGAA TTGCAGCAAG TAAGCCAACA<br>AGGTCTTTTC AGGATGATTT TCTTATATCA AGTGGTACAT<br>TTCATTTTAT TTACTTCAGT TTCTGGTGAA TGTGTGACTC<br>AGTTGTTGAA GGACACCTGC TTTGAAGGAG GGGACATTAC<br>TACGGTCTTC ACACCAAGCG CCAAGTACTG CCAGGTAGTC<br>TGCACTTACC ACCCAAGATG TTTACTCTTC ACTTTCACGG<br>CGGAATCACC ATCTGAGGAT CCCACCCGAT GGTTTACTTG<br>TGTCCTGAAA GACAGTGTTA CAGAAACACT GCCAAGAGTG<br>AATAGGACAG CAGCGATTTC TGGGTATTCT TTCAAGCAAT<br>GCTCACACCA AATAAGCGCT TGCAACAAAG ACATTTATGT<br>GGACCTAGAC ATGAAGGGCA TAAACTATAA CAGCTCAGTT<br>GCCAAGAGTG CTCAAGAATG CCAAGAAAGA TGCACGGATG<br>ACGTCCACTG CCACTTTTTC ACGTACGCCA CAAGGCAGTT<br>TCCCAGCCTG GAGCATCGTA ACATTTGTCT ACTGAAGCAC<br>ACCCAAACAG GGACACCAAC CAGAATAACG AAGCTCGATA<br>AAGTGGTGTC TGGATTTTCA CTGAAATCCT GTGCACTTTC<br>TAATCTGGCT TGTATTAGGG ACATTTTCCC TAATACGGTG<br>TTTGCAGACA GCAACATCGA CAGTGTCATG GCTCCCGATG<br>CTTTTGTCTG TGGCCGAATC TGCACTCATC ATCCCGGTTG<br>CTTGTTTTTT ACCTTCTTTT CCCAGGAATG GCCCAAAGAA<br>TCTCAAAGAA ATCTTTGTCT CCTTAAAACA TCTGAGAGTG<br>GATTGCCCAG TACACGCATT AAAAAGAGCA AAGCTCTTTC<br>TGGTTTCAGT CTACAAAGCT GCAGGCACAG CATCCCAGTG<br>TTCTGCCATT CTTCATTTTA CCATGACACT GATTTCTTGG<br>GAGAAGAACT GGATATTGTT GCTGCAAAAA GTCACGAGGC<br>CTGCCAGAAA CTGTGCACCA ATGCCGTCCG CTGCCAGTTT<br>TTTACCTATA CCCCAGCCCA AGCATCCTGC AACGAAGGGA<br>AGGGCAAGTG TTACTTAAAG CTTTCTTCAA ACGGATCTCC<br>AACTAAAATA CTTCACGGGA GAGGAGGCAT CTCTGGATAC<br>ACATTAAGGT TGTGTAAAAT GGATAATGAG TGTACCACCA<br>AAATCAAGCC CAGGATCGTT GGAGGAACTG CGTCTGTTCG<br>TGGTGAGTGG CCGTGGCAGG TGACCCTGCA CACAACCTCA<br>CCCACTCAGA GACACCTGTG TGGAGGCTCC ATCATTGGAA<br>ACCAGTGGAT ATTAACAGCC GCTCACTGTT TCTATGGGGT<br>AGAGTCACCT AAGATTTTGC GTGTCTACAG TGGCATTTTA<br>AATCAATCTG AAATAAAAGA GGACACATCT TTCTTTGGGG<br>TTCAAGAAAT AATAATCCAT GATCAGTATA AAATGGCAGA<br>AAGCGGGTAT GATATTGCCT TGTTGAAACT GGAAACCACA<br>GTGAATTACA CAGATTCTCA ACGACCCATA TGCCTGCCTT<br>CCAAAGGAGA TAGAAATGTA ATATACACTG ATTGCTGGGT<br>GACTGGATGG GGGTACAGAA AACTAAGAGA CAAAATACAA<br>AATACTCTCC AGAAAGCCAA GATACCCTTA GTGACCAACG<br>AAGAGTGCCA GAAGAGATAC AGAGGACATA AAATAACCCA<br>TAAGATGATC TGTGCCGGCT ACAGGGAAGG AGGGAAGGAC<br>GCTTGCAAGG GAGATTCGGG AGGCCCTCTG TCCTGCAAAC<br>ACAATGAGGT CTGGCATCTG GTAGGCATCA CGAGCTGGGG<br>CGAAGGCTGT GCTCAAAGGG AGCGGCCAGG TGTTTACACC<br>AACGTGGTCG AGTACGTGGA CTGGATTCTG GAGAAAACTC<br>AAGCAGTGTG AATGGGTTCC CAGGGGCCAT TGGAGTCCCT |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | GAAGGACCCA GGATTTGCTG GGAGAGGGTG TTGAGTTCAC TGTGCCAGCA TGCTTCCTCC ACAGTAACAC GCTGAAGGGG CTTGGTGTTT GTAAGAAAAT GCTAGAAGAA AACAAACTGT CACAAGTTGT TATGTCCAAA ACTCCCGTTC TATGATCGTT GTAGTTTGTT TGAGCATTCA GTCTCTTTGT TTTTGATCAC GCTTCTATGG AGTCCAAGAA TTACCATAAG GCAATATTTC TGAAGATTAC TATATAGGCA GATATAGCAG AAAATAACCA AGTAGTGGCA GTGGGGATCA GGCAGAAGAA CTGGTAAAAG AAGCCACCAT AAATAGATTT GTTCGATGAA AGATGAAAAC TGGAAGAAAG GAGAACAAAG ACAGTCTTCA CCATTTTGCA GGAATCTACA CTCTGCCTAT GTGAACACAT TTCTTTTGTA AAGAAAGAAA TTGATTGCAT TTAATGGCAG ATTTTCAGAA TAGTCAGGAA TTCTTGTCAT TTCCATTTTA AAATATATAT TAAAAAAAAT CAGTTCGAGT AGACACGAGC TAAGAGTGAA TGTGAAGATA ACAGAATTTC TGTGTGGAAG AGGATTACAA GCAGCAATTT ACCTGGAAGT GATACCTTAG GGGCAATCTT GAAGATACAC TTTCCTGAAA AATGATTTGT GATGGATTGT ATATTTATTT AAAATATCTT GGGAGGGGAG GCTGATGGAG ATAGGGAGCA TGCTCAAACC TCCCTAAGAC AAGCTGCTGC TGTGACTATG GGCTCCCAAA GAGCTAGATC GTATATTTAT TTGACAAAAA TCACCATAGA CTGCATCCAT ACTACAGAGA AAAAACAATT AGGGCGCAAA TGGATAGTTA CAGTAAAGTC TTCAGCAAGC AGCTGCCTGT ATTCTAAGCA CTGGGATTTT CTGTTTCGTG CAAATATTTA TCTCATTATT GTTGTGATCT AGTTCAATAA CCTAGAATTT GAATTGTCAC CACATAGCTT TCAATCTGTG CCAACAACTA TACAATTCAT CAAGTGTG |

NOV1401

| Sequence Description | SEQ ID NO: | Amino acid or polynucleotide sequence |
|---|---|---|
| HCDR1 (Combined) | 3 | GFTFSTAAMS |
| HCDR2 (Combined) | 4 | GISGSGSSTYYADSVKG |
| HCDR3 (Combined) | 5 | ELSYLYSGYYFDY |
| HCDR1 (Kabat) | 6 | TAAMS |
| HCDR2 (Kabat) | 4 | GISGSGSSTYYADSVKG |
| HCDR3 (Kabat) | 5 | ELSYLYSGYYFDY |
| HCDR1 (Chothia) | 7 | GFTFSTA |
| HCDR2 (Chothia) | 8 | SGSGSS |
| HCDR3 (Chothia) | 5 | ELSYLYSGYYFDY |
| HCDR1 (IMGT) | 9 | GFTFSTAA |
| HCDR2 (IMGT) | 10 | ISGSGSST |
| HCDR3 (IMGT) | 11 | ARELSYLYSGYYFDY |
| VH | 12 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSS |
| DNA encoding VH | 13 | CAGGTGCAGCTGCTGGAATCAGGCGGCGGACTGGTGCAGCCTG GCGGTAGCCTGAGACTGAGCTGCGCTGCTAGTGGCTTCACCTT TAGCACCGCCGCTATGAGCTGGGTTCGACAGGCCCCAGGGAAA GGCCTCGAGTGGGTCTCAGGGATTAGCGGTAGCGGCTCTAGCA CCTACTACGCCGATAGCGTGAAGGGCCGGTTCACTATCTCTAG GGATAACTCTAAGAACACCCTGTACCTGCAGATGAATAGCCTG AGAGCCGAGGACACCGCCGTCTACTACTGCGCTAGAGAGCTGA GCTACCTGTATAGCGGCTACTACTTCGACTACTGGGGTCAAGG CACCCTGGTCACCGTGTCTAGC |
| Heavy Chain | 14 | QVQLLESGGGLVQPGGSLRLSCAASGFTFSTAAMSWVRQAPGK GLEWVSGISGSGSSTYYADSVKGRFTISRDNSKNTLYLQMNSL RAEDTAVYYCARELSYLYSGYYFDYWGQGTLVTVSSASTKGPS VFPLAPSSKSTSGGTAALGCLVKDYFPEPVTVSWNSGALTSGV HTFPAVLQSSGLYSLSSVVTVPSSSLGTQTYICNVNHKPSNTK VDKRVEPKSCDKTHTCPPCPAPELLGGPSVFLFPPKPKDTLMI |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | SRIPEVICVVVAVSHEDPEVKFNWYVDGVEVHNAKTKPREEQY NSTYRVVSVLTVLHQDWLNGKEYKCKVSNKALAAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| DNA encoding Heavy Chain | 15 | CAGGTGCAGCTGCTGGAATCAGGCGGCGGACTGGTGCAGCCTG GCGGTAGCCTGAGACTGAGCTGCGCTGCTAGTGGCTTCACCTT TAGCACCGCCGCTATGAGCTGGGTTCGACAGGCCCCAGGGAAA GGCCTCGAGTGGGTCTCAGGGATTAGCGGTAGCGGCTCTAGCA CCTACTACGCCGATAGCGTGAAGGGCCGGTTCACTATCTCTAG GGATAACTCTAAGAACACCCTGTACCTGCAGATGAATAGCCTG AGAGCCGAGGACACCGCCGTCTACTACTGCGCTAGAGAGCTGA GCTACCTGTATAGCGGCTACTACTTCGACTACTGGGGTCAAGG CACCCTGGTCACCGTGTCTAGCGCTAGCACTAAGGGCCCCTCC GTGTTCCCTCTGGCCCCTTCCAGCAAGTCTACCTCCGGCGGCA CAGCTGCTCTGGGCTGCCTGGTCAAGGACTACTTCCCTGAGCC TGTGACAGTGTCCTGGAACTCTGGCGCCCTGACCTCTGGCGTG CACACCTTCCCTGCCGTGCTGCAGTCCTCCGGCCTGTACTCCC TGTCCTCCGTGGTCACAGTGCCTTCAAGCAGCCTGGGCACCCA GACCTATATCTGCAACGTGAACCACAAGCCTTCCAACACCAAG GTGGACAAGCGGGTGGAGCCTAAGTCCTGCGACAAGACCCACA CCTGTCCTCCCTGCCCTGCTCCTGAACTGCTGGGCGGCCCTTC TGTGTTCCTGTTCCCTCCAAAGCCCAAGGACACCCTGATGATC TCCCGGACCCCTGAAGTGACCTGCGTGGTGGTGGCCGTGTCCC ACGAGGATCCTGAAGTGAAGTTCAATTGGTACGTGGACGGCGT GGAGGTGCACAACGCCAAGACCAAGCCTCGGGAGGAACAGTAC AACTCCACCTACCGGGTGGTGTCCGTGCTGACCGTGCTGCACC AGGACTGGCTGAACGGCAAGGAGTACAAGTGCAAAGTCTCCAA CAAGGCCCTGGCCGCCCCTATCGAAAAGACAATCTCCAAGGCC AAGGGCCAGCCTAGGGAACCCCAGGTGTACACCCTGCCACCCA GCCGGGAGGAAATGACCAAGAACCAGGTGTCCCTGACCTGTCT GGTCAAGGGCTTCTACCCTTCCGATATCGCCGTGGAGTGGGAG TCTAACGGCCAGCCTGAGAACAACTACAAGACCACCCCTCCTG TGCTGGACTCCGACGGCTCCTTCTTCCTGTACTCCAAACTGAC CGTGGACAAGTCCCGGTGGCAGCAGGGCAACGTGTTCTCCTGC TCCGTGATGCACGAGGCCCTGCACAACCACTACACCCAGAAGT CCCTGTCCCTGTCTCCCGGCAAG |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 23 | QSVLIQPPSASGTPGQRVTISCSGSSSNIGSNDVSWYQQLPGT APKLLIYKNYNRPSGVPDRFSGSKSGTSASLAISGLQSEDEAD YYCSAWDQRQFDVVFGGGTKLTVL |
| DNA encoding VL | 24 | CAGTCAGTCCTGACTCAGCCCCCTAGCGCTAGTGGCACCCCTG GTCAAAGAGTGACTATTAGCTGTAGCGGCTCTAGCTCTAATAT CGGCTCTAACGACGTCAGCTGGTATCAGCAGCTGCCCGGCACC GCCCCTAAGCTGCTGATCTATAAGAACTATAATAGGCCTAGCG GCGTGCCCGATAGGTTTAGCGGGATCTAAATCAGGGACTTCTGC TAGTCTGGCTATTAGCGGCCTGCAGTCAGAGGACGAGGCCGAC |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | TACTACTGTAGCGCCTGGGATCAGCGTCAGTTCGACGTGGTGT<br>TCGGCGGAGGCACTAAGCTGACCGTGCTG |
| Light Chain | 25 | QSVLIQPPSASGTPGQRVTISCSGSSSNIGSNDVSWYQQLPGT<br>APKLLIYKNYNRPSGVPDRFSGSKSGTSASLAISGLQSEDEAD<br>YYCSAWDQRQFDVVFGGGTKLTVLGQPKAAPSVTLFPPSSEEL<br>QANKATLVCLISDFYPGAVIVAWKADSSPVKAGVETTIPSKQS<br>NNKYAASSYLSLIPEQWKSHRSYSCQVIHEGSTVEKTVAPTEC<br>S |
| DNA encoding Light Chain | 26 | CAGTCAGTCCTGACTCAGCCCCCTAGCGCTAGTGGCACCCCTG<br>GTCAAAGAGTGACTATTAGCTGTAGCGGCTCTAGCTCTAATAT<br>CGGCTCTAACGACGTCAGCTGGTATCAGCAGCTGCCCGGCACC<br>GCCCCTAAGCTGCTGATCTATAAGAACTATAATAGGCCTAGCG<br>GCGTGCCCGATAGGTTTAGCGGATCTAAATCAGGGACTTCTGC<br>TAGTCTGGCTATTAGCGGCCTGCAGTCAGAGGACGAGGCCGAC<br>TACTACTGTAGCGCCTGGGATCAGCGTCAGTTCGACGTGGTGT<br>TCGGCGGAGGCACTAAGCTGACCGTGCTGGGTCAACCTAAGGC<br>TGCCCCCAGCGTGACCCTGTTCCCCCCCAGCAGCGAGGAGCTG<br>CAGGCCAACAAGGCCACCCTGGTGTGCCTGATCAGCGACTTCT<br>ACCCCAGGCGCCGTGACCGTGGCCTGGAAGGCCGACAGCAGCCC<br>CGTGAAGGCCGGCGTGGAGACCACCACCCCCAGCAAGCAGAGC<br>AACAACAAGTACGCCGCCAGCAGCTACCTGAGCCTGACCCCCG<br>AGCAGTGGAAGAGCCACAGGTCCTACAGCTGCCAGGTGACCCA<br>CGAGGGCAGCACCGTGGAAAAGACCGTGGCCCCAACCGAGTGC<br>AGC |
| NOV1090 | | |
| HCDR1 (Combined) | 3 | GFTFSTAAMS |
| HCDR2 (Combined) | 4 | GISGSGSSTYYADSVKG |
| HCDR3 (Combined) | 5 | ELSYLYSGYYFDY |
| HCDR1 (Kabat) | 6 | TAAMS |
| HCDR2 (Kabat) | 4 | GISGSGSSTYYADSVKG |
| HCDR3 (Kabat) | 5 | ELSYLYSGYYFDY |
| HCDR1 (Chothia) | 7 | GFTFSTA |
| HCDR2 (Chothia) | 8 | SGSGSS |
| HCDR3 (Chothia) | 5 | ELSYLYSGYYFDY |
| HCDR1 (IMGT) | 9 | GFTFSTAA |
| HCDR2 (IMGT) | 10 | ISGSGSST |
| HCDR3 (IMGT) | 11 | ARELSYLYSGYYFDY |
| VH | 12 | QVQLLESGGGLVQPGGSLRLSCAASGFTFSTAAMSWVRQAPGK<br>GLEWVSGISGSGSSTYYADSVKGRFTISRDNSKNTLYLQMNSL<br>RAEDTAVYYCARELSYLYSGYYFDYWGQGTLVTVSS |
| DNA encoding VH | 69 | CAGGTGCAATTGCTGGAAAGCGGCGGTGGCCTGGTGCAGCCGG<br>GTGGCAGCCTGCGTCTGAGCTGCGCGGCGTCCGGATTCACCTT<br>TTCTACTGCTGCTATGTCTTGGGTGCGCCAGGCCCCGGGCAAA<br>GGTCTCGAGTGGGTTTCCGGTATCTCTGGTTCTGGTTCTTCTA<br>CCTACTATGCGGATAGCGTGAAAGGCCGCTTTACCATCAGCCG<br>CGATAATTCGAAAAACACCCTGTATCTGCAAATGAACAGCCTG<br>CGTGCGGAAGATACGGCCGTGTATTATTGCGCGCGTGAACTGT<br>CTTACCTGTACTCTGGTTACTACTTCGATTACTGGGGCCAAGG<br>CACCCTGGTGACTGTTAGCTCA |
| Heavy Chain | 62 | QVQLLESGGGLVQPGGSLRLSCAASGFTFSTAAMSWVRQAPGK<br>GLEWVSGISGSGSSTYYADSVKGRFTISRDNSKNTLYLQMNSL<br>RAEDTAVYYCARELSYLYSGYYFDYWGQGTLVTVSSASTKGPS<br>VFPLAPSSKSTSGGTAALGCLVKDYFPEPVTVSWNSGALTSGV<br>HTFPAVLQSSGLYSLSSVVTVPSSSLGTQTYICNVNHKPSNTK<br>VDKRVEPKSCDKTHTCPPCPAPEAAGGPSVFLFPPKPKDTLMI |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | SRIPEVICVVVDVSHEDPEVKFNWYVDGVEVHNAKTKPREEQY NSTYRVVSVLTVLHQDWLNGKEYKCKVSNKALPAPIEKTISKA KGQPREPQVYTLPPSREEMTKNQVSLTCLVKGFYPSDIAVEWE SNGQPENNYKTTPPVLDSDGSFFLYSKLTVDKSRWQQGNVFSC SVMHEALHNHYTQKSLSLSPGK |
| DNA encoding Heavy Chain | 63 | CAGGTGCAATTGCTGGAAAGCGGCGGTGGCCTGGTGCAGCCGG GTGGCAGCCTGCGTCTGAGCTGCGCGGCGTCCGGATTCACCTT TTCTACTGCTGCTATGTCTTGGGTGCGCCAGGCCCCGGGCAAA GGTCTCGAGTGGGTTTCCGGTATCTCTGGTTCTGTTCTTCTA CCTACTATGCGGATAGCGTGAAAGGCCGCTTTACCATCAGCCG CGATAATTCGAAAAACACCCTGTATCTGCAAATGAACAGCCTG CGTGCGGAAGATACGGCCGTGTATTATTGCGCGCGTGAACTGT CTTACCTGTACTCTGGTTACTACTTCGATTACTGGGGCCAAGG CACCCTGGTGACTGTTAGCTCAGCCTCCACCAAGGGTCCATCG GTCTTCCCCCTGGCACCCTCCTCCAAGAGCACCTCTGGGGGCA CAGCGGCCCTGGGCTGCCTGGTCAAGGACTACTTCCCCGAACC GGTGACGGTGTCGTGGAACTCAGGCGCCCTGACCAGCGGCGTG CACACCTTCCCGGCTGTCCTACAGTCCTCAGGACTCTACTCCC TCAGCAGCGTGGTGACCGTGCCCTCCAGCAGCTTGGGCACCCA GACCTACATCTGCAACGTGAATCACAAGCCCAGCAACACCAAG GTGGACAAGAGAGTTGAGCCCAAATCTTGTGACAAAACTCACA CATGCCCACCGTGCCCAGCACCTGAAGCAGCGGGGGGACCGTC AGTCTTCCTCTTCCCCCCAAAACCCAAGGACACCCTCATGATC TCCCGGACCCCTGAGGTCACATGCGTGGTGGTGGACGTGAGCC ACGAAGACCCTGAGGTCAAGTTCAACTGGTACGTGGACGGCGT GGAGGTGCATAATGCCAAGACAAAGCCGCGGGAGGAGCAGTAC AACAGCACGTACCGGGTGGTCAGCGTCCTCACCGTCCTGCACC AGGACTGGCTGAATGGCAAGGAGTACAAGTGCAAGGTCTCCAA CAAAGCCCTCCCAGCCCCCATCGAGAAAACCATCTCCAAAGCC AAAGGGCAGCCCCGAGAACCACAGGTGTACACCCTGCCCCCAT CCCGGGAGGAGATGACCAAGAACCAGGTCAGCCTGACCTGCCT GGTCAAAGGCTTCTATCCCAGCGACATCGCCGTGGAGTGGGAG AGCAATGGGCAGCCGGAGAACAACTACAAGACCACGCCTCCCG TGCTGGACTCCGACGGCTCCTTCTTCCTCTACAGCAAGCTCAC CGTGGACAAGAGCAGGTGGCAGCAGGGGAACGTCTTCTCATGC TCCGTGATGCATGAGGCTCTGCACAACCACTACACGCAGAAGA GCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 64 | DIVLIQPPSVSGAPGQRVTISCSGSSSNIGSNDVSWYQQLPGT APKLLIYKNYNRPSGVPDRFSGSKSGTSASLAITGLQAEDEAD YYCSAWDQRQFDVVFGGGTKLTVL |
| DNA encoding VL | 65 | GATATCGTGCTGACCCAGCCGCCGAGCGTGAGCGGTGCACCGG GCCAGCGCGTGACCATTAGCTGTAGCGGCAGCAGCAGCAACAT TGGTTCTAACGACGTGTCTTGGTACCAGCAGCTGCCGGGCACG GCGCCGAAACTGCTGATCTACAAAAACTACAACCGCCCGAGCG GCGTGCCGGATCGCTTTAGCGGATCCAAAAGCGGCACCAGCGC CAGCCTGGCGATTACCGGCCTGCAAGCAGAAGACGAAGCGGAT |

TABLE 1-continued

Examples of FXI/FXIa Antibodies, Fabs and FXI/FXIa Proteins

| Sequence Description | Sequence Identifier (SEQ ID NO:) | Amino acid or polynucleotide sequence |
|---|---|---|
| | | TATTACTGCTCTGCTTGGGACCAGCGTCAGTTCGACGTTGTGT TTGGCGGCGGCACGAAGTTAACCGTCCTA |
| Light Chain | 66 | DIVLIQPPSVSGAPGQRVTISCSGSSSNIGSNDVSWYQQLPGT APKLLIYKNYNRPSGVPDRFSGSKSGTSASLAITGLQAEDEAD YYCSAWDQRQFDVVFGGGTKLTVLGQPKAAPSVTLFPPSSEEL QANKATLVCLISDFYPGAVIVAWKADSSPVKAGVETTIPSKQS NNKYAASSYLSLIPEQWKSHRSYSCQVIHEGSTVEKTVAPTEC S |
| DNA encoding Light Chain | 67 | GATATCGTGCTGACCCAGCCGCCGAGCGTGAGCGGTGCACCGG GCCAGCGCGTGACCATTAGCTGTAGCGGCAGCAGCAGCAACAT TGGTTCTAACGACGTGTCTTGGTACCAGCAGCTGCCGGGCACG GCGCCGAAACTGCTGATCTACAAAAACTACAACCGCCCGAGCG GCGTGCCGGATCGCTTTAGCGGATCCAAAAGCGGCACCAGCGC CAGCCTGGCGATTACCGGCCTGCAAGCAGAAGACGAAGCGGAT TATTACTGCTCTGCTTGGGACCAGCGTCAGTTCGACGTTGTGT TTGGCGGCGGCACGAAGTTAACCGTCCTAGGTCAGCCCAAGGC TGCCCCCTCGGTCACTCTGTTCCCGCCCTCCTCTGAGGAGCTT CAAGCCAACAAGGCCACACTGGTGTGTCTCATAAGTGACTTCT ACCCGGGAGCCGTGACAGTGGCCTGGAAGGCAGATAGCAGCCC CGTCAAGGCGGGAGTGGAGACCACCACACCCTCCAAACAAAGC AACAACAAGTACGCGGCCAGCAGCTATCTGAGCCTGACGCCTG AGCAGTGGAAGTCCCACAGAAGCTACAGCTGCCAGGTCACGCA TGAAGGGAGCACCGTGGAGAAGACAGTGGCCCCTACAGAATGT TCA |

TABLE 2

Examples of FXI/FXIa Antibodies and Fabs

| | SEQ ID NO: | |
|---|---|---|
| AM1 | | |
| HCDR1 (Combined) | 3 | GFTFSTAAMS |
| HCDR2 (Combined) | 27 | TIDSWGDDTDYADSVKG |
| HCDR3 (Combined) | 5 | ELSYLYSGYYFDY |
| HCDR1 (Kabat) | 6 | TAAMS |
| HCDR2 (Kabat) | 27 | TIDSWGDDTDYADSVKG |
| HCDR3 (Kabat) | 5 | ELSYLYSGYYFDY |
| HCDR1 (Chothia) | 7 | GFTFSTA |
| HCDR2 (Chothia) | 28 | DSWGDD |
| HCDR3 (Chothia) | 5 | ELSYLYSGYYFDY |
| HCDR1 (IMGT) | 9 | GFTFSTAA |
| HCDR2 (IMGT) | 29 | IDSWGDDT |
| HCDR3 (IMGT) | 11 | ARELSYLYSGYYFDY |
| VH | 30 | QVQLLESGGGLVQPGGSLRLSCAASGFTFSTAAMSW VRQAPGKGLEWVSTIDSWGDDTDYADSVKGRFTISR DNSKNTLYLQMNSLRAEDTAVYYCARELSYLYSGYY FDYWGQGTLVTVSS |
| DNA VH | 31 | CAGGTGCAATTGCTGGAAAGCGGCGGTGGCCTGGTG CAGCCGGGTGGCAGCCTGCGTCTGAGCTGCGCGGCG TCCGGATTCACCTTTTCTACTGCTGCTATGTCTTGG GTGCGCCAGGCCCCGGGCAAAGGTCTCGAGTGGGTT TCCACTATCGACTCTTGGGGCGACGACACTGACTAT |

TABLE 2-continued

Examples of FXI/FXIa Antibodies and Fabs

| | SEQ ID NO: | |
|---|---|---|
| | | GCGGATAGCGTGAAAGGCCGCTTTACCATCAGCCGC GATAATTCGAAAAACACCCTGTATCTGCAAATGAAC AGCCTGCGTGCGGAAGATACGGCCGTGTATTATTGC GCGCGTGAACTGTCTTACCTGTACTCTGGTTACTAC TTCGATTACTGGGGCCAAGGCACCCTGGTGACTGTT AGCTCA |
| Heavy Chain | 32 | QVQLLESGGGLVQPGGSLRLSCAASGFTFSTAAMSW VRQAPGKGLEWVSTIDSWGDDTDYADSVKGRFTISR DNSKNTLYLQMNSLRAEDTAVYYCARELSYLYSGYY FDYWGQGTLVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKV DKRVEPKSCDKTHTCPPCPAPEAAGGPSVFLFPPKP KDTLMISRTPEVTCVVVDVSHEDPEVKFNWYVDGVE VHNAKTKPREEQYNSTYRVVSVLTVLHQDWLNGKEY KCKVSNKALPAPIEKTISKAKGQPREPQVYTLPPSR EEMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| DNA Heavy Chain | 33 | CAGGTGCAATTGCTGGAAAGCGGCGGTGGCCTGGTG CAGCCGGGTGGCAGCCTGCGTCTGAGCTGCGCGGCG TCCGGATTCACCTTTTCTACTGCTGCTATGTCTTGG GTGCGCCAGGCCCCGGGCAAAGGTCTCGAGTGGGTT TCCACTATCGACTCTTGGGGCGACGACACTGACTAT GCGGATAGCGTGAAAGGCCGCTTTACCATCAGCCGC GATAATTCGAAAAACACCCTGTATCTGCAAATGAAC AGCCTGCGTGCGGAAGATACGGCCGTGTATTATTGC GCGCGTGAACTGTCTTACCTGTACTCTGGTTACTAC TTCGATTACTGGGGCCAAGGCACCCTGGTGACTGTT AGCTCAGCCTCCACCAAGGGTCCATCGGTCTTCCCC CTGGCACCCTCCTCCAAGAGCACCTCTGGGGGCACA GCGGCCCTGGGCTGCCTGGTCAAGGACTACTTCCCC GAACCGGTGACGGTGTCGTGGAACTCAGGCGCCCTG ACCAGCGGCGTGCACACCTTCCCGGCTGTCCTACAG TCCTCAGGACTCTACTCCCTCAGCAGCGTGGTGACC GTGCCCTCCAGCAGCTTGGGCACCCAGACCTACATC TGCAACGTGAATCACAAGCCCAGCAACACCAAGGTG GACAAGAGAGTTGAGCCCAAATCTTGTGACAAAACT CACACATGCCCACCGTGCCCAGCACCTGAAGCAGCG GGGGGACCGTCAGTCTTCCTCTTCCCCCCAAAACCC AAGGACACCCTCATGATCTCCCGGACCCCTGAGGTC ACATGCGTGGTGGTGGACGTGAGCCACGAAGACCCT GAGGTCAAGTTCAACTGGTACGTGGACGGCGTGGAG GTGCATAATGCCAAGACAAAGCCGCGGGAGGAGCAG TACAACAGCACGTACCGGGTGGTCAGCGTCCTCACC GTCCTGCACCAGGACTGGCTGAATGGCAAGGAGTAC AAGTGCAAGGTCTCCAACAAAGCCCTCCCAGCCCCC ATCGAGAAAACCATCTCCAAAGCCAAAGGGCAGCCC CGAGAACCACAGGTGTACACCCTGCCCCCATCCCGG GAGGAGATGACCAAGAACCAGGTCAGCCTGACCTGC CTGGTCAAAGGCTTCTATCCCAGCGACATCGCCGTG GAGTGGGAGAGCAATGGGCAGCCGGAGAACAACTAC AAGACCACGCCTCCCGTGCTGGACTCCGACGGCTCC TTCTTCCTCTACAGCAAGCTCACCGTGGACAAGAGC AGGTGGCAGCAGGGGAACGTCTTCTCATGCTCCGTG ATGCATGAGGCTCTGCACAACCACTACACGCAGAAG AGCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |

TABLE 2-continued

Examples of FXI/FXIa Antibodies and Fabs

| | SEQ ID NO: | |
|---|---|---|
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 34 | DIVLTQPPSVSGAPGQRVTISCSGSSSNIGSNDVSW YQQLPGTAPKLLIYKNYNRPSGVPDRFSGSKSGTSA SLAITGLQAEDEADYYCSAWDQRQFDVVFGGGTKLT VL |
| DNA VL | 35 | GATATCGTGCTGACCCAGCCGCCGAGCGTGAGCGGT GCACCGGGCCAGCGCGTGACCATTAGCTGTAGCGGT AGCAGCAGCAACATTGGTTCTAACGACGTGTCTTGG TACCAGCAGCTGCCGGGCACGGCGCCGAAACTGCTG ATCTACAAAAACTACAACCGCCCGAGCGGCGTGCCG GATCGCTTTAGCGGATCCAAAAGCGGCACCAGCGCC AGCCTGGCGATTACCGGCCTGCAAGCAGAAGACGAA GCGGATTATTACTGCTCTGCTTGGGACCAGCGTCAG TTCGACGTTGTGTTTGGCGGCGGCACGAAGTTAACC GTCCTA |
| Light Chain | 36 | DIVLTQPPSVSGAPGQRVTISCSGSSSNIGSNDVSW YQQLPGTAPKLLIYKNYNRPSGVPDRFSGSKSGTSA SLAITGLQAEDEADYYCSAWDQRQFDVVFGGGTKLT VLGQPKAAPSVTLFPPSSEELQANKATLVCLISDFY PGAVTVAWKADSSPVKAGVETTTPSKQSNNKYAASS YLSLTPEQWKSHRSYSCQVTHEGSTVEKTVAPTECS |
| DNA Light Chain | 37 | GATATCGTGCTGACCCAGCCGCCGAGCGTGAGCGGT GCACCGGGCCAGCGCGTGACCATTAGCTGTAGCGGC AGCAGCAGCAACATTGGTTCTAACGACGTGTCTTGG TACCAGCAGCTGCCGGGCACGGCGCCGAAACTGCTG ATCTACAAAAACTACAACCGCCCGAGCGGCGTGCCG GATCGCTTTAGCGGATCCAAAAGCGGCACCAGCGCC AGCCTGGCGATTACCGGCCTGCAAGCAGAAGACGAA GCGGATTATTACTGCTCTGCTTGGGACCAGCGTCAG TTCGACGTTGTGTTTGGCGGCGGCACGAAGTTAACC GTCCTAGGTCAGCCCAAGGCTGCCCCCTCGGTCACT CTGTTCCCGCCCTCCTCTGAGGAGCTTCAAGCCAAC AAGGCCACACTGGTGTGTCTCATAAGTGACTTCTAC CCGGGAGCCGTGACAGTGGCCTGGAAGGCAGATAGC AGCCCCGTCAAGGCGGGAGTGGAGACCACCACACCC TCCAAACAAAGCAACAACAAGTACGCGGCCAGCAGC TATCTGAGCCTGACGCCTGAGCAGTGGAAGTCCCAC AGAAGCTACAGCTGCCAGGTCACGCATGAAGGGAGC ACCGTGGAGAAGACAGTGGCCCCTACAGAATGTTCA |
| AM2 | | |
| HCDR1 (Combined) | 3 | GFTFSTAAMS |
| HCDR2 (Combined) | 38 | SIEYYDTDTHYADSVKG |
| HCDR3 (Combined) | 5 | ELSYLYSGYYFDY |
| HCDR1 (Kabat) | 6 | TAAMS |
| HCDR2 (Kabat) | 38 | SIEYYDTDTHYADSVKG |
| HCDR3 (Kabat) | 5 | ELSYLYSGYYFDY |
| HCDR1 (Chothia) | 7 | GFTFSTA |
| HCDR2 (Chothia) | 39 | EYYDTD |
| HCDR3 (Chothia) | 5 | ELSYLYSGYYFDY |

TABLE 2-continued

Examples of FXI/FXIa Antibodies and Fabs

| | SEQ ID NO: | |
|---|---|---|
| HCDR1 (IMGT) | 9 | GFTFSTAA |
| HCDR2 (IMGT) | 40 | IEYYDTDT |
| HCDR3 (IMGT) | 11 | ARELSYLYSGYYFDY |
| VH | 41 | QVQLLESGGGLVQPGGSLRLSCAASGFTFSTAAMSW<br>VRQAPGKGLEWVSSIEYYDTDTHYADSVKGRFTISR<br>DNSKNTLYLQMNSLRAEDTAVYYCARELSYLYSGYY<br>FDYWGQGTLVTVSS |
| DNA VH | 42 | CAGGTGCAATTGCTGGAAAGCGGCGGTGGCCTGGTG<br>CAGCCGGGTGGCAGCCTGCGTCTGAGCTGCGCGGCG<br>TCCGGATTCACCTTTTCTACTGCTGCTATGTCTTGG<br>GTGCGCCAGGCCCCGGGCAAAGGTCTCGAGTGGGTT<br>TCCTCTATCGAATACTACGACACTGACACTCATTAT<br>GCGGATAGCGTGAAAGGCCGCTTTACCATCAGCCGC<br>GATAATTCGAAAAACACCCTGTATCTGCAAATGAAC<br>AGCCTGCGTGCGGAAGATACGGCCGTGTATTATTGC<br>GCGCGTGAACTGTCTTACCTGTACTCTGGTTACTAC<br>TTCGATTACTGGGGCCAAGGCACCCTGGTGACTGTT<br>AGCTCA |
| Heavy Chain | 43 | QVQLLESGGGLVQPGGSLRLSCAASGFTFSTAAMSW<br>VRQAPGKGLEWVSSIEYYDTDTHYADSVKGRFTISR<br>DNSKNTLYLQMNSLRAEDTAVYYCARELSYLYSGYY<br>FDYWGQGTLVTVSSASTKGPSVFPLAPSSKSTSGGT<br>AALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAPEAAGGPSVFLFPPKP<br>KDTLMISRTPEVTCVVVDVSHEDPEVKFNWYVDGVE<br>VHNAKTKPREEQYNSTYRVVSVLTVLHQDWLNGKEY<br>KCKVSNKALPAPIEKTISKAKGQPREPQVYTLPPSR<br>EEMTKNQVSLTCLVKGFYPSDIAVEWESNGQPENNY<br>KTTPPVLDSDGSFFLYSKLTVDKSRWQQGNVFSCSV<br>MHEALHNHYTQKSLSLSPGK |
| DNA Heavy Chain | 44 | CAGGTGCAATTGCTGGAAAGCGGCGGTGGCCTGGTG<br>CAGCCGGGTGGCAGCCTGCGTCTGAGCTGCGCGGCG<br>TCCGGATTCACCTTTTCTACTGCTGCTATGTCTTGG<br>GTGCGCCAGGCCCCGGGCAAAGGTCTCGAGTGGGTT<br>TCCTCTATCGAATACTACGACACTGACACTCATTAT<br>GCGGATAGCGTGAAAGGCCGCTTTACCATCAGCCGC<br>GATAATTCGAAAAACACCCTGTATCTGCAAATGAAC<br>AGCCTGCGTGCGGAAGATACGGCCGTGTATTATTGC<br>GCGCGTGAACTGTCTTACCTGTACTCTGGTTACTAC<br>TTCGATTACTGGGGCCAAGGCACCCTGGTGACTGTT<br>AGCTCAGCCTCCACCAAGGGTCCATCGGTCTTCCCC<br>CTGGCACCCTCCTCCAAGAGCACCTCTGGGGGCACA<br>GCGGCCCTGGGCTGCCTGGTCAAGGACTACTTCCCC<br>GAACCGGTGACGGTGTCGTGGAACTCAGGCGCCCTG<br>ACCAGCGGCGTGCACACCTTCCCGGCTGTCCTACAG<br>TCCTCAGGACTCTACTCCCTCAGCAGCGTGGTGACC<br>GTGCCCTCCAGCAGCTTGGGCACCCAGACCTACATC<br>TGCAACGTGAATCACAAGCCCAGCAACACCAAGGTG<br>GACAAGAGAGTTGAGCCCAAATCTTGTGACAAAACT<br>CACACATGCCCACCGTGCCCAGCACCTGAAGCAGCG<br>GGGGGACCGTCAGTCTTCCTCTTCCCCCCAAAACCC<br>AAGGACACCCTCATGATCTCCCGGACCCCTGAGGTC<br>ACATGCGTGGTGGTGGACGTGAGCCACGAAGACCCT<br>GAGGTCAAGTTCAACTGGTACGTGGACGGCGTGGAG<br>GTGCATAATGCCAAGACAAAGCCGCGGGAGGAGCAG<br>TACAACAGCACGTACCGGGTGGTCAGCGTCCTCACC<br>GTCCTGCACCAGGACTGGCTGAATGGCAAGGAGTAC<br>AAGTGCAAGGTCTCCAACAAAGCCCTCCCAGCCCCC<br>ATCGAGAAAACCATCTCCAAAGCCAAAGGGCAGCCC<br>CGAGAACCACAGGTGTACACCCTGCCCCCATCCCGG<br>GAGGAGATGACCAAGAACCAGGTCAGCCTGACCTGC<br>CTGGTCAAAGGCTTCTATCCCAGCGACATCGCCGTG<br>GAGTGGGAGAGCAATGGGCAGCCGGAGAACAACTAC<br>AAGACCACGCCTCCCGTGCTGGACTCCGACGGCTCC |

TABLE 2-continued

Examples of FXI/FXIa Antibodies and Fabs

| | SEQ ID NO: | |
|---|---|---|
| | | TTCTTCCTCTACAGCAAGCTCACCGTGGACAAGAGC AGGTGGCAGCAGGGGAACGTCTTCTCATGCTCCGTG ATGCATGAGGCTCTGCACAACCACTACACGCAGAAG AGCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 34 | DIVLTQPPSVSGAPGQRVTISCSGSSSNIGSNDVSW YQQLPGTAPKLLIYKNYNRPSGVPDRFSGSKSGTSA SLAITGLQAEDEADYYCSAWDQRQFDVVFGGGTKLT VL |
| DNA VL | 35 | GATATCGTGCTGACCCAGCCGCCGAGCGTGAGCGGT GCACCGGGCCAGCGCGTGACCATTAGCTGTAGCGGC AGCAGCAGCAACATTGGTTCTAACGACGTGTCTTGG TACCAGCAGCTGCCGGGCACGGCGCCGAAACTGCTG ATCTACAAAAACTACAACCGCCCGAGCGGCGTGCCG GATCGCTTTAGCGGATCCAAAAGCGGCACCAGCGCC AGCCTGGCGATTACCGGCCTGCAAGCAGAAGACGAA GCGGATTATTACTGCTCTGCTTGGGACCAGCGTCAG TTCGACGTTGTGTTTGGCGGCGGCACGAAGTTAACC GTCCTA |
| Light Chain | 36 | DIVLTQPPSVSGAPGQRVTISCSGSSSNIGSNDVSW YQQLPGTAPKLLIYKNYNRPSGVPDRFSGSKSGTSA SLAITGLQAEDEADYYCSAWDQRQFDVVFGGGTKLT VLGQPKAAPSVTLFPPSSEELQANKATLVCLISDFY PGAVTVAWKADSSPVKAGVETTTPSKQSNNKYAASS YLSLTPEQWKSHRSYSCQVTHEGSTVEKTVAPTECS |
| DNA Light Chain | 37 | GATATCGTGCTGACCCAGCCGCCGAGCGTGAGCGGT GCACCGGGCCAGCGCGTGACCATTAGCTGTAGCGGC AGCAGCAGCAACATTGGTTCTAACGACGTGTCTTGG TACCAGCAGCTGCCGGGCACGGCGCCGAAACTGCTG ATCTACAAAAACTACAACCGCCCGAGCGGCGTGCCG GATCGCTTTAGCGGATCCAAAAGCGGCACCAGCGCC AGCCTGGCGATTACCGGCCTGCAAGCAGAAGACGAA GCGGATTATTACTGCTCTGCTTGGGACCAGCGTCAG TTCGACGTTGTGTTTGGCGGCGGCACGAAGTTAACC GTCCTAGGTCAGCCCAAGGCTGCCCCCTCGGTCACT CTGTTCCCGCCCTCCTCTGAGGAGCTTCAAGCCAAC AAGGCCACACTGGTGTGTCTCATAAGTGACTTCTAC CCGGGAGCCGTGACAGTGGCCTGGAAGGCAGATAGC AGCCCCGTCAAGGCGGGAGTGGAGACCACCACACCC TCCAAACAAAGCAACAACAAGTACGCGGCCAGCAGC TATCTGAGCCTGACGCCTGAGCAGTGGAAGTCCCAC AGAAGCTACAGCTGCCAGGTCACGCATGAAGGGAGC ACCGTGGAGAAGACAGTGGCCCCTACAGAATGTTCA |

TABLE 2-continued

Examples of FXI/FXIa Antibodies and Fabs

| | SEQ ID NO: | |
|---|---|---|
| AM3 | | |
| HCDR1 (Combined) | 3 | GFTFSTAAMS |
| HCDR2 (Combined) | 45 | TIEYSSQETYYADSVKG |
| HCDR3 (Combined) | 5 | ELSYLYSGYYFDY |
| HCDR1 (Kabat) | 6 | TAAMS |
| HCDR2 (Kabat) | 45 | TIEYSSQETYYADSVKG |
| HCDR3 (Kabat) | 5 | ELSYLYSGYYFDY |
| HCDR1 (Chothia) | 7 | GFTFSTA |
| HCDR2 (Chothia) | 46 | EYSSQE |
| HCDR3 (Chothia) | 5 | ELSYLYSGYYFDY |
| HCDR1 (IMGT) | 9 | GFTFSTAA |
| HCDR2 (IMGT) | 47 | IEYSSQET |
| HCDR3 (IMGT) | 11 | ARELSYLYSGYYFDY |
| VH | 48 | QVQLLESGGGLVQPGGSLRLSCAASGFTFSTAAMSW VRQAPGKGLEWVSTIEYSSQETYYADSVKGRFTISR DNSKNTLYLQMNSLRAEDTAVYYCARELSYLYSGYY FDYWGQGTLVTVSS |
| DNA VH | 49 | CAGGTGCAATTGCTGGAAAGCGGCGGTGGCCTGGTG CAGCCGGGTGGCAGCCTGCGTCTGAGCTGCGCGGCG TCCGGATTCACCTTTTCTACTGCTGCTATGTCTTGG GTGCGCCAGGCCCCGGGCAAAGGTCTCGAGTGGGTT TCCACTATCGAATACTCTAGCCAGGAAACTTACTAT GCGGATAGCGTGAAAGGCCGCTTTACCATCAGCCGC GATAATTCGAAAAACACCCTGTATCTGCAAATGAAC AGCCTGCGTGCGGAAGATACGGCCGTGTATTATTGC GCGCGTGAACTGTCTTACCTGTACTCTGGTTACTAC TTCGATTACTGGGGCCAAGGCACCCTGGTGACTGTT AGCTCA |
| Heavy Chain | 50 | QVQLLESGGGLVQPGGSLRLSCAASGFTFSTAAMSW VRQAPGKGLEWVSTIEYSSQETYYADSVKGRFTISR DNSKNTLYLQMNSLRAEDTAVYYCARELSYLYSGYY FDYWGQGTLVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKV DKRVEPKSCDKTHTCPPCPAPEAAGGPSVFLFPPKP KDTLMISRTPEVTCVVVDVSHEDPEVKFNWYVDGVE VHNAKTKPREEQYNSTYRVVSVLTVLHQDWLNGKEY KCKVSNKALPAPIEKTISKAKGQPREPQVYTLPPSR EEMTKNQVSLTCLVKGFYPSDIAVEWESNGQPENNY KTTPPVLDSDGSFFLYSKLTVDKSRWQQGNVFSCSV MHEALHNHYTQKSLSLSPGK |
| DNA Heavy Chain | 51 | CAGGTGCAATTGCTGGAAAGCGGCGGTGGCCTGGTG CAGCCGGGTGGCAGCCTGCGTCTGAGCTGCGCGGCG TCCGGATTCACCTTTTCTACTGCTGCTATGTCTTGG GTGCGCCAGGCCCCGGGCAAAGGTCTCGAGTGGGTT TCCACTATCGAATACTCTAGCCAGGAAACTTACTAT GCGGATAGCGTGAAAGGCCGCTTTACCATCAGCCGC GATAATTCGAAAAACACCCTGTATCTGCAAATGAAC AGCCTGCGTGCGGAAGATACGGCCGTGTATTATTGC GCGCGTGAACTGTCTTACCTGTACTCTGGTTACTAC TTCGATTACTGGGGCCAAGGCACCCTGGTGACTGTT AGCTCAGCCTCCACCAAGGGTCCATCGGTCTTCCCC CTGGCACCCTCCTCCAAGAGCACCTCTGGGGGCACA GCGGCCCTGGGCTGCCTGGTCAAGGACTACTTCCCC GAACCGGTGACGGTGTCGTGGAACTCAGGCGCCCTG ACCAGCGGCGTGCACACCTTCCCGGCTGTCCTACAG TCCTCAGGACTCTACTCCCTCAGCAGCGTGGTGACC GTGCCCTCCAGCAGCTTGGGCACCCAGACCTACATC |

TABLE 2-continued

Examples of FXI/FXIa Antibodies and Fabs

| | SEQ ID NO: | |
|---|---|---|
| | | TGCAACGTGAATCACAAGCCCAGCAACACCAAGGTG
GACAAGAGAGTTGAGCCCAAATCTTGTGACAAAACT
CACACATGCCCACCGTGCCCAGCACCTGAAGCAGCG
GGGGGACCGTCAGTCTTCCTCTTCCCCCCAAAACCC
AAGGACACCCTCATGATCTCCCGGACCCCTGAGGTC
ACATGCGTGGTGGTGGACGTGAGCCACGAAGACCCT
GAGGTCAAGTTCAACTGGTACGTGGACGGCGTGGAG
GTGCATAATGCCAAGACAAAGCCGCGGGAGGAGCAG
TACAACAGCACGTACCGGGTGGTCAGCGTCCTCACC
GTCCTGCACCAGGACTGGCTGAATGGCAAGGAGTAC
AAGTGCAAGGTCTCCAACAAAGCCCTCCCAGCCCCC
ATCGAGAAAACCATCTCCAAAGCCAAAGGGCAGCCC
CGAGAACCACAGGTGTACACCCTGCCCCCATCCCGG
GAGGAGATGACCAAGAACCAGGTCAGCCTGACCTGC
CTGGTCAAAGGCTTCTATCCCAGCGACATCGCCGTG
GAGTGGGAGAGCAATGGGCAGCCGGAGAACAACTAC
AAGACCACGCCTCCCGTGCTGGACTCCGACGGCTCC
TTCTTCCTCTACAGCAAGCTCACCGTGGACAAGAGC
AGGTGGCAGCAGGGGAACGTCTTCTCATGCTCCGTG
ATGCATGAGGCTCTGCACAACCACTACACGCAGAAG
AGCCTCTCCCTGTCTCCGGGTAAA |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 34 | DIVLTQPPSVSGAPGQRVTISCSGSSSNIGSNDVSW
YQQLPGTAPKLLIYKNYNRPSGVPDRFSGSKSGTSA
SLAITGLQAEDEADYYCSAWDQRQFDVVFGGGTKLT
VL |
| DNA VL | 35 | GATATCGTGCTGACCCAGCCGCCGAGCGTGAGCGGT
GCACCGGGCCAGCGCGTGACCATTAGCTGTAGCGGC
AGCAGCAGCAACATTGGTTCTAACGACGTGTCTTGG
TACCAGCAGCTGCCGGGCACGGCGCCGAAACTGCTG
ATCTACAAAAACTACAACCGCCCGAGCGGCGTGCCG
GATCGCTTTAGCGGATCCAAAAGCGGCACCAGCGCC
AGCCTGGCGATTACCGGCCTGCAAGCAGAAGACGAA
GCGGATTATTACTGCTCTGCTTGGGACCAGCGTCAG
TTCGACGTTGTGTTTGGCGGCGGCACGAAGTTAACC
GTCCTA |
| Light Chain | 36 | DIVLTQPPSVSGAPGQRVTISCSGSSSNIGSNDVSW
YQQLPGTAPKLLIYKNYNRPSGVPDRFSGSKSGTSA
SLAITGLQAEDEADYYCSAWDQRQFDVVFGGGTKLT
VLGQPKAAPSVTLFPPSSEELQANKATLVCLISDFY
PGAVTVAWKADSSPVKAGVETTTPSKQSNNKYAASS
YLSLTPEQWKSHRSYSCQVTHEGSTVEKTVAPTECS |
| DNA Light Chain | 37 | GATATCGTGCTGACCCAGCCGCCGAGCGTGAGCGGT
GCACCGGGCCAGCGCGTGACCATTAGCTGTAGCGGC
AGCAGCAGCAACATTGGTTCTAACGACGTGTCTTGG
TACCAGCAGCTGCCGGGCACGGCGCCGAAACTGCTG
ATCTACAAAAACTACAACCGCCCGAGCGGCGTGCCG
GATCGCTTTAGCGGATCCAAAAGCGGCACCAGCGCC |

TABLE 2-continued

Examples of FXI/FXIa Antibodies and Fabs

| | SEQ ID NO: | |
|---|---|---|
| | | AGCCTGGCGATTACCGGCCTGCAAGCAGAAGACGAA
GCGGATTATTACTGCTCTGCTTGGGACCAGCGTCAG
TTCGACGTTGTGTTTGGCGGCGGCACGAAGTTAACC
GTCCTAGGTCAGCCCAAGGCTGCCCCCTCGGTCACT
CTGTTCCCGCCCTCCTCTGAGGAGCTTCAAGCCAAC
AAGGCCACACTGGTGTGTCTCATAAGTGACTTCTAC
CCGGGAGCCGTGACAGTGGCCTGGAAGGCAGATAGC
AGCCCCGTCAAGGCGGGAGTGGAGACCACCACACCC
TCCAAACAAAGCAACAACAAGTACGCGGCCAGCAGC
TATCTGAGCCTGACGCCTGAGCAGTGGAAGTCCCAC
AGAAGCTACAGCTGCCAGGTCACGCATGAAGGGAGC
ACCGTGGAGAAGACAGTGGCCCCTACAGAATGTTCA |
| AM4 | | |
| HCDR1 (Combined) | 3 | GFTFSTAAMS |
| HCDR2 (Combined) | 45 | TIEYSSQETYYADSVKG |
| HCDR3 (Combined) | 5 | ELSYLYSGYYFDY |
| HCDR1 (Kabat) | 6 | TAAMS |
| HCDR2 (Kabat) | 45 | TIEYSSQETYYADSVKG |
| HCDR3 (Kabat) | 5 | ELSYLYSGYYFDY |
| HCDR1 (Chothia) | 7 | GFTFSTA |
| HCDR2 (Chothia) | 46 | EYSSQE |
| HCDR3 (Chothia) | 5 | ELSYLYSGYYFDY |
| HCDR1 (IMGT) | 9 | GFTFSTAA |
| HCDR2 (IMGT) | 47 | IEYSSQET |
| HCDR3 (IMGT) | 11 | ARELSYLYSGYYFDY |
| VH | 48 | QVQLLESGGGLVQPGGSLRLSCAASGFTFSTAAMSW
VRQAPGKGLEWVSTIEYSSQETYYADSVKGRFTISR
DNSKNTLYLQMNSLRAEDTAVYYCARELSYLYSGYY
FDYWGQGTLVTVSS |
| DNA VH | 52 | CAAGTGCAGCTGCTTGAATCTGGCGGCGGACTGGTG
CAGCCTGGCGGCTCCCTGAGACTGTCTTGCGCCGCC
TCCGGCTTCACCTTCTCCACCGCCGCTATGTCCTGG
GTCCGACAGGCTCCCGGCAAGGGCCTGGAATGGGTG
TCCACCATTGAGTACTCCAGCCAGGAAACCTACTAC
GCCGACTCCGTGAAGGGCCGGTTCACCATCTCCCGG
GACAACTCCAAGAACACCCTGTACCTGCAGATGAAC
TCCCTGCGGGCCGAGGACACCGCCGTGTACTACTGC
GCCAGAGAGCTGTCCTACCTGTACTCCGGCTACTAC
TTCGACTACTGGGGCCAGGGCACCCTGGTCACCGTG
TCCTCT |
| Heavy Chain | 53 | QVQLLESGGGLVQPGGSLRLSCAASGFTFSTAAMSW
VRQAPGKGLEWVSTIEYSSQETYYADSVKGRFTISR
DNSKNTLYLQMNSLRAEDTAVYYCARELSYLYSGYY
FDYWGQGTLVTVSSASTKGPSVFPLAPSSKSTSGGT
AALGCLVKDYFPEPVTVSWNSGALTSGVHTFPAVLQ
SSGLYSLSSVVTVPSSSLGTQTYICNVNHKPSNTKV
DKRVEPKSCDKTHTCPPCPAPEAAGGPSVFLFPPKP
KDTLMISRTPEVTCVVVDVSHEDPEVKFNWYVDGVE
VHNAKTKPREEQYNSTYRVVSVLTVLHQDWLNGKEY
KCKVSNKALPAPIEKTISKAKGQPREPQVYTLPPSR
EEMTKNQVSLTCLVKGFYPSDIAVEWESNGQPENNY
KTTPPVLDSDGSFFLYSKLTVDKSRWQQGNVFSCSV
MHEALHNHYTQKSLSLSPGK |
| DNA Heavy Chain | 54 | CAAGTGCAGCTGCTTGAATCTGGCGGCGGACTGGTG
CAGCCTGGCGGCTCCCTGAGACTGTCTTGCGCCGCC
TCCGGCTTCACCTTCTCCACCGCCGCTATGTCCTGG
GTCCGACAGGCTCCCGGCAAGGGCCTGGAATGGGTG
TCCACCATTGAGTACTCCAGCCAGGAAACCTACTAC |

TABLE 2-continued

Examples of FXI/FXIa Antibodies and Fabs

| | SEQ ID NO: | |
|---|---|---|
| | | GCCGACTCCGTGAAGGGCCGGTTCACCATCTCCCGG
GACAACTCCAAGAACACCCTGTACCTGCAGATGAAC
TCCCTGCGGGCCGAGGACACCGCCGTGTACTACTGC
GCCAGAGAGCTGTCCTACCTGTACTCCGGCTACTAC
TTCGACTACTGGGGCCAGGGCACCCTGGTCACCGTG
TCCTCTGCTAGCACCAAGGGCCCCTCCGTGTTCCCT
CTGGCCCCTTCCAGCAAGTCTACCTCCGGCGGCACA
GCTGCTCTGGGCTGCCTGGTCAAGGACTACTTCCCT
GAGCCTGTGACAGTGTCCTGGAACTCTGGCGCCCTG
ACCTCTGGCGTGCACACCTTCCCTGCCGTGCTGCAG
TCCTCCGGCCTGTACTCCCTGTCCTCCGTGGTCACA
GTGCCTTCAAGCAGCCTGGGCACCCAGACCTATATC
TGCAACGTGAACCACAAGCCTTCCAACACCAAGGTG
GACAAGCGGGTGGAGCCTAAGTCCTGCGACAAGACC
CACACCTGTCCTCCCTGCCCTGCTCCTGAAGCTGCT
GGCGGCCCTTCTGTGTTCCTGTTCCCTCCAAAGCTG
AAGGACACCCTGATGATCTCCCGGACCCCTGAAGTG
ACCTGCGTGGTGGTGGACGTGTCCCACGAGGATCCT
GAAGTGAAGTTCAATTGGTACGTGGACGGCGTGGAG
GTGCACAACGCCAAGACCAAGCCTCGGGAGGAACAG
TACAACTCCACCTACCGGGTGGTGTCCGTGCTGACC
GTGCTGCACCAGGACTGGCTGAACGGCAAAGAGTAC
AAGTGCAAAGTCTCCAACAAGGCCCTGCCTGCCCCT
ATCGAAAAGACAATCTCCAAGGCCAAGGGCCAGCCT
AGGGAACCCCAGGTGTACACCCTGCCACCCAGCCGG
GAGGAAATGACCAAGAACCAGGTGTCCCTGACCTGT
CTGGTCAAGGGCTTCTACCCTTCCGATATCGCCGTG
GAGTGGGAGTCTAACGGCCAGCCTGAGAACAACTAC
AAGACCACCCCTCCTGTGCTGGACTCCGACGGCTCC
TTCTTCCTGTACTCCAAACTGACCGTGGACAAGTCC
CGGTGGCAGCAGGGCAACGTGTTCTCCTGCTCCGTG
ATGCACGAGGCCCTGCACAACCACTACACCCAGAAG
TCCCTGTCCCTGTCTCCCGGCAAG |
| LCDR1 (Combined) | 16 | SGSSSNIGSNDVS |
| LCDR2 (Combined) | 17 | KNYNRPS |
| LCDR3 (Combined) | 18 | SAWDQRQFDVV |
| LCDR1 (Kabat) | 16 | SGSSSNIGSNDVS |
| LCDR2 (Kabat) | 17 | KNYNRPS |
| LCDR3 (Kabat) | 18 | SAWDQRQFDVV |
| LCDR1 (Chothia) | 19 | SSSNIGSND |
| LCDR2 (Chothia) | 20 | KNY |
| LCDR3 (Chothia) | 21 | WDQRQFDV |
| LCDR1 (IMGT) | 22 | SSNIGSND |
| LCDR2 (IMGT) | 20 | KNY |
| LCDR3 (IMGT) | 18 | SAWDQRQFDVV |
| VL | 55 | QSVLTQPPSVSGAPGQRVTISCSGSSSNIGSNDVSW
YQQLPGTAPKLLIYKNYNRPSGVPDRFSGSKSGTSA
SLAITGLQAEDEADYYCSAWDQRQFDVVFGGGTKLT
VL |
| DNA VL | 56 | CAGAGCGTGCTGACACAGCCTCCCTCCGTGTCTGGC
GCCCCTGGCCAGAGAGTGACCATCTCCTGCTCCGGC
TCCTCCTCCAACATCGGCTCCAACGACGTGTCCTGG
TATCAGCAGCTGCCCGGCACCGCCCCTAAGCTGCTG
ATCTACAAGAACTACAACCGGCCCTCCGGCGTGCCC
GACCGGTTCTCTGGCTCCAAGTCTGGCACCTCCGCC
TCCCTGGCTATCACCGGCCTGCAGGCTGAGGACGAG
GCCGACTACTACTGCTCCGCCTGGGACCAGCGGCAG
TTCGACGTGGTGTTCGGCGGAGGCACCAAGCTGACC
GTGCTG |

TABLE 2-continued

Examples of FXI/FXIa Antibodies and Fabs

| | SEQ ID NO: | |
|---|---|---|
| Light Chain | 57 | QSVLTQPPSVSGAPGQRVTISCSGSSSNIGSNDVSW YQQLPGTAPKLLIYKNYNRPSGVPDRFSGSKSGTSA SLAITGLQAEDEADYYCSAWDQRQFDVVFGGGTKLT VLGQPKAAPSVTLFPPSSEELQANKATLVCLISDFY PGAVTVAWKADSSPVKAGVETTTPSKQSNNKYAASS YLSLTPEQWKSHRSYSCQVTHEGSTVEKTVAPTECS |
| DNA Light Chain | 58 | CAGAGCGTGCTGACACAGCCTCCCTCCGTGTCTGGC GCCCCTGGCCAGAGAGTGACCATCTCCTGCTCCGGC TCCTCCTCCAACATCGGCTCCAACGACGTGTCCTGG TATCAGCAGCTGCCCGGCACCGCCCCTAAGCTGCTG ATCTACAAGAACTACAACCGGCCCTCCGGCGTGCCC GACCGGTTCTCTGGCTCCAAGTCTGGCACCTCCGCC TCCCTGGCTATCACCGGCCTGCAGGCTGAGGACGAG GCCGACTACTACTGCTCCGCCTGGGACCAGCGGCAG TTCGACGTGGTGTTCGGCGGAGGCACCAAGCTGACC GTGCTGGGCCAGCCTAAGGCTGCCCCCAGCGTGACC CTGTTCCCCCCCAGCAGCGAGGAGCTGCAGGCCAAC AAGGCCACCCTGGTGTGCCTGATCAGCGACTTCTAC CCAGGCGCCGTGACCGTGGCCTGGAAGGCCGACAGC AGCCCCGTGAAGGCCGGCGTGGAGACCACCACCCCC AGCAAGCAGAGCAACAACAAGTACGCCGCCAGCAGC TACCTGAGCCTGACCCCCGAGCAGTGGAAGAGCCAC AGGTCCTACAGCTGCCAGGTGACCCACGAGGGCAGC ACCGTGGAAAAGACCGTGGCCCCAACCGAGTGCAGC |
| Consensus sequences | | |
| HCDR2 (Combined) | 59 | X1-I-X2-X3-X4-X5-X6-X7-T-X8-YADSVKG |
| HCDR2 (Kabat) | 59 | X1-I-X2-X3-X4-X5-X6-X7-T-X8-YADSVKG |
| HCDR2 (Chothia) | 60 | X1-X2-X3-X4-X5-X6 |
| HCDR2 (IMGT) | 61 | 1-X1-X2-X3-X4-X5-X6-T |

In specific aspects, since each of these antibodies can bind to FXI and/or FXIa, the VH, VL, full length light chain, and full length heavy chain sequences (amino acid sequences and the nucleotide sequences encoding the amino acid sequences) can be "mixed and matched" to create other FXI and/or FXIa-binding antibodies. Such "mixed and matched" FXI and/or FXIa-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), Lefranc et al., (2003) Dev. Comp. Immunol., 27, 55-77 ("IMGT" numbering scheme), or the "Combined" system.

For example, under Kabat, the CDR amino acid residues of antibody NOV1090 in the heavy chain variable domain (VH) are numbered 31-35 (HCDR1), 50-66 (HCDR2), and 99-111 (HCDR3); and the CDR amino acid residues in the light chain variable domain (VL) are numbered 22-35 (LCDR1), 51-57 (LCDR2), and 90-100 (LCDR3). Under Chothia the CDR amino acids in the VH are numbered 26-32 (HCDR1), 52-57 (HCDR2), and 99-111 (HCDR3); and the amino acid residues in VL are numbered 25-33 (LCDR1), 51-53 (LCDR2), and 92-99 (LCDR3). By combining the CDR definitions of both Kabat and Chothia, the CDRs consist of amino acid residues 26-35 (HCDR1), 50-66 (HCDR2), and 99-111 (HCDR3) in human VH and amino acid residues 22-35 (LCDR1), 51-57 (LCDR2), and 90-100 (LCDR3) in human VL. By combining the CDR definitions of both Kabat and Chothia, the "Combined" CDRs consist of amino acid residues 26-35 (HCDR1), 50-66 (HCDR2), and 99-108 (HCDR3) in human VH and amino acid residues 24-38 (LCDR1), 54-60 (LCDR2), and 93-101 (LCDR3) in human VL. As another example, under IMGT, the CDR amino acid residues in the heavy chain variable domain (VH) are numbered 26-33 (HCDR1), 51-58 (HCDR2), and 97-108 (HCDR3); and the CDR amino acid residues in the light chain variable domain (VL) are numbered 27-36 (LCDR1), 54-56 (LCDR2), and 93-101 (LCDR3). Table 2 provides exemplary Kabat, Chothia, Combined, and IMGT HCDR1, HCDR2, HCDR3, LCDR1, LCDR2, and LCDR3 for anti-FXI antibodies, e.g., antibodies AM1, AM2, AM3, and AM4. In another aspect, the present disclosure provides FXI/FXIa binding antibodies that comprise the heavy chain and light chain CDR1s, CDR2s, and CDR3s as described in Table 2, or combinations thereof.

In specific aspects, given that each of these antibodies can bind to FXI and/or FXIa and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and matched, although each antibody preferably contains a VH CDR1, 2 and 3 and a VL CDR1, 2 and 3 to create other FXI and/or FXIa binding molecules provided herein. Such "mixed and matched" FXI and/or FXIa binding antibodies can be tested using the binding assays known in the art and those described in the Examples (e.g., ELISAs, SET, Biacore™). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure. In addition to the foregoing, in one embodiment, the antigen binding fragments of the antibodies described herein can comprise a VH CDR1, 2, and 3, or a VL CDR 1, 2, and 3, wherein the fragment binds to FXI and/or FXIa as a single variable domain.

In certain aspects of the present disclosure, the anti-FXI/FXIa antibodies or antigen binding fragments thereof may have the heavy and light chain sequences of the Fabs described in Table 2. More specifically, an anti-FXI/FXIa antibody or antigen binding fragment thereof may have the heavy and light sequence of antibody AM4. In a particular aspect, an anti-FXI/FXIa antibody or antigen binding fragment thereof may have the heavy and light sequence of antibody AM3. In a particular aspect, an anti-FXI/FXIa antibody or antigen binding fragment thereof may have the heavy and light sequence of antibody AM2. In a particular aspect, an anti-FXI/FXIa antibody or antigen binding fragment thereof may have the heavy and light sequence of antibody AM1.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene.

Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene. Examples of human germline immunoglobulin genes include, but are not limited to the variable domain germline fragments described below, as well as DP47 and DPK9.

Homologous Antibodies

In yet another embodiment, the present disclosure provides an antibody, or an antigen binding fragment thereof, comprising amino acid sequences that are homologous to the sequences described in Table 2 (e.g., SEQ ID NOs: 30, 41, 48, 34, 55, 32, 43, 50, 53, 57, or 36), and the antibody binds to an FXI and/or FXIa protein (e.g., human, rabbit, and cynomolgus monkey FXIa), and retains the desired functional properties of those antibodies described in Table 2 such as AM1, AM2, AM3, or AM4. In specific aspects, such homologous antibodies retain the CDR amino acid sequences described in Table 2 (e.g., Kabat CDRs, Chothia CDRs, IMGT CDRs, or Combined CDRs).

In other embodiments, the VH and/or VL amino acid sequences may be 50%, 60%, 70%, 80%, 90%, 95%, 96%, 97%, 98% or 99% identical to the sequences set forth in Table 2. In other embodiments, the VH and/or VL amino acid sequences may be identical except for an amino acid substitution in no more than 1, 2, 3, 4 or 5 amino acid positions. An antibody having VH and VL regions having high (i.e., 80% or greater) identity to the VH and VL regions of those described in Table 2 can be obtained by mutagenesis (e.g., site-directed or PCR-mediated mutagenesis) of nucleic acid molecules described in Table 2, followed by testing of the encoded altered antibody for retained function using the functional assays described herein.

In other embodiments, the full length heavy chain and/or full length light chain amino acid sequences may be 50% 60%, 70%, 80%, 90%, 95%, 96%, 97%, 98% or 99% identical to the sequences set forth in Table 2. An antibody having a full length heavy chain and full length light chain having high (i.e., 80% or greater) identity to the full length heavy chains of those described in Table 2 can be obtained by mutagenesis (e.g., site-directed or PCR-mediated mutagenesis) of nucleic acid molecules encoding such polypeptides, followed by testing of the encoded altered antibody for retained function using the functional assays described herein.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises an amino acid sequence that is at least 90% identical to amino acid sequence of SEQ ID NOs: 30, 41, and 48; the VL comprises an amino acid sequence that is at least 90% to the amino acid sequence of SEQ ID NO: 34 or 55, and wherein the VH does not comprise the amino acid sequence of SEQ ID NO: 12 and the VL does not comprise the amino acid sequence of SEQ ID NO: 23. In a further specific aspect, the isolated anti-FXI antibody or antigen-binding fragment thereof comprises HCDR1, HCDR2, HCDR3, LCDR1, LCDR2, and LCDR3 sequences selected from those set forth in Table 2.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises an amino acid sequence that is at least 95% identical to amino acid sequence of SEQ ID NOs: 30, 41, and 48; the VL comprises an amino acid sequence that is at least 95% to the amino acid sequence of SEQ ID NO: 34 or 55, and wherein the VH does not comprise the amino acid sequence of SEQ ID NO: 12 and the VL does not comprise the amino acid sequence of SEQ ID NO: 23. In a further specific aspect, the isolated anti-FXI antibody or antigen-binding fragment thereof comprises HCDR1, HCDR2, HCDR3, LCDR1, LCDR2, and LCDR3 sequences selected from those set forth in Table 2.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises an amino acid sequence that is at least 90%, at least 95%, at least 96%, at least 97%, at least 98%, or at least 99% identical to the amino acid sequence of SEQ ID NO: 48 and the VL comprises an amino acid sequence that is at least 90%, at least 95%, at least 96%, at least 97%, at least 98%, or at least 99% identical to the amino acid sequence of SEQ ID NO: 34, and wherein the VH does not comprise the amino acid sequence of SEQ ID NO: 12 and the VL does not comprise the amino acid sequence of SEQ ID NO: 23. In a further specific aspect, the isolated anti-FXI antibody or antigen-binding fragment thereof comprises HCDR1, HCDR2, HCDR3, LCDR1, LCDR2, and LCDR3 sequences selected from those set forth in Table 2.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises an amino acid sequence that is at least 90%, at least 95%, at least 96%, at least 97%, at least 98%, or at least 99% identical to the amino acid sequence of SEQ ID NO: 41 and the VL comprises an amino acid sequence that is at least 90%, at least 95%, at least 96%, at least 97%, at least 98%, or at least 99% identical to the amino acid sequence of SEQ ID NO: 34, and wherein the VH does not comprise the amino acid sequence of SEQ ID NO: 12 and the VL does not comprise the amino acid sequence of SEQ ID NO: 23. In a further specific aspect, the isolated anti-FXI antibody or antigen-binding fragment thereof comprises HCDR1, HCDR2, HCDR3, LCDR1, LCDR2, and LCDR3 sequences selected from those set forth in Table 2.

In a specific aspect, provided herein is an isolated anti-FXI antibody or antigen-binding fragment thereof that binds within the catalytic domain of FXI and/or FXIa comprising a heavy chain variable region (VH) and a light chain variable region (VL), wherein the VH comprises an amino acid sequence that is at least 90%, at least 95%, at least 96%, at least 97%, at least 98%, or at least 99% identical to the amino acid sequence of SEQ ID NO: 30 and the VL comprises an amino acid sequence that is at least 90%, at least 95%, at least 96%, at least 97%, at least 98%, or at least 99% identical to the amino acid sequence of SEQ ID NO: 34, and wherein the VH does not comprise the amino acid sequence of SEQ ID NO: 12 and the VL does not comprise the amino acid sequence of SEQ ID NO: 23. In a further specific aspect, the isolated anti-FXI antibody or antigen-binding fragment thereof comprises HCDR1, HCDR2, HCDR3, LCDR1, LCDR2, and LCDR3 sequences selected from those set forth in Table 2.

As used herein, the percent identity between the two sequences is a function of the number of identical positions shared by the sequences (i.e., % identity equals number of identical positions/total number of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present disclosure can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In certain embodiments, an antibody of the present disclosure has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the FXIa-binding antibodies of the present disclosure.

Accordingly, the disclosure provides an isolated antibody, or an antigen binding fragment thereof, comprising a heavy chain variable region comprising HCDR1, HCDR2, and HCDR3 sequences selected from those in Table 2 and conservative modifications thereof, and a light chain variable region comprising LCDR1, LCDR2, and LCDR3 sequences selected from those in Table 2 and conservative modifications thereof; and the antibody or antigen binding fragment thereof specifically binds to FXI and/or FXIa, and wherein the antibody or antigen binding fragment thereof is not antibody NOV1401 or NOV1090.

In a specific aspect, the disclosure provides an isolated antibody, or an antigen binding fragment thereof, comprising a heavy chain variable region comprising HCDR1, HCDR2, and HCDR3 sequences of antibody AM4 as described in Table 2 and conservative modifications thereof, and a light chain variable region comprising LCDR1, LCDR2, and LCDR3 sequences of antibody AM4 as described in Table 2 and conservative modifications thereof; and the antibody or antigen binding fragment thereof specifically binds to FXI and/or FXIa, and wherein the antibody or antigen binding fragment thereof is not antibody NOV1401 or NOV1090.

In a specific aspect, the disclosure provides an isolated antibody, or an antigen binding fragment thereof, comprising a heavy chain variable region comprising HCDR1, HCDR2, and HCDR3 sequences of antibody AM2 as described in Table 2 and conservative modifications thereof, and a light chain variable region comprising LCDR1, LCDR2, and LCDR3 sequences of antibody AM2 as described in Table 2 and conservative modifications thereof; and the antibody or antigen binding fragment thereof specifically binds to FXI and/or FXIa, and wherein the antibody or antigen binding fragment thereof is not antibody NOV1401 or NOV1090.

In a specific aspect, the disclosure provides an isolated antibody, or an antigen binding fragment thereof, comprising a heavy chain variable region comprising HCDR1, HCDR2, and HCDR3 sequences of antibody AM1 as described in Table 2 and conservative modifications thereof, and a light chain variable region comprising LCDR1, LCDR2, and LCDR3 sequences of antibody AM1 as described in Table 2 and conservative modifications thereof; and the antibody or antigen binding fragment thereof specifically binds to FXI and/or FXIa, and wherein the antibody or antigen binding fragment thereof is not antibody NOV1401 or NOV1090.

In other embodiments, the antibody of the present disclosure is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the FXIa binding antibodies of the present disclosure. Accordingly, the present disclosure provides an isolated antibody optimized for expression in a mammalian cell consisting of a full length heavy chain and a full length light chain wherein the full length heavy chain has amino acid sequences selected from those described in Table 2, and conservative modifications thereof; and the full length light chain has amino acid sequences selected from those described in Table 2, and conservative modifications thereof; and the antibody specifically binds to FXI and/or FXIa (e.g., human, rabbit, and cynomolgus monkey FXIa).

Engineered and Modified Antibodies

An antibody of the present disclosure further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database (available on the world wide web at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J Immunol. 24:827-836; the contents of each of which are expressly incorporated herein by reference.

An example of framework sequences for use in the antibodies of the present disclosure are those that are structurally similar to the framework sequences used by selected antibodies of the present disclosure, e.g., consensus sequences and/or framework sequences used by monoclonal antibodies of the present disclosure. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al). Frameworks that can be utilized as scaffolds on which to build the antibodies and antigen binding fragments described herein include, but are not limited to VH1A, VH1B, VH3, Vk1, VI2, and Vk2. Additional frameworks are known in the art and may be found, for example, in the vBase data base on the world wide web at vbase.mrc-cpe.cam.ac.uk/index.php?&MMN_position=1:1.

Accordingly, an embodiment of the present disclosure relates to isolated FXI/FXIa binding antibodies, or antigen binding fragments thereof, comprising a heavy chain variable region comprising an amino acid sequence selected from the group consisting of SEQ ID NOs: 30, 41, and 48, or an amino acid sequence having one, two, three, four or five amino acid substitutions, deletions or additions in the framework region of such sequences, and further comprising a light chain variable region having an amino acid sequence selected from the group consisting of SEQ ID NOs: 34 and 55, or an amino acid sequence having one, two, three, four or five amino acid substitutions, deletions or additions in the framework region of such sequences, and wherein the antibody or antigen binding fragment thereof is not NOV1401.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to FXIa. Such frameworks or scaffolds include the 5 main idiotypes of human immunoglobulins, or fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the disclosure pertains to generating non-immunoglobulin based antibodies using non-immunoglobulin scaffolds onto which CDRs of the present disclosure can be grafted. Known or future non-immunoglobulin frameworks and scaffolds may be employed, as long as they comprise a binding region specific for the target FXI and/or FXIa protein. Known non-immunoglobulin frameworks or scaffolds include, but are not limited to, fibronectin (Compound Therapeutics, Inc., Waltham, MA), ankyrin (Molecular Partners AG, Zurich, Switzerland), domain antibodies (Domantis, Ltd., Cambridge, MA, and Ablynx nv, Zwijnaarde, Belgium), lipocalin (Pieris Proteolab AG, Freising, Germany), small modular immuno-pharmaceuticals (Trubion Pharmaceuticals Inc., Seattle, WA), maxybodies (Avidia, Inc., Mountain View, CA), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the present disclosure using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company *Pieris ProteoLab AG*. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

The present disclosure provides fully human antibodies that specifically bind to a FXI and/or FXIa protein. Compared to the chimeric or humanized antibodies, the human FXI/FXIa-binding antibodies of the present disclosure have further reduced antigenicity when administered to human subjects.

Camelid Antibodies

Antibody proteins obtained from members of the camel and dromedary (*Camelus bactrianus* and *Calelus dromaderius*) family including new world members such as llama species (*Lama paccos*, *Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitate drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present disclosure is a camelid antibody or nanobody having high affinity for FXI and/or FXIa. In certain embodiments herein, the camelid antibody or nanobody is naturally produced in the camelid animal, i.e., is produced by the camelid following immunization with FXI and/or FXIa or a peptide fragment thereof, using techniques described herein for other antibodies. Alternatively, the FXI and/or FXIa-binding camelid nanobody is engineered, i.e., produced by selection for example from a library of phage displaying appropriately mutagenized camelid nanobody proteins using panning procedures with FXI and/or FXIa, and/or domains and/or peptide fragments thereof, as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the present disclosure into nanobody or single domain antibody framework sequences, as described for example in PCT/EP93/02214.

Bispecific Molecules and Multivalent Antibodies

In another aspect, the present disclosure features bispecific or multispecific molecules comprising a FXI and/or FXIa-binding antibody, or a fragment thereof, of the present disclosure. An antibody of the present disclosure, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the present disclosure may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the present disclosure, an antibody of the present disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for FXI and/or FXIa and a second binding specificity for a second target epitope. For example, the second target epitope is another epitope of FXI and/or FXIa different from the first target epitope.

Additionally, for the present disclosure in which the bispecific molecule is multi-specific, the molecule can further include a third binding specificity, in addition to the first and second target epitope.

In one embodiment, the bispecific molecules of the present disclosure comprise as a binding specificity at least one antibody, or an antibody fragment thereof, including, e.g., a Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123).

Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21). A diabody can be fused to Fc to generate a "di-diabody" (see Lu et al., 2004 J. Biol. Chem., 279(4):2856-65).

Other antibodies which can be employed in the bispecific molecules of the present disclosure are murine, chimeric and humanized monoclonal antibodies.

Bispecific molecules can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, IL).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')2 or ligand x Fab fusion protein. A bispecific molecule of the present disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present disclosure provides multivalent compounds comprising at least two identical or different antigen-binding portions of the antibodies of the present disclosure binding to FXIa. The antigen-binding portions can be linked together via protein fusion or covalent or non covalent linkage. Alternatively, methods of linkage have been described for the bispecfic molecules. Tetravalent compounds can be obtained for example by cross-linking antibodies of the antibodies of the present disclosure with an antibody that binds to the constant regions of the antibodies of the present disclosure, for example the Fc or hinge region. Trimerizing domain are described for example in Borean patent EP 1 012 28061. Pentamerizing modules are described for example in PCT/EP97/05897.

Antibodies with Extended Half Life

The present disclosure provides for antibodies that specifically bind to FXI/FXIa protein which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dendritic cells). A variety of strategies can be used to extend the half life of the antibodies of the present disclosure. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nanocarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the present disclosure. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a nonnative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin (e.g., human serum albumin; HSA) in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622. In addition, in the context of a bispecific antibody as described above, the specificities of the antibody can be designed such that one binding domain of the antibody binds to FXIa while a second binding domain of the antibody binds to serum albumin, preferably HSA.

The strategies for increasing half life is especially useful in nanobodies, fibronectin-based binders, and other antibodies or proteins for which increased in vivo half life is desired.

Antibody Conjugates

The present disclosure provides antibodies or fragments thereof that specifically bind to a FXI/FXIa protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the present disclosure provides fusion proteins comprising an antigen-binding fragment of an antibody described herein (e.g., a Fab fragment, Fd fragment, Fv fragment, F(ab)2 fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the present disclosure or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to a FXIa protein may be recombined with one or more components, motifs, sections, parts, domains, fragments, etc. of one or more heterologous molecules.

Moreover, the antibodies or fragments thereof can be fused to marker sequences, such as a peptide to facilitate purification. In specific embodiments, the marker amino acid sequence is a hexa-histidine peptide (SEQ ID NO: 68), such as the tag provided in a pQE vector (QIAGEN, Inc., 9259 Eton Avenue, Chatsworth, CA, 91311), among others, many of which are commercially available. As described in Gentz et al., 1989, Proc. Natl. Acad. Sci. USA 86:821-824, for instance, hexa-histidine (SEQ ID NO: 68) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other embodiments, antibodies of the present disclosure or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I,), carbon (14C), sulfur (35S), tritium (3H), indium (115In, 113In, 112In, and 111In,), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and noradioactive paramagnetic metal ions.

The present disclosure further encompasses uses of antibodies or fragments thereof conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alph-emiters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N",N'"-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies

The present disclosure also provides polynucleotides comprising nucleic acid sequences that encode the VH, VL, full length heavy chain, and/or full length light chain of antibodies described herein that specifically bind to a FXI and/or FXIa protein (e.g., human, rabbit, and cynomolgus monkey FXIa), for example, antibodies AM1, AM2, AM3, and AM4. Such nucleic acid sequences can be optimized for expression in mammalian cells (for example, see Table 2).

In a specific aspect, provided herein is a polynucleotide comprising nucleotide sequences encoding a VL, VH or a VL and VH of an anti-FXI/FXIa antibody or antigen-binding fragment described herein, e.g., antibody AM1, AM2, AM3, or AM4.

In a specific aspect, provided herein is a polynucleotide comprising nucleotide sequences encoding a heavy chain, light chain, or a heavy chain and light chain of the antibody or antigen-binding fragment described herein, e.g., antibody AM1, AM2, AM3, or AM4.

In particular aspects, provided herein is a polynucleotide comprising nucleotide sequences set forth in Table 2, for example, SEQ ID NOs: 31, 33, 35, 37, 42, 44, 49, 51, 52, 54, 56, and 58.

In specific aspects, provided herein is a vector (e.g., expression vector) comprising a polynucleotide described herein (e.g., Table 2).

In certain aspects, provided herein is a host cell comprising a vector described herein or a polynucleotide described herein. In specific aspects, the host cell is a eukaryotic cell. In certain aspects, the host cell is a mammalian cell (e.g., non-human mammalian cell, such as CHO cells). In particular aspects, a host cell comprises (i) a vector or polynucleotide comprising nucleotide sequences encoding a VH or a heavy chain and (ii) a vector or polynucleotide comprising nucleotide sequences encoding a VL or a light chain. In specific aspects, a first host cell comprises a vector or polynucleotide comprising nucleotide sequences encoding a VH or a heavy chain and a second host cell comprises a vector or polynucleotide comprising nucleotide sequences encoding a VL or a light chain.

In particular aspects, provided herein is a method of producing an anti-FXI/FXIa antibody or fragment thereof, comprising the step of culturing a host cell described herein under conditions suitable for expression of the anti-FXI/FXIa antibody or fragment thereof.

In certain aspects, the method of producing an anti-FXI/FXIa antibody or fragment thereof further comprises purifying the anti-FXI/FXIa antibody or fragment thereof.

Nucleic Acids Encoding the Antibodies

The present disclosure provides substantially purified nucleic acid molecules which encode polypeptides comprising segments or domains of the FXIa-binding antibody chains described above. Some of the nucleic acids of the present disclosure comprise the nucleotide sequence encoding the heavy chain variable region shown in SEQ ID NO: 30, 41, or 48, and/or the nucleotide sequence encoding the light chain variable region shown in SEQ ID NO: 34 or 55. In a specific embodiment, the nucleic acid molecules are those identified in Table 2. Some other nucleic acid molecules of the present disclosure comprise nucleotide sequences that are substantially identical (e.g., at least 65, 80%, 95%, or 99%) to the nucleotide sequences of those identified in Table 2. When expressed from appropriate expression vectors, polypeptides encoded by these polynucleotides are capable of exhibiting FXI and/or FXIa antigen binding capacity.

Also provided in the present disclosure are polynucleotides which encode at least one CDR region and usually all three CDR regions from the heavy or light chain of the FXIa-binding antibody set forth above. Some other polynucleotides encode all or substantially all of the variable region sequence of the heavy chain and/or the light chain of the FXIa-binding antibody set forth above. Because of the degeneracy of the code, a variety of nucleic acid sequences will encode each of the immunoglobulin amino acid sequences.

The nucleic acid molecules of the present disclosure can encode both a variable region and a constant region of the antibody. Some of nucleic acid sequences of the present disclosure comprise nucleotides encoding a heavy chain sequence that is substantially identical (e.g., at least 80%, 90%, or 99%) to the heavy chain sequence set forth in SEQ ID NO: 32, 43, 50, or 53. Some other nucleic acid sequences comprising nucleotide encoding a light chain sequence that is substantially identical (e.g., at least 80%, 90%, or 99%) to the light chain sequence set forth in SEQ ID NO: 57 or 36.

The polynucleotide sequences can be produced by de novo solid-phase DNA synthesis or by PCR mutagenesis of an existing sequence (e.g., sequences as described in the Examples below) encoding a FXIa-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the present disclosure are expression vectors and host cells for producing the FXI and/or FXIa-binding antibodies described above. Various expression vectors can be employed to express the polynucleotides encoding the FXIa-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the FXIa-binding polynucleotides and polypeptides in mammalian (e.g., human) cells include pThioHis A, B & C, pcDNA3.1/His, pEBVHis A, B & C, (Invitrogen, San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a FXIa-binding antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a FXIa-binding antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted FXIa-binding antibody sequences. More often, the inserted FXI and/or FXIa-binding antibody sequences are linked to a signal sequences before inclusion in the vector. Vectors to be used to receive sequences encoding FXI and/or FXIa-binding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the FXI and/or FXIa-binding antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express FXIa-binding polypeptides of the present disclosure. Insect cells in combination with baculovirus vectors can also be used.

In some specific embodiments, mammalian host cells are used to express and produce the FXI and/or FXIa-binding polypeptides of the present disclosure. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, and transformed B-cells. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences.

These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express FXIa-binding antibody chains or binding fragments can be prepared using expression vectors of the present disclosure which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Framework or Fc Engineering

Engineered antibodies of the present disclosure include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the present disclosure.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the present disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the present disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the mutations as described in U.S. Pat. No. 6,277,375 to Ward can be used. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In a specific embodiment, an anti-FXI/FXIa antibody described herein (e.g., antibody comprising VL CDRs and VH CDRs of antibody AM1, AM2, AM3, or AM4) comprises a human IgG (e.g., IgG1) Fc region comprising two amino acid substitutions, D265A and P329A, to reduce the likelihood for ADCC or CDC caused by any surface-associated FXI. These Alanine substitutions have been shown to reduce ADCC and CDC (see, e.g., Idosugie et al., J. Immunol. 164:4178-4184, 2000; Shields et al., J. Biol. Chem. 276:6591-6604, 2001).

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present disclosure to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the FXIa-binding antibodies having VH and VL sequences or full length heavy and light chain sequences shown herein can be used to create new FXIa-binding antibodies by modifying full length heavy chain and/or light chain sequences, VH and/or VL sequences, or the constant region(s) attached thereto. Thus, in another aspect of the present disclosure, the structural features of a FXIa-binding antibody of the present disclosure are used to create structurally related FXIa-binding antibodies that retain at least one functional property of the antibodies of the present disclosure, such as binding to human FXIa and also inhibiting one or more functional properties of FXIa (e.g., inhibit FXIa binding to the FXIa receptor, inhibit FXIa-dependent cell proliferation).

For example, one or more CDR regions of the antibodies of the present disclosure, or mutations thereof, can be combined recombinantly with known framework regions and/or other CDRs to create additional, recombinantly-engineered, FXIa-binding antibodies of the present disclosure, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the present disclosure provides a method for preparing a FXIa-binding antibody optimized for expression in a mammalian cell consisting of: a full length heavy chain antibody sequence having a sequence selected from the group of SEQ ID NOs: 32, 43, 50, and 53; and a full length light chain antibody sequence having a sequence selected from the group of SEQ ID NO: 36 and 57; altering at least one amino acid residue within the full length heavy chain antibody sequence and/or the full length light chain antibody sequence to create at least one altered antibody sequence; and expressing the altered antibody sequence as a protein. In one embodiment, the alteration of the heavy or light chain is in the framework region of the heavy or light chain.

The altered antibody sequence can also be prepared by screening antibody libraries having fixed CDR3 sequences or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the FXIa-binding antibodies described herein, which functional properties include, but are not limited to, specifically binding to human, cynomolgus, rat, and/or mouse FXIa; and the antibody inhibit FXIa-dependent cell proliferation in a F36E and/or Ba/F3-FXIaR cell proliferation assay.

In certain embodiments of the methods of engineering antibodies of the present disclosure, mutations can be introduced randomly or selectively along all or part of an FXIa-binding antibody coding sequence and the resulting modified FXIa-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

In certain embodiments of the present disclosure antibodies have been engineered to remove sites of deamidation. Deamidation is known to cause structural and functional changes in a peptide or protein. Deamination can result in decreased bioactivity, as well as alterations in pharmacokinetics and antigenicity of the protein pharmaceutical. (Anal Chem. 2005 Mar. 1; 77(5):1432-9).

In certain embodiments of the present disclosure the antibodies have been engineered to increase pI and inprove their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-FXI/FXIa antibodies, or Fabs, of the present disclosure improved their solubility, enabling the antibodies to be formulated at higher concentrations (>100 mg/ml). Formulation of the antibodies at high concentrations (e.g. >100 mg/ml) offers the advantage of being able to administer higher doses of the antibodies, which in turn may enable reduced dosing frequency, a significant advantage for treatment of chronic diseases including thrombotic and/or thromboembolic disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pI resulting in longer shelf-life and bioactivity in vivo. Preferably, the pI is greater than or equal to 8.2.

The functional properties of the altered antibodies can be assessed using standard assays available in the art and/or described herein, such as those set forth in the Examples (e.g., ELISAs, aPTT assay).

Prophylactic and Therapeutic Uses

Antibodies that bind FXI and/or FXIa as described herein (e.g., antibodies described in Table 2, such as, anti-FXI antibodies comprising VL CDRs and VH CDRs of antibody AM1, AM2, AM3 or AM4), can be used at a therapeutically useful concentration for the treatment of a thromboembolic disease or disorder (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, or systemic embolism) by administering to a subject in need thereof an effective amount of the antibodies or antigen binding fragments of the present disclosure. The present disclosure provides a method of treating thromboembolic disorder (e.g., thrombotic disorders) by administering to a subject in need thereof an effective amount of the antibodies of the present disclosure. The present disclosure provides a method of treating thromboembolic disorders (e.g., thrombic stroke, atrial fibrillation, stroke prevention in atrial fibrillation (SPAF), deep vein thrombosis, venous thromboembolism, pulmonary embolism, acute coronary syndromes (ACS), ischemic stroke, acute limb ischemia, chronic thromboembolic pulmonary hypertension, or systemic embolism) by administering to a subject in need thereof an effective amount of the antibodies of the present disclosure (e.g., antibody AM1, AM2, AM3, or AM4).

The antibodies described herein (e.g., antibodies described in Table 2, such as, antibody or anti-FXI antibodies comprising VL CDRs and VH CDRs of antibody, AM1, AM2, AM3, or AM4) can be used, inter alia, to prevent treat, prevent, and improve thromboembolic conditions or disorders, including but not limited to thrombotic disorders, as described in greater detail herein.

The antibodies provided herein (e.g., antibodies described in Table 2, such as, anti-FXI antibodies comprising VL CDRs and VH CDRs of antibody AM1, AM2, AM3, or AM4) can also be used in combination with other agents for the prevention, treatment, or improvement of thromboembolic disorders. For example, statin therapies may be used in combination with the FXIa antibodies and antigen binding fragments of the present disclosure for the treatment of patients with thrombotic and/or thromboembolic disorders.

In a specific embodiment, provided herein is a method of treating or preventing stroke in a patient with atrial fibrillation, comprising administering to the patient in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VHCDRs of antibody AM1, AM2, AM3, or AM4.

In a specific embodiment, provided herein is a method of managing or preventing risks or conditions associated with atrial fibrillation (AF), such as embolic stroke and systemic embolism, in a patient with atrial fibrillation, comprising administering to the patient in need hereof an effective amount of an anti-FXI/FXIa antibody described herein, for example, an anti-FXI/FXIa antibody described in Table 2, such as, antibody AM1, AM2, AM3, or AM4 or anti-FXI/FXIa antibodies comprising VL CDRs and VHCDRs of antibody AM1, AM2, AM3, or AM4.

In a specific embodiment, provided herein is a method of treating, managing or preventing conditions associated with atrial fibrillation (AF), such as embolic stroke and systemic embolism, in a patient with atrial fibrillation, comprising administering to the patient in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VHCDRs of antibody AM1, AM2, AM3, or AM4. In particular embodiments, an AF patient has a high bleeding risk.

In a specific embodiment, provided herein is a method of treating, managing or preventing deep vein thrombosis or conditions associated therewith, in a subject (e.g., a subject with, or at risk of developing, deep vein thrombosis), comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In a specific embodiment, provided herein is a method of treating, managing or preventing venous thromboembolism (VTE) or conditions associated therewith, in a subject (e.g., a subject with, or at risk of developing, venous thromboembolism), comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4. In particular embodiments, subjects being treated with an anti-FXI antibody provided herien have experienced 1) a first unprovoked VTE with low risk for bleeding, 2) recurrence of unprovoked VTE, or 3) VTE associated with thrombophilia including cancer patients.

In a specific embodiment, provided herein is a method of treating, managing or preventing pulmonary embolism or conditions associated therewith, in a subject (e.g., a subject with, or at risk of developing, pulmonary embolism), comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In a specific embodiment, provided herein is a method of treating, managing or preventing acute coronary syndromes (ACS) or conditions associated therewith, in a subject, comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In a specific embodiment, provided herein is a method of treating, managing or preventing ischemic stroke, in a subject (e.g., a subject with, or at risk of developing, ischemic stroke), comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In a specific embodiment, provided herein is a method of treating, managing or preventing acute limb ischemia, in a subject, comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In a specific embodiment, provided herein is a method of treating, managing or preventing chronic thromboembolic pulmonary hypertension, in a subject, comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In a specific embodiment, provided herein is a method of treating, managing or preventing systemic embolism, in a subject (e.g., a subject with, or at risk of developing, systemic embolism), comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In a certain embodiment, provided herein is a method of treating, managing, or preventing thromboembolic conditions that are catheter-related conditions (e.g., Hickman catheter in cancer patients) in which catheters become thrombosed, or extracorporeal membrane oxygenation (ECMO), in which the tubing develops clots, comprising administering to the subject in need hereof an effective amount of an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4.

In particular embodiments, subjects in need of treatment with an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4, may include:

Subjects with indications for chronic anticoagulation therapy (e.g., AF, left ventricular thrombus, prior cardioembolic stroke)

subjects at intermediate-to-high risk for major bleeding;

subjects undergoing elective or primary percutaneous coronary intervention (PCI) with stenting which may be require to receive dual antiplatelet therapy (aspirin and P2Y12 receptor antagonists) to prevent stent thrombosis.

In particular embodiments, one of the following conditions can be treated or managed with an anti-FXI antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4:

thromboembolism in subjects with suspected or confirmed cardiac arrhythmia such as paroxysmal, persistent or permanent atrial fibrillation or atrial flutter;

stroke prevention in atrial fibrillation (SPAF), a subpopulation of which is AF patients undergoing percutaneous coronary interventions (PCI);

acute venous thromboembolic events (VTE) treatment and extended secondary VTE prevention in patients at high risk for bleeding;

cerebral and cardiovascular events in secondary prevention after transient ischemic attack (TIA) or non-disabling stroke and prevention of thromboembolic events in heart failure with sinus rhythm;

clot formation in left atrium and thromboembolism in subjects undergoing cardioversion for cardiac arrhythmia;

thrombosis before, during and after ablation procedure for cardiac arrhythmia;

venous thrombosis, this includes but not exclusively, treatment and secondary prevention of deep or superficial veins thrombosis in the lower members or upper member, thrombosis in the abdominal and thoracic veins, sinus thrombosis and thrombosis of jugular veins;

thrombosis on any artificial surface in the veins like catheter or pacemaker wires;

pulmonary embolism in patients with or without venous thrombosis;

Chronic Thromboembolic Pulmonary Hypertension (CTEPH);

arterial thrombosis on ruptured atherosclerotic plaque, thrombosis on intra-arterial prosthesis or catheter and thrombosis in apparently normal arteries, this includes but not exclusively acute coronary syndromes, ST elevation myocardial infarction, non ST elevation myocardial infarction, unstable angina, stent thrombosis, thrombosis of any artificial surface in the arterial system and thrombosis of pulmonary arteries in subjects with or without pulmonary hypertension;

thrombosis and thromboembolism in patients undergoing percutaneous coronary interventions (PCI);

cardioembolic and cryptogenic strokes;

thrombosis in patients with invasive and non-invasive cancer malignancies;

thrombosis over an indwelling catheter;

thrombosis and thromboembolism in severely ill patients;

cardiac thrombosis and thromboembolism, this includes but not exclusively cardiac thrombosis after myocardial infarction, cardiac thrombosis related to condition such as cardiac aneurysm, myocardial fibrosis, cardiac enlargement and insufficiency, myocarditis and artificial surface in the heart;

thromboembolism in patients with valvular heart disease with or without atrial fibrillation;

thromboembolism over valvular mechanic or biologic prostheses;

injuries or trauma in patients who had native or artificial cardiac patches, arterial or venous conduit tubes after heart repair of simple or complex cardiac malformations;

venous thrombosis and thromboembolism after knee replacement surgery, hip replacement surgery, and orthopedic surgery, thoracic or abdominal surgery;

arterial or venous thrombosis after neurosurgery including intracranial and spinal cord interventions;

congenital or acquired thrombophilia including but not exclusively factor V Leiden, prothrombin mutation, antithrombin III, protein C and protein S deficiencies, factor XIII mutation, familial dysfibrinogenemia, congenital deficiency of plasminogen, increased levels of factor XI, sickle cell disease, antiphospholipid syndrome, autoimmune disease, chronic bowel disease, nephrotic syndrome, hemolytic uremia, myeloproliferative disease, disseminated intra vascular coagulation, paroxysmal nocturnal hemoglobinuria and heparin induced thrombopenia;

thrombosis and thromboembolism in chronic kidney disease;

thrombosis and thromboembolism in end stage renal disease (ESRD);

thrombosis and thromboembolism in patients with chronic kidney disease or ESRD undergoing hemodialysis; and thrombosis and thromboembolism in patients undergoing hemodialysis and/or extra-corporal membrane oxygenation.

In particular aspects, provided herein is a method of treating, managing preventing, or reducing the risk of stroke and/or systemic embolism, in a subject, comprising administering to the subject in need hereof an effective amount of an anti-FXI/FXIa antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4, wherein the subject has atrial fibrillation, such as non-valvular atrial fibrillation. In specific aspects, the subject has atrial fibrillation, such as non-valvular atrial fibrillation, with a demonstrated high risk of bleeding.

In particular aspects, provided herein is a method of treating, managing preventing, or reducing the risk of stroke and/or systemic embolism, in a subject, comprising administering to the subject in need hereof an effective amount of an anti-FXI/FXIa antibody described herein, for example, an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4, wherein the subject has ESRD and are undergoing dialysis. In specific aspects, the subject has atrial fibrillation, such as non-valvular atrial fibrillation, and ESRD and is undergoing dialysis. In specific aspects, the subject has atrial fibrillation, such as non-valvular atrial fibrillation, with demonstrated high risk of bleeding, and ESRD, and is undergoing dialysis.

For example, subjects with demonstrated high risk of bleeding can be identified by previous medical history of bleeding, for example, bleeding during or after surgery or bleeding when treated with an anticoagulant (e.g. Warfarin). In addition, subjects with demonstrated high risk of bleeding can be identified by in vitro/ex vivo assays known in the art, for example, assays with a subject's plasma measuring aPTT and biomarkers of the extrinsic coagulation pathways, such as prothrombin time (PT) and thrombin time (TT).

Bleeding risk assessment tools specific to the atrial fibrillation patients e.g., HAS-BLED, ATRIA, HEMORR2HAGES; ORBIT and ABC risk score were developed to predict the bleeding risk in patients with atrial fibrillation. Unfortunately, as the bleeding risk is tightly correlated with the stroke risk, those risk score were of rather limited value to guide therapeutic decisions to use vitamin K antagonists such as warfarin or NOACS (Novel Oral Anticoagulants). However, bleeding risk scores may become of considerable help to identify patients who can benefit of a new therapy with a reduced bleeding risk e.g. anti-FXI/FXIa antibody (e.g., antibody AM1, AM2, AM3, or AM4).

In particular aspects, subjects with moderate to high risk for stroke and systemic embolism have a CHA2DS2VASc risk score 2. In further particular aspects, subjects with a HAS BLED risk score ≥3 is characterized as having a high risk of bleeding (see Gallego, et al., (2012) Carc Arrhythm Electrophysiol.; 5:312-318, and Friberg et al., (2012) Circulation.; 125:2298-2307).

The risk of thromboembolic events including stroke, systemic embolism, coronary or peripheral artery thrombosis, venous thrombosis and pulmonary embolism increases with presence of predisposing factors such as thrombophilia, vessel wall damage and stasis. Evaluation of medical history, familiar antecedents and associated co-morbidities can help to stratify patients according to their thromboembolic risks. In patients with atrial fibrillation, several scoring systems e.g., CHADS2 and CHA2DS2-VASc have been developed to assess stroke risk. Each was developed based on data from randomized trials, and clinical and epidemiologic cohort studies, and translated a weighted, multivariate formula of stroke risk factors to a simplified, easy-to-use mnemonic device, algorithm, calculator, or online tool. The CHADS2 risk score was used stratification tool to predict thromboembolic risk in atrial fibrillation patients (LIP 2011; Camm et al 2012); however, accumulated evidence shows that CHA2DS2-VASc is at least as good as or possibly better than, scores such as CHADS2 in identifying patients who develop stroke and thromboembolism and definitively better at identifying 'truly low-risk' patients with atrial fibrillation. The CHA2DS2-VASc score is presently recommended by Guidelines (Camm et al Eur Heart J (2012) 33, 2719-2747; January et al, AHA/ACC/HRS Atrial Fibrillation Guideline; J Am Coll Cardiol 2014; 64:2246-80) to guide the decision with regard to patients who should benefit of anticoagulant therapy and also to identify low risk patients in whom anticoagulation therapy is not warranted.

In specific aspects, a subject being treated by the methods provided herein is at least 18 years old. In another aspect, a subject being treated by the methods provided herein is at least 50 years old. In another aspect, a subject being treated by the methods provided herein is at least 55 years old. In another aspect, a subject being treated by the methods provided herein is at least 60 years old. In another aspect, a subject being treated by the methods provided herein is at least 65 years old.

In specific aspects, a subject being treated by the methods provided herein has a body mass index (BMI) that is greater than or equal to 18 kg/m$^2$. In another aspect, a subject being treated by the methods provided herein has a BMI that is greater than or equal to 30 kg/m$^2$. In another aspect, a subject being treated by the methods provided herein has a BMI that is greater than or equal to 35 kg/m$^2$. In another aspect, a subject being treated by the methods provided herein has a BMI that is greater than or equal to 40 kg/m$^2$.

In a specific aspect, provided herein are methods of managing bleeding in a patient being treated or administered an anti-FXI antibody provided herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4), for example, bleeding associated with trauma, surgery, menstruation or post-delivery, said method comprises reversing of the anticoagulant effect. FXI deficiency is rarely associated with spontaneous bleeding manifestations; in specific aspects, bleeding is most typically associated with trauma, surgery, menstruation or post-delivery. Prolonged bleeding may occur after a major trauma or after surgery involving organs with high fibrinolytic area such as buccal, nasal, genital or urinary mucosa. Tooth extraction, tonsillectomy and ablation of the uterus or prostate are examples of surgeries that entail a high risk of bleeding. People with the disorder also have a strong tendency to develop epistaxis and ecchymoses, and more rarely, bleeding into the urine or intestines. Spontaneous muscle or joint and intracranial bleeding frequency is not increased in patients with FXI deficiency. Venous puncture is not usually associated with an extended bleeding. Other genetic mutations associated with FXI deficiency may contribute to the heterogeneous and unpredictable bleeding tendency in patients with severe FXI deficiency. Concomitant use of antiplatelets, other anticoagulants and fibrinolytic agents can increase the risk of bleeding.

In particular embodiments, provided herein is a method of managing bleeding in a patient being treated with an anti-FXI antibody provided herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4), said method comprises temporarily reversing of the anticoagulant effect for a sufficient time to manage the bleeding. In specific embodiments, the step of reversing of the anticoagulant effect comprises (i) fluid replacement using colloids, crystalloids, human plasma or plasma proteins such as albumin; or (ii) transfusion with packed red blood or whole blood. In a particular embodiment, therapeutic agents for reversal of the effect of anticoagulants, for example, in cases of severe emergency, include, but are not limited to, prohemostasis blood components such as fresh frozen plasma (FFP), prothrombin complex concentrates (PCC) and activated PCC [(APCC); e.g. factor VIII inhibitor bypass activity (FEIBA)] and recombinant activated factor VII (rFVIIa). In one embodiment, a regimen comprising administration of rFVIIa, for example, at a dose of 30 μg/kg followed by administration of rFVIIa, for example, at a dose of 15-30 μg/kg every 2-4 hours for 24-48 hours in addition to tranexamic acid, for example, 1 g every 6 hours for 5 to 7 days may have potential to recover hemostasis and stop bleeding in subjects treated with an anti-FXI antibody provided herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) who are undergoing major surgery and in patients with an active non-accessible bleeding site. For instance, Riddell et al reported experience in 4 patients with severe FXI deficiency without inhibitor undergoing surgery (Riddell et al., 2011, Thromb. Haemost.; 106: 521-527); patients were administered rFVIIa 30 μg/kg and tranexamic acid 1 g i.v. at induction of anesthesia. Subsequent bolus doses of rFVIIa, for example, 15-30 μg/kg were administered at 2 to 4 hourly intervals as guided by rotational thromboelastometry (ROTEM) results. Patients were treated with rFVIIa at above mentioned doses for 24-48 hours. Tranexamic acid 1 g every six-hourly was continued for five days. In this small series, rFVIIa at doses as low as 15-30 μg/kg in combination with tranexamic acid was safe and effective in correcting the hemostatic defect in severe FXI deficiency in this study. In another study comprising 4 patients with severe FXI deficiency with inhibitor (autologous neutralizing FXI antibodies usually acquired after transfusion or administration of blood products to patients with severe FXI deficiency) who experienced 5 surgeries, the authors (Livnat et al., 2009, Thromb. Haemost.; 102: 487-492) applied the following protocol: 1 g of tranexamic acid orally two hours before surgery, then patients received immediately prior to the interventions another 1 g tranexamic acid i.v. Recombinant FVIIa at doses ranging from 15 to 30 μg/kg was infused at the completion of surgery. Subsequently, oral tranexamic acid 1 g was given every 6 hour for at least 7 days. Fibrin glue was sprayed at the bed of the extirpated gallbladder in one patient. This protocol secured normal hemostasis in patients with severe FXI deficiency with inhibitor.

In one aspect, fibrin glue can be used to restore local hemostasis during dental surgery in patients with FXI deficiency (Bolton-Maggs (2000) Haemophilia; 6 (S1):100-9). In a certain embodiment with respect to methods to manage bleeding in patients being treated with an anti-FXI antibody provided herein (e.g., antibody AM1, AM2, AM3, or AM4), a regimen consisting of tranexamic acid 1 g every 6 hours for 5 to 7 days associated with the use of fibrin glue could be used to establish local hemostasis in subjects undergoing minor surgery and in subjects with accessible bleeding site, including oral and nasal bleeding events.

In a particular aspect, provided herein are methods of managing bleeding or bleeding risk in a patient treated or administered an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4), comprising the step of administering to the patient in need thereof, an anti-idiotype antibody, or antigen binding fragment thereof (e.g., Fab), of the anti-FXI antibody, wherein the anti-idiotype or antigen binding fragment thereof (e.g., Fab) specifically binds to the anti-FXI antibody and blocks the anti-FXI antibody from binding to FXI. In specific embodiments, an anti-idiotype antibody or antigen binding fragment thereof (e.g., Fab) reverses the effects of an anti-FXI antibody described herein to mitigate bleeding risks, for example during urgent major surgery or trauma.

In specific aspects, an anti-idiotype antibody or antigen binding fragment thereof (e.g., Fab) reverses or inhibits an anti-FXI antibody's anti-coagulant effects. In particular aspects, the anti-idiotype antibody or antigen binding fragment thereof (e.g., Fab) is administered to a patient in need thereof to temporarily reverse the anti-coagulant effect of an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4).

In a particular aspect, provided herein are methods of managing bleeding or bleeding risk in a patient treated or administered an anti-FXI antibody such as antibody AM1, AM2 AM3, or AM4, comprising the step of administering to the patient in need thereof, an anti-idiotype antibody, or antigen binding fragment thereof (e.g., Fab), of the anti-FXI antibody such as antibody AM1, AM2, AM3, or AM4, wherein the anti-idiotype antibody, or antigen binding fragment thereof (e.g., Fab), specifically binds to the antigen-binding region of an anti-FXI antibody and blocks the anti-FXI antibody from binding to FXI and/or FXIa. In a specific embodiment, the anti-idiotype antibody, or antigen binding fragment thereof (e.g., Fab), of an anti-FXI antibody such as antibody AM1, AM2, AM3, or AM4 reverses or inhibits one or more of the anti-coagulant effects of the anti-FXI antibody. In certain embodiments, a temporary reversal or inhibition of one or more of the anti-coagulant effects of the anti-FXI antibody (e.g., antibody AM1, AM2, AM3, or AM4) is achieved. In specific embodiments, following the temporary reversal or inhibition of the anti-FXI antibody (e.g., antibody AM1, AM2, AM3, or AM4), the anti-FXI antibody is again administered to the patient.

In a particular aspect, provided herein is a method of managing or reducing bleeding or bleeding risk in a subject treated or administered an anti-FXI antibody or antigen-binding fragment described herein (e.g., antibody AM1, AM2, AM3, or AM4), comprising the step of administering to the subject in need thereof, an anti-idiotype antibody or fragment thereof that specifically binds to the anti-FXI antibody and blocks the anti-FXI antibody from binding to FXI, and wherein the anti-idiotype antibody or fragment thereof reverses the anti-coagulant activity of the anti-FXI antibody. In a specific aspect, the anti-idiotype antibody or fragment thereof is administered to the subject once or twice to temporarily reverse the anti-coagulant effect of the anti-FXI antibody.

In specific aspects, provided herein is a method of managing or reducing bleeding or bleeding risk in a subject treated or administered an anti-FXI antibody or antigen-binding fragment described herein (e.g., antibody AM1, AM2, AM3, or AM4), said method comprises reversing of the anticoagulant effect for a sufficient time to manage the bleeding by one of the following: (i) fluid replacement using colloids, crystalloids, human plasma or plasma proteins such as albumin; (ii) transfusion with packed red blood or whole blood; or (iii) administration of fresh frozen plasma (FFP), prothrombin complex concentrates (PCC), activated PCC (APCC), such as, factor VIII inhibitor, and/or recombinant, activated factor VII. In a specific aspect, said method comprises administering to the subject one or two or more doses of an anti-idiotype antibody or fragment thereof that specifically binds to the anti-FXI/FXIa antibody described herein (e.g., antibody AM1, AM2, AM3, or AM4). In a specific aspect, the anti-idiotype antibody blocks the anti-FXI/FXIa antibody from binding to FXI/FXIa, and is capable of reversing the anti-coagulant activity of the anti-FXI antibody. In a specific aspect, said method comprises reversing (e.g., temporarily reversing) of the anticoagulant effect for a sufficient time to manage the bleeding by one of the following: (i) fluid replacement using colloids, crystalloids, human plasma or plasma proteins such as albumin; (ii) transfusion with packed red blood or whole blood; or (iii) administration of fresh frozen plasma (FFP), prothrombin complex concentrates (PCC), activated PCC (APCC), such as, factor VIII inhibitor, and/or recombinant activated factor VII (rfVIIa). In specific aspects, such methods optionally comprise administering tranexamic acid.

In specific aspects, provided herein is a method for reversing the anticoagulant effect of an anti-FXI antibody or antigen-binding fragment described herein (e.g., antibody AM1, AM2, AM3, or AM4) in a patient being treated with the anti-FXI/FXIa antibody or antigen-binding fragment thereof, comprising administering an effective amount of an anti-idiotype antibody or fragment thereof that specifically binds to the anti-FXI antibody, and optionally, administering an effective amount of fresh frozen plasma (FFP), and optionally tranexamic acid.

In specific aspects, provided herein is a method for reversing the anticoagulant effect of an anti-FXI antibody or antigen-binding fragment described herein, such as antibody AM4, in a patient being treated with the anti-FXI/FXIa antibody or antigen-binding fragment thereof, comprising administering an effective amount of an anti-idiotype antibody (e.g., anti-AM4 antibody) or fragment thereof that specifically binds to the anti-FXI antibody, and optionally, administering an effective amount of recombinant activated factor VII (rfVIIa), and optionally tranexamic acid.

In particular aspects, anti-idiotype antibodies can be produced by various methods described previously, see, e.g., Pan et al., 1995, FASEB J. 9:43-49. Anti-idiotype antibodies are elicited by an antibody molecule (e.g., antibody AM1, AM2, AM3, or AM4) and are directed against antigenic determinants in or close to the antibody's combining site (idiotope). Anti-idiotype antibodies recognize antigenic determinants that overlap a portion of the combining site that is in contact with the original antigen and they can mimic the eliciting antigen.

Pharmaceutical Compositions

The present disclosure provides pharmaceutical compositions comprising the FXI/FXIa-binding antibodies (intact or binding fragments) formulated together with a pharmaceutically acceptable carrier. The compositions can additionally contain one or more other therapeutic agents that are suitable for treating or preventing, for example, thromboembolic disorders (e.g., thrombotic disorders). Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present disclosure can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

In particular aspects, anti-FXI/FXIa antibodies described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) are formulated at approximately 75 mg/1 mL to approximately 200 mg/1 mL concentration, in liquid vials for subcutaneous injections. In particular embodiments, the pharmaceutical composition comprises a pharmaceutical carrier or excipient, for example, sucrose, and polysorbate 20. In particular embodiments, the pharmaceutical composition comprises L-histidine and/or histidine HCl monohydrate. In certain embodiments, the pharmaceutical composition has a pH of approximately 4 to 7, or 5 to 6.

In particular aspects, anti-FXI antibodies described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) are formulated at 150 mg/1 mL concentration, in liquid vials for subcutaneous injections. In one embodiment, the 150 mg/mL liquid formulation contains 150 mg anti-FXI antibody, L-histidine, histidine HCl monohydrate, sucrose, and polysorbate 20, with a pH=5.5±0.5. The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the present disclosure can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the FXIa-binding antibody is employed in the pharmaceutical compositions of the present disclosure. The FXIa-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present disclosure can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present disclosure employed, thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician can start doses of the antibodies of the present disclosure employed in the pharmaceutical composition at levels lower than that required to achieve the desired therapeutic effect and gradually increase the dosage until the desired effect is achieved. In general, effective doses of the compositions of the present disclosure, for the treatment of a thrombotic and/or thromboembolic disorders described herein vary depending upon many different factors, including means of administration, target site, physiological state of the patient, other medications administered, and whether treatment is prophylactic or therapeutic. Treatment dosages need to be titrated to optimize safety and efficacy. For systemic administration with an antibody, the dosage ranges from about 0.01 to 15 mg/kg of the host body weight. For administration with an antibody, the dosage may range from 0.1 mg to 5 mg. For example, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, or 5.0 mg/kg. An exemplary treatment regime entails systemic administration once per every two weeks or once a month or once every 3 to 6 months. An exemplary treatment regime entails systemic administration once per week, once per every two weeks, once a month, or once every 3 to 6 months, or as needed (PRN).

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c., at a dose of 3 mg/kg. In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c., at a dose of 10 mg/kg. In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c., at a dose of 30 mg/kg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c., at a dose of 50 mg/kg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c., at a dose of 100 mg/kg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c. route, at a dose in the range of 5 mg to 600 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c. route, at a dose of approximately 5 mg, 10 mg, 15 mg, 20 mg, 30 mg, 40 mg, 50 mg, 60 mg, 90 mg, 100 mg, 120 mg, 150 mg, 180 mg, 200 mg, 210 mg, 240 mg, 250 mg, 270 mg, 300 mg, 330 mg, 350 mg, 360 mg, 390 mg, 400 mg, 420 mg, 450 mg, 480 mg, 500 mg, 510 mg, 540 mg, 550 mg, 570 mg, or 600 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by s.c. route, at a dose of 5 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by s.c. route, at a dose of 15 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by s.c. route, at a dose of 50 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by s.c. route, at a dose of 150 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by s.c. route, at a dose of 300 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by s.c. route, at a dose of 600 mg.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c. route, at a dose sufficient to achieve a mean duration of aPTT prolongation of 2-fold or greater for a period no longer than 30 days, 35 days, 36 days, 37 days, 38 days, 39 days, 40 days, 41 days, 42 days, 43 days, 44 days, 45 days, or 50 days.

In a certain embodiment, an anti-FXI antibody described herein (e.g., an anti-FXI/FXIa antibody described in Table 2, such as, antibody AM1, AM2, AM3, or AM4 or anti-FXI/FXIa antibodies comprising VL CDRs and VH CDRs of antibody AM1, AM2, AM3, or AM4) is administered, for example by i.v. or s.c. route, at a dose sufficient to achieve a mean duration of aPTT prolongation of 2-fold or greater for a period no longer than 42 days.

In particular aspects, antibody is usually administered on multiple occasions. Intervals between single dosages can be weekly, monthly or yearly. Intervals can also be irregular as indicated by measuring blood levels of FXIa-binding antibody in the patient. In addition alternative dosing intervals can be determined by a physician and administered monthly or as necessary to be efficacious. In some methods of systemic administration, dosage is adjusted to achieve a plasma antibody concentration of 1-1000 µg/ml and in some methods 25-500 µg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the present disclosure but not to limit its scope. Other variants of the present disclosure will be readily apparent to one of ordinary skill in the art and are encompassed by the appended claims.

Example 1

Generation of Affinity Matured Anti-FXI/FXIa Antibodies

Maturation Panning

To increase affinity and biological activity of anti-FXI/FXIa antibody NOV1090 (non-germlined version of NOV1401 and does not contain Fc modifications, such as the D265A and P329A substitutions in a human Fc domain), CDR-L3 and CDR-H2 regions were exchanged in parallel by diversified cassettes/modules (Prassler et al (2009) Immunotherapy; 1(4):571-83) to generate HuCAL PLATINUM@ Maturation Libraries as described below.

For the selection of affinity improved candidates, phage derived candidates from maturation libraries were subjected to two or three rounds of maturation pannings with human FXI, such as the catalytic domain of human FXI (see, e.g., PCT Publication No. WO2016/207858, which is hereby incorporated by reference in its entirety).

Panning stringency was increased by lowering the antigen concentration in each panning round (Low et al (1996) J Mol Biol; 260(3):359-68). In addition to antigen reduction, off-rate selection was performed (Hawkins et al (1992) J Mol Biol; 226(3):889-96) These strategies were combined with prolonged washing steps.

Generation of HuCAL PLATINUM® Maturation Libraries

To generate maturation libraries for NOV1090 CDR-L3 and CDR-H2 regions were optimized by cassette mutagenesis using trinucleotide directed mutagenesis, while the framework regions were kept constant (Virnekäs et al (1994) Nucleic Acids Res; 22(25):5600-7).

The cloning of the maturation libraries was performed in the CysDisplay™ vector encoding for the parental NOV1090 Fab fragment.

For CDR-L3 optimization, a ~400 bp DNA fragment encoding for the CDR-L3, framework 4 as well as the constant region of the light chain were removed from the sequence of the parental antibody by restriction digest and replaced by a repertoire of DNA fragments encoding for diversified CDR-L3 regions together with framework 4 and the constant domain.

For a second library the CDR-H2-encoding sequence was diversified, while the connecting framework regions were kept constant. In order to reduce the background of the parental undiversified sequence a ~150 bp DNA fragment containing the parental CDR-H2 and the framework 3 sequences were replaced by a ~590 bp 'dummy' sequence via restriction digest and ligation, before the diversified CDR-H2 cassette (including framework 3) was inserted by restriction digest and ligation.

Electroporation of ligation mixtures in MC1061F" yielded libraries with a total size of $7.7 \times 10^8$ and $6.7 \times 10^8$ for the HCDR2 and LCDR3 diversification, respectively. Amplification of the library was performed as described previously (Rauchenberger et al (2003) J Biol Chem; 278 (40):38194-205). For quality control, approx. 10-20 single clones per library were randomly picked and sequenced.

Antibodies AM1, AM2, and AM3 were identified from this process. AM4 is a germlined version of AM3 with two amino acid changes at the N-terminus of the light chain (see Table 2).

Example 2

$K_D$ Determination for Anti-FXI/FXIa Fab (NOV1090 Fab) by Solution Equilibrium Titration (SET)

Method Description

Pure fractions of NOV1090 Fab containing at least 90% monomer content, as analyzed by analytical size-exclusion chromatography (SEC) were used for affinity determination by SET.

$K_D$ determination in solution was performed as described (Friguet et al (1985) J Immunol Methods; 77(2):305-19). PubMed PMID: 3981007). In order to improve sensitivity and accuracy of the SET method, it was transferred from classical ELISA to ECL-based technology (Haenel et al (2005) Anal Biochem; 339(1):182-4).

Flag M2 specific antibody (Sigma) at 1 mg/mL labeled with MSD Sulfo-TAG™ NHS-Ester (Meso Scale Discovery, Gaithersburg, MD, USA) according to the manufacturers instructions was used as detection reagent.

Experiments were carried out in polypropylene microtiter plates and with PBS (GIBCO 14190, pH 7.0-7.2) containing 0.5% BSA and 0.02% Tween20 as assay buffer. Serial dilutions of unlabeled FXIa antigen were prepared, starting with a concentration at least 10 times higher than the expected $K_D$. Wells without antigen were used to determine $B_{max}$ values; wells containing only assay buffer were used to determine background. After addition of an appropriate amount of binder (antibody concentration similar to or below the expected $K_D$, 60 µL final volume), the mixture was incubated over night at RT.

MSD plates were coated with 1 µg/mL human plasma derived FXIa (30 µL per well). After washing the plate with PBS containing 0.05% Tween 20, the equilibrated samples were transferred to the plates and incubated for 20 min. Following incubation, 30 µL per well of the MSD-Sulfo-tag labeled detection antibody (anti-Flag M2 (Sigma) 1:2,000) was added to the washed MSD plate and incubated for 30 min at RT on an Eppendorf shaker (700 rpm).

After washing the MSD plate and adding 30 µL/well MSD Read Buffer T with surfactant, electrochemiluminescence signals were detected using a Sector Imager 6000 (Meso Scale Discovery, Gaithersburg, MD, USA).

Data were evaluated with XLfit (IDBS) software applying customized fitting models. The fit model according to (Haenel et al (2005) Anal Biochem; 339(1):182-4) and modified according to Abraham et al (Abraham et al (1996) J Mol Recognit; 9(5-6):456-61) was used for $K_D$ determination of NOV1090 Fab.

Results

The $K_D$ of NOV1090 Fab was determined to be approximately 210±120 µM by SET (Table 3). This value is consistent with a $K_D$ of 305±8 µM determined for the closely related NOV1401 Fab with identical CDRs (see Table 1).

TABLE 3

Assay Conditions and Results of SET $K_D$ determination for NOV1090 Fab

| | |
|---|---|
| Conc. Fab [pM] | 500 |
| hFXIa highest conc [pM] | 2.5 E+05 |
| hFXIa lowest conc above 0 [pM] | 3.9 E+03 |
| $K_D$ result ± 95% confidence interval of fit [pM] | 210 ± 120 |

Example 3

$K_D$ Estimation by SET Screening after Affinity Maturation

Method Description

To estimate Fab $K_D$s, bacterial lysates were screened by SET. The SET screening method (see, e.g., Della Ducata et al (2015) J Biomol Screen; 20(10):1256-67) was generally performed as described above for the SET determination method. For ranking of the matured binders by SET based on the principles described by Haenel and coworkers (Haenel et al (2005) Anal Biochem; 339(1):182-4), a constant amount of diluted BEL extract (bacterial lysate) was equilibrated over night with different concentrations of antigen.

The mixture was then transferred to MSD plates, which were previously coated with antigen (1 µg/mL human plasma FXIa), and after incubation and washing, a suitable MSD-Sulfo-tag labeled detection antibody was added (anti-Flag M2, Sigma).

Subsequently, the concentration of unbound Fab was quantified via ECL detection (ECL-labeled anti-human (Fab)2, Dianova) using the Sector Imager 6000 (Meso Scale Discovery, Gaithersburg, MD, USA), using standard MSD plates coated with anti-His specific antibody (Jackson).

Results were processed using XLfit (IDBS) software, applying the corresponding fit model as described above to estimate affinities and thus identify clones most improved by maturation.

Results

The SET screening results for three affinity matured FXIa antibody Fabs derived from NOV1090 as described in Example 1 are summarized in Table 4. The approximately 7× lower $K_D$ values for all three Fabs indicate that the affinity maturation pannings were successful in generating higher affinity antibodies.

Please note that the SET screening results represent $K_D$ estimates rather than exact $K_D$ values as they are generated from only 5 data points (1 quantification, 4 specific titration) with unpurified Fab samples compared to full titration experiments with purified samples for exact $K_D$ determination by SET. However, $K_D$ results are generally comparable within some reasonable variation (see Della Ducata et al (2015) J Biomol Screen; 20(10):1256-67).

TABLE 4

Assay Conditions and Results of $K_D$ estimation for anti-FXI/FXIa Fabs by SET screening

| | AM1 | AM2 | AM3 |
|---|---|---|---|
| Conc. Fab [pM] | 14 | 3 | 1 |
| hFXIa highest conc [pM] | 200 | 200 | 200 |
| hFXIa lowest conc above 0 [pM] | 2 | 2 | 2 |
| $K_D$ result ±95% confidence interval of fit [pM] | 32 ± 24 | 27 ± 38 | 29 ± 24 |

Example 4

ELISA Binding Profiles of Affinity Matured Anti-FXI/FXIa IgGs

ELISA techniques have been used to characterize the purified affinity matured IgGs, namely to evaluate binding to human FXIa, human FXI, cyno FXI, and rabbit FXI, as well as to human kallikrein and pre-kallikrein.

Method Description

Optimal antigen and antibody concentrations as well as blocking conditions were evaluated in pre-experiments and settings adjusted accordingly.

For direct coating ELISAs, antigens were immobilized on 384-well Maxisorp™ microtiter plates over night at 4° C. using the concentrations as shown in Table 5. After blocking with 5% skim milk powder in PBS (80 µl/well), 20 µl/well of Fab-containing E. coli lysates or purified antibodies at various concentrations (typically 12 points of a 1:3 titration starting at 200 nM IgG or Fab, respectively) were added to plates and incubated for 1 h at room temperature. Bound antibodies were detected using respective alkaline-phosphatase coupled secondary antibodies (F(ab)2 specific goat anti-human IgG conjugated to alkaline phosphatase (Jackson, Cat #109-055-097, diluted 1:5000 in PBS+0.05% Tween20)) in combination with 'AttoPhos' fluorescence substrate (Roche, #11681982001). Fluorescence emission at 535 nm was recorded with excitation at 430 nm. Multiple wash steps with PBS+0.05% Tween20 were performed in between individual assay steps.

TABLE 5

Antigen concentrations used in ELISA experiments

| Antigen | Concentration |
|---|---|
| Human FXI | 0.2 µg/mL |
| Human FXI | 0.6 µg/mL |
| Human FXI | 1.3 µg/mL |
| Human FXI | 1.7 µg/mL |
| Pre-kallikrein | 3.0 µg/mL |
| Kallikrein | 3.0 µg/mL |

Results

Figure 1B:
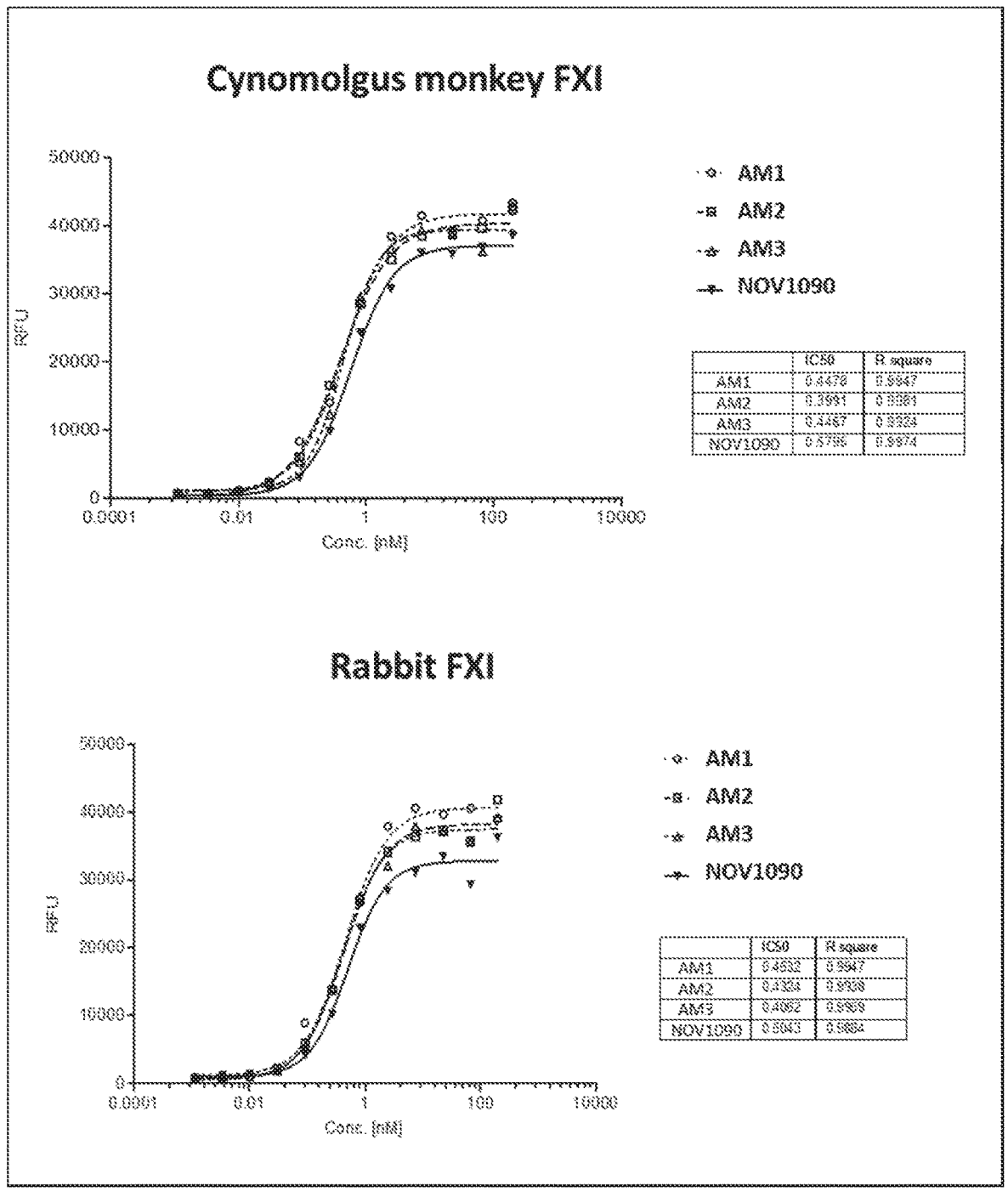
Figure 1C:
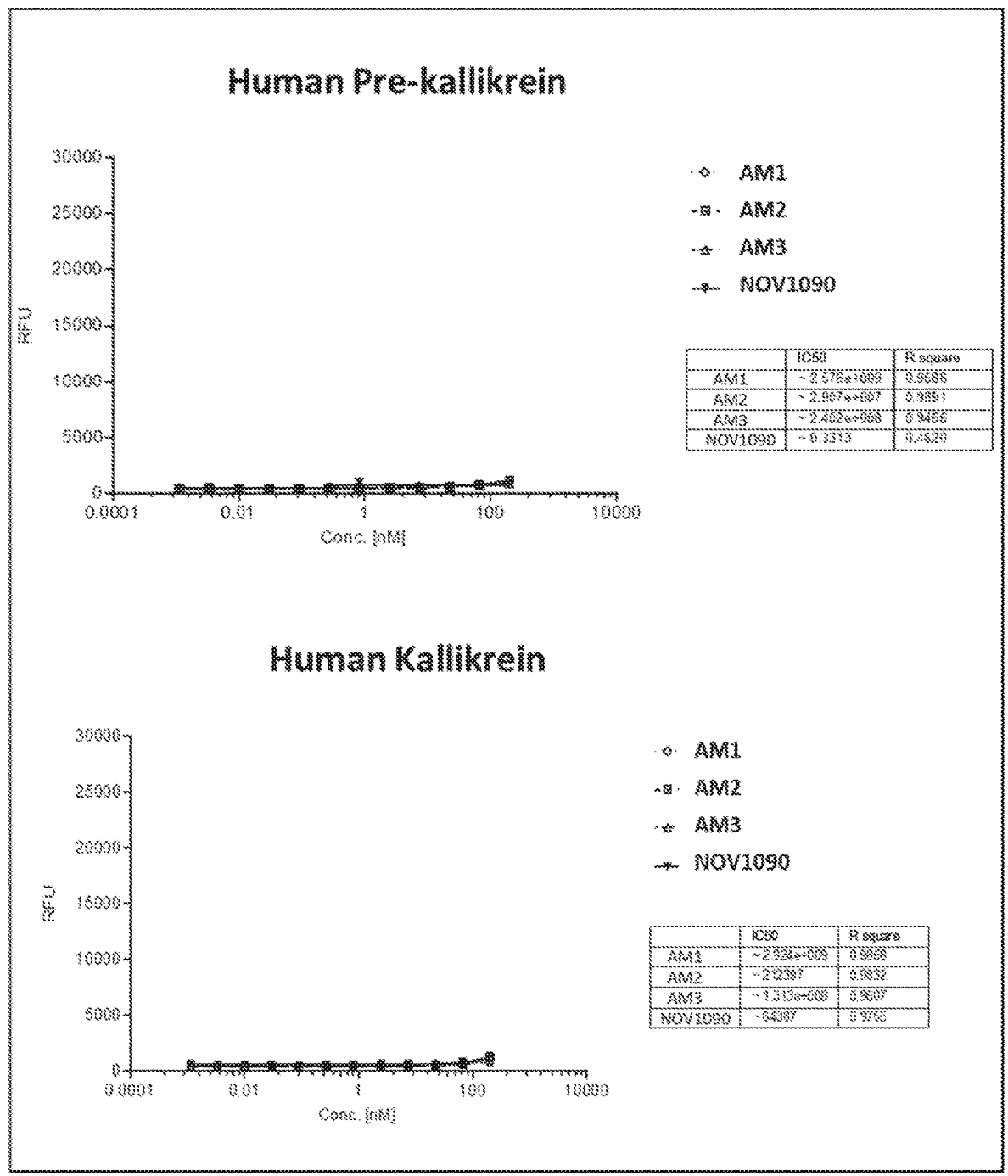

ELISA binding profiles for all three affinity matured IgGs as well as the parental IgG are shown in FIG. 1. All antibodies—parental NOV1090 and three affinity matured variants of NOV1090 (AM1, AM2, AM3)—show specific binding to human FXI and FXIa (FIG. 1A), as well as to cynomolgus monkey and rabbit FXI (FIG. 1B). No binding was detected to human pre-kallikrein and human kallikrein up to 100 nM (FIG. 1C).

Overall ELISA curves for affinity matured antibodies are left shifted compared to NOV1090 and $IC_{50}$ values are lower, especially for binding to human FXIa and FXI. $IC_{50}$ values are more similar between parental and affinity matured variants for cyno and rabbit FXI. Together, ELISA data suggest that affinity maturation increased binding to FXI and FXIa particularly to the human enzyme without introducing non-specific binding to kallikrein, the most closely related enzyme to FXIa.

Example 5

Functional Activity of Affinity Matured Anti-FXI/FXIa IgGs

Anticoagulant activities of three affinity matured antibodies were tested by using the activated partial thromboplastin time (aPTT) assay and the thrombin generation assay (TGA).

aPTT Assay Description

Lyophilized normal human plasma 'Coagulation Control N' (reference no 5020050) was purchased from Technoclone GmbH (Vienna, Austria). It was pooled from citrated plasma of selected healthy donors. The clotting time obtained with this normal plasma reflects normal concentrations of the coagulation factors involved in clotting. The lyophilized plasma was stored at 4° C. Prior to its use, the plasma was re-suspended in 1 mL of distilled water by carefully rotating the vial and then keeping it for 10 minutes at room temperature.

The intrinsic pathway triggering Dapttin® TC (Cat #5035090), a double activated aPTT reagent with sulfatides and silica as surface activators, together with an optimal mixture of highly purified phospholipids, was purchased from Technoclone GmbH (Vienna, Austria), containing phospholipid, sulfatide, and silicate. The lyophilized trigger was reconstituted in distilled water with the volume indicated on the vial.

Calcium Chloride (Fluka, Cat #21115) was prepared in distilled water at a stock concentration of 25 mM. Phosphate Buffered Saline (PBS, Life Technologies, Cat #10010-023) was used as antibody dilution buffer.

The measurements of the clotting time were performed in a ball coagulometer model MC10 (Merlin medical, Germany), which is a semi-automated mechanical clot detection system. The system utilizes a special cuvette in which a stainless steel ball is distributed (Merlin medical, Cat #Z05100).

The cuvette is placed into the measuring well of the ball coagulometer. After the sample, plasma, and trigger are added to the cuvette, the measuring well rotates slowly causing the cuvette to rotate along its longitudinal axis. Because the cuvette is positioned at a slight angle, gravity and inertia always position the ball at the lowest point of the cuvette. Exactly opposite the ball-position is a magnetic sensor. After an appropriate incubation period, a timer is started with the addition of the calcium chloride solution. As coagulation takes place, fibrin strands form in the reaction mixture. The fibrin strands pull the ball away from its inertia position that triggers an impulse in the magnetic sensor. This impulse electronically stops the timer.

Serial dilutions of NOV1090 and affinity matured antibodies (e.g., AM1, AM2, and AM3) were prepared in PBS. The reconstituted human blood plasma, trigger reagent (Dapttin), and calcium chloride were warmed up in a water bath at 37° C. for 10 minutes.

The assay was performed exclusively in specialized cuvettes containing a stainless steel ball. The pipetting scheme is outlined in Table 6.

TABLE 6

Pipetting scheme for measuring antibody activity in aPTT assay

| Assay step | Solution | aPTT assay Volume [μL] |
|---|---|---|
| 1 | antibody dilution or diluent | 50 |
| 2 | human blood plasma | 50 |
| 3 | Dapttin | 50 |
| 4 | | Incubate 3 minutes at 37° C. under rotation |
| 5 | 25 mM Calcium Chloride | 50 |
| 6 | | Immediately start the timer |
| 7 | | The timer stops when the clot is formed |

The samples were measured in duplicates at a temperature of 37° C. in the Merlin ball coagulometer described above.

aPTT Assay Results

Figure 2:
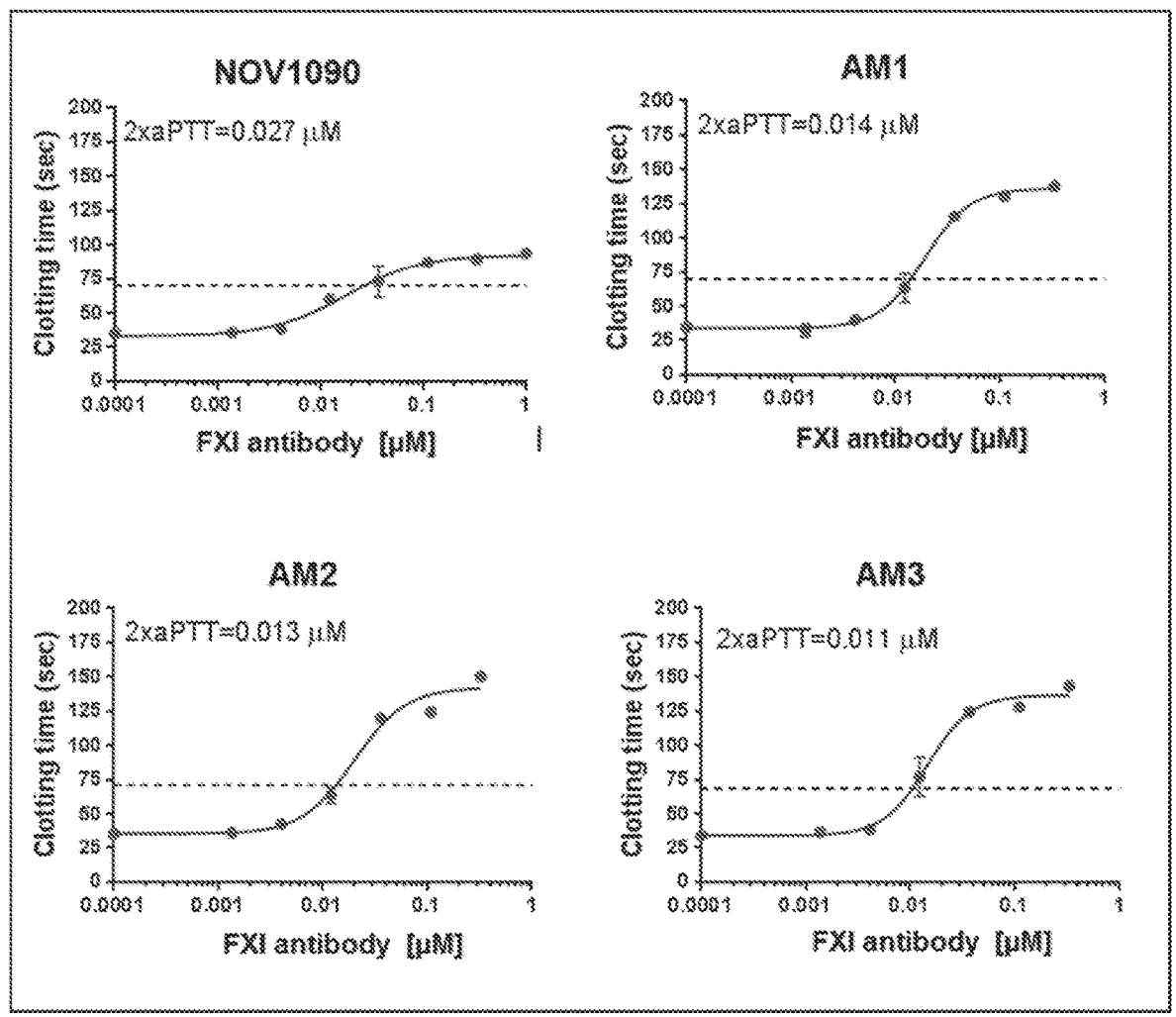
FIG. 2 shows aPTT compound response curves for FXIa antibodies. Representative response curves for three affinity matured antibodies (AM1, AM2, AM3) prolonging coagulation time in the aPTT assay using pooled human plasma are shown. The assay measures the time to coagulation after initiating the intrinsic clotting cascade in presence of different concentrations of antibody, as described in Example 5. The black line represents a fit using a logistics non-linear fit model. The dotted line indicates the antibody concentration at which the clotting time is doubled compared to baseline, i.e. the 2×aPTT value, which is 14 nM, 13 nM and 11 nM for AM1, AM2 and AM3, respectively.

FIG. 2 shows representative response curves for the parental antibody NOV1090 and three affinity matured antibodies (e.g., AM1, AM2, and AM3). All three antibodies showed a concentration dependent prolongation of aPTT clotting times. The aPTT clotting times are doubled compared to baseline at antibody concentrations of 11 to 14 nM. These results are comparable to results achieved with parental NOV1090.

TGA Description

For the TGA, lyophilized normal human plasma (Coagulation control N) was purchased from Technoclone GmbH (Cat #5020040) and reconstituted in distilled water in a volume suggested by the manufacturer.

The substrate solution was prepared using the fluorogenic substrate Z-Gly-Gly-Arg-AMC from Technoclone GmbH (Cat #5006230). Aliquots of the lyophilized substrate were kept at 4° C. The substrate was dissolved freshly in the volume of distilled water indicated on the vial 20 minutes prior its use in the assay. The reconstituted substrate solution contains the fluorogenic peptide at a concentration of 1 mM and $CaCl_2$ at a concentration of 15 mM.

The trigger reagent 'platelet poor plasma (PPP)-reagent low' was purchased from Thrombinoscope (Cat #TS31.00) and reconstituted in distilled water as indicated on the vial. 'PPP-reagent low' contains a mixture of phospholipids and tissue factor at very low concentration. The reagent was 8-fold diluted in 80 mM Tris/HCl at pH7.4, 0.05% (w/v) CHAPS immediately before use.

The samples were aliquoted and measured in 96 well black/clear bottom plates purchased from Costar (product no 3603). For automation transfer samples were placed in V-bottom 96 well plate (Costar, 3894) and transferred using a CyBio automation system (Analytik Jena US, Woburn, MA, USA).

The reconstituted human blood plasma, trigger reagent 'PPP-reagent low' and substrate were pre-warmed for 10 minutes in a water bath at 37° C. Serial 1:3 antibody (e.g. NOV1401, AM1, AM2, and AM3) dilutions in PBS were prepared in a 96 well plate starting with a NOV1401 concentration of 5 μM (5× the highest final concentration of 1 μM) for a total of 8 dilutions. 222 μl of trigger reagent was mixed with 1108 μl of substrate solution to generate the 10+50 trigger reagent substrate mix. 80 μl per well was added into a V-bottom 96 well plate for later transfer using an automation system. The plate was kept at 37° C. The reagents were added according to the scheme given in Table 7.

TABLE 7

Pipetting scheme

| Assay step | Solution | Volume [ul] |
|---|---|---|
| 1 | Antibody solutions (8 dilutions) | 20 |
| 2 | Plasma stock solution | 20 |
| | 5 minutes incubation at 37° C. in a thermomixer at 300 rpm. | |
| 3 | Trigger reagent/substrate mixture | 10 + 50 |

Trigger/substrate mixtures were transferred using automation. After adding the mixtures, excitation and emission at 360 nm at 460 nm, respectively, were recorded immediately using a Synergy Neo instrument (BioTek Instrument Inc., Winooski, VT, USA). The samples were measured in duplicates at a temperature of 37° C. in the plate reader for 90 minutes at intervals of 55 seconds.

To generate peak thrombin concentration values data were processed using the TGA evaluation software file provided by Technoclone. To generate plots for peak thrombin concentration vs antibody concentration data were fit using GraphPad software. These data were fit to a non-linear regression model in the GraphPad Prism5 software (Graph-Pad Software Inc., La Jolla, CA, USA). The IC50 value was determined using the built-in four-parameter dose-response curve equation (variable slope): y=Bottom+(Top−Bottom)/(1+10^((Log IC50−x)*Hillslope)) where y is the maximal concentration of thrombin formed at the inhibitor concentration, x, and top and bottom represent the concentration of thrombin without inhibitor and at the highest concentration of inhibitor, respectively.

TGA Results

Figure 3:
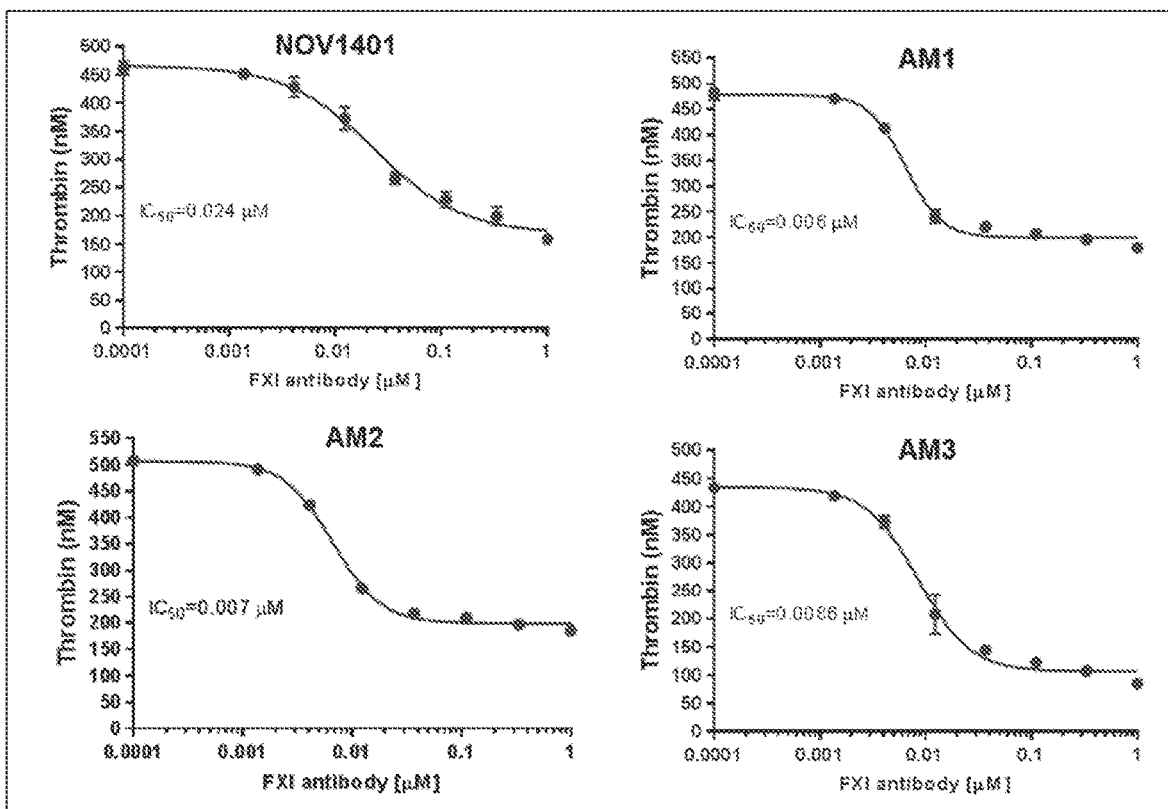
FIG. 3 shows a TGA compound response curves for FXIa antibodies. Representative response curves for three affinity matured antibodies (AM1, AM2, AM3) inhibiting thrombin generation in the TGA with pooled human plasma are shown. The assay measures the effects of different concentrations of NOV1401 on FXI-dependent thrombin generation through the so-called thrombin-*FXIa feed-forward loop that can be triggered by very low tissue factor (TF) concentrations as described in Example 5. The black line represents a fit using a four-parameter dose-response curve model. $IC_{50}$ values of 6 nM, 7 nM, and 9 nM, for AM1, AM2 and AM3, respectively were calculated for these compound response curves.

FIG. 3 shows representative response curves for three affinity matured FXIa antibodies (e.g., AM1, AM2, and AM3) and for comparison NOV1401, which is the germlined version of the parental antibody NOV1090. All three affinity matured antibodies showed a concentration dependent inhibition of thrombin generation in the TGA with about 3-4× lower $IC_{50}$ values compared to NOV1401. $IC_{50}$ values and residual thrombin concentrations were calculated from these response curves and are shown in Table 8.

TABLE 8

Summary of aPTT and TGA data for three affinity matured FXIa antibodies

| Affinity matured antibody | aPTT assay (2× aPTT) [µM] | TGA $IC_{50}$ [µM] | TGA Residual Thrombin [nM] (%) |
|---|---|---|---|
| AM1 | 0.014 | 0.006 | 179.9 (37.5) |
| AM2 | 0.013 | 0.007 | 185.6 (36.6) |
| AM3 | 0.011 | 0.009 | 85.35 (19.7) |
| NOV1090 (aPTT), NOV1401 (TGA) | 0.027 | 0.024 | 158.9 (34.4) |

AM4, which is the germlined version of AM3 (see Table 1), was also subjected to the aPTT assay and the TGA yielding very similar results for aPTT prolongation and $IC_{50}$ values in the TGA compared to AM3.

Example 6

$K_D$ Determination for Affinity Matured Anti-FXI/FXIa IgG (AM4) by Solution Equilibrium Titration (SET)

Figure 4:
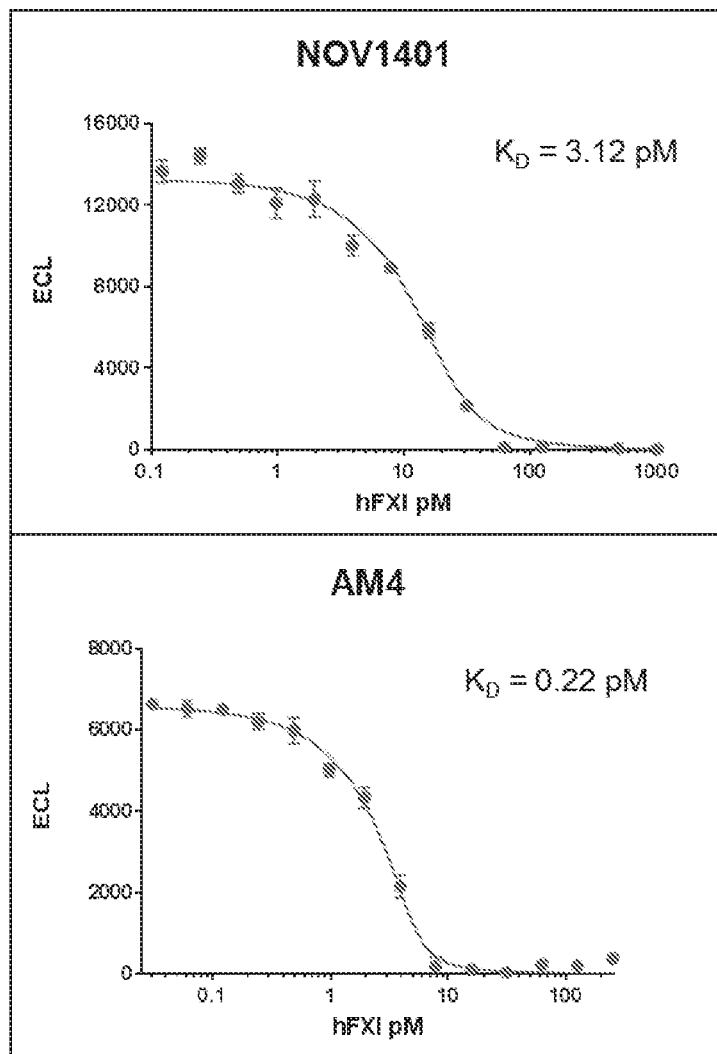
FIG. 4 shows representative binding curves from SET experiments for NOV1401, the germlined version of NOV1090, and AM4, an affinity-matured antibody derived from NOV1090 as described in Examples. $K_D$ values were determined from fitting the experimental data to a 1:1 binding model as described in Examples.

The SET method described in Example 2 was used to determine the $K_D$ for AM4 (IgG), and compared to NOV1401, the germlined version of its parental antibody NOV1090. FIG. 4 shows the dose responses and fitted curves for binding to FXIa for both antibodies and the results are summarized in Table 9.

TABLE 9

Summary of SET results for AM4 and NOV1401

| Antibody | Ab Incubation conc. [pM] | $K_D$ [pM] | R square |
|---|---|---|---|
| NOV1401 (IgG) | 20 | 3.12 | 0.98 |
| AM4 (IgG) | 5 | 0.22 | 0.98 |

These binding data for the full length IgG antibodies suggest that AM4 has an approximately 10× higher affinity than it's parental antibody NOV1090, as the affinities for the closely related NOV1401 and NOV1090 antibodies to FXIa are comparable (data not shown). An approximate 10× increase in affinity was also observed comparing the SET $K_D$ estimates for AM1, AM2 and AM3 with the SET $K_D$ determined for NOV1090 Fab (see Examples 2 and 3).

In summary, these data suggest that anti-FXI/FXIa antibodies AM1, AM2, AM3 and AM4, when compared to parental NOV1090, demonstrate increased binding affinity to FXI and FXIa and at least comparable anticoagulant activities, for example, as determined by aPTT prolongation assay and TGA showing reduction amounts of thrombin. Since antibodies AM1, AM2, AM3, and AM4 share the same CDRs except HCDR2, where they share certain consensus amino acid sequences, for example, SEQ ID NOs: 59 (Combined and Kabat HCDR2), 60 (Chothia HCDR2) or 61 (IMGT HCDT2), these results indicate that similar anti-FXI/FXIa antibodies which share the same HCDR1, HCDR3, LCDR1, LCDR2, and LCDR3, and fall within the consensus amino acid sequences of HCDR2, would also be effective binders and exhibit similar anticoagulant activities.

INCORPORATION BY REFERENCE

All references cited herein, including patents, patent applications (e.g., patent application publications), papers, publications, text books, and the like, and the references cited therein, to the extent that they are not already, are hereby incorporated herein by reference in their entirety.

EQUIVALENTS

The foregoing written specification is considered to be sufficient to enable one skilled in the art to practice the present disclosure. It will be appreciated, however, that no matter how detailed the foregoing may appear in text, the present disclosure may be practiced in many ways and the present disclosure should be construed in accordance with the appended claims and any equivalents thereof.

The invention claimed is:

1. A method of treating, managing, or reducing the risk of a thromboembolic disorder in a subject, comprising administering to the subject a dose of 5 mg to 600 mg an isolated antibody or antigen-binding fragment thereof that binds within the catalytic domain of FXI and/or FXIa comprising:
   (a) a heavy chain variable region (VH) comprising complementarity determining regions HCDR1, HCDR2, and HCDR3, and
   (b) a light chain variable region (VL) comprising complementarity determining regions LCDR1, LCDR2, and LCDR3, wherein:
   (i) the HCDR1 comprises the amino acid sequence of SEQ ID NO: 3, the HCDR2 comprises the amino acid sequence of SEQ ID NO: 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18, according to the Combined numbering system;
   (ii) the HCDR1 comprises the amino acid sequence of SEQ ID NO: 6, the HCDR2 comprises the amino acid sequence of SEQ ID NO: 45, the HCDR3 comprises the amino acid sequence of SEQ ID NO: 5, the LCDR1 comprises the amino acid sequence of SEQ ID NO: 16, the LCDR2 comprises the amino acid sequence of SEQ ID NO: 17, and the LCDR3 comprises the amino acid sequence of SEQ ID NO: 18, according to the Kabat numbering system;
   (iii) the HCDR1 comprises the amino acid sequence of SEQ ID NO: 7, the HCDR2 comprises the amino acid sequence of SEQ ID NO: 46, the HCDR3 comprises the amino acid sequence of SEQ ID NO: 5, the LCDR1 comprises the amino acid sequence of SEQ ID NO: 19, the LCDR2 comprises the amino acid sequence of SEQ ID NO: 20, and the LCDR3 comprises the amino acid sequence of SEQ ID NO: 21, according to the Chothia numbering system; or
   (iv) the HCDR1 comprises the amino acid sequence of SEQ ID NO: 9, the HCDR2 comprises the amino acid sequence of SEQ ID NO: 47, the HCDR3 comprises the amino acid sequence of SEQ ID NO: 11, the LCDR1 comprises the amino acid sequence of SEQ ID NO: 22, the LCDR2 comprises the amino acid sequence of SEQ ID NO: 20, and the LCDR3 comprises the amino acid sequence of SEQ ID NO: 18, according to the IMGT numbering system.

2. The method of claim 1, wherein the subject is afflicted with, or is at risk of developing one or more of: a stroke, a stroke associated with deep vein thrombosis, a stroke associated with atrial fibrillation, atrial fibrillation, or a combination thereof.

3. The method according to claim 1, further comprising administering the antibody or antigen-binding fragment to the subject in combination with one or more statin therapies.

4. The method of claim 1, further comprising temporarily reversing an anticoagulant effect for a sufficient time to manage bleeding by one of the following:
   (i) fluid replacement using colloids, crystalloids, human plasma, or plasma proteins;
   (ii) transfusion with packed red blood or whole blood; or
   (iii) administration of fresh frozen plasma (FFP), prothrombin complex concentrates (PCC), activated PCC (APCC), and/or recombinant activated factor VII.

5. The method of claim 4, wherein the plasma proteins comprise albumin.

6. The method of claim 1, wherein the VH comprises the amino acid sequence of SEQ ID NO: 48; and the VL comprises the amino acid sequence of SEQ ID NO: 34.

7. The method of claim 1, wherein the antibody comprises a heavy chain comprising the amino acid sequence of SEQ ID NO: 50; and a light chain comprising the amino acid sequence of SEQ ID NO: 36.

8. The method of claim 1, wherein the VH comprises an amino acid sequence that is at least 90% identical to the amino acid sequence of SEQ ID NO: 48; the VL comprises an amino acid sequence that is at least 90% identical to the amino acid sequence of SEQ ID NO: 34, and wherein the VH does not comprise the amino acid sequence of SEQ ID NO: 12 and the VL does not comprise the amino acid sequence of SEQ ID NO: 23.

9. The method of claim 1, wherein the VH comprises an amino acid sequence that is at least 95% identical to the amino acid sequence of SEQ ID NO: 48; the VL comprises an amino acid sequence that is at least 95% identical to the amino acid sequence of SEQ ID NO: 34, and wherein the VH does not comprise the amino acid sequence of SEQ ID NO: 12 and the VL does not comprise the amino acid sequence of SEQ ID NO: 23.

10. The method of claim 1, wherein the antibody is a monoclonal human antibody or a monoclonal humanized antibody.

11. The method of claim 1, wherein the antibody is a human IgG1, IgG2, or IgG4 isotype antibody.

12. The method of claim 1, wherein the dose is 5 mg, 10 mg, 15 mg, 20 mg, 30 mg, 40 mg, 50 mg, 60 mg, 90 mg, 100 mg, 120 mg, 150 mg, 180 mg, 200 mg, 210 mg, 240 mg, 250 mg, 270 mg, 300 mg, 330 mg, 350 mg, 360 mg, 390 mg, 400 mg, 420 mg, 450 mg, 480 mg, 500 mg, 510 mg, 540 mg, 550 mg, 570 mg, or 600 mg.

13. The method of claim 12, wherein the dose is 150 mg.

14. The method of claim 1, wherein the administration achieves a mean duration of aPTT prolongation of 2-fold or greater for a period of no longer than 50 days.

15. The method of claim 1, wherein the administration achieves a mean duration of aPTT prolongation of 2-fold or greater for a period of no longer than 42 days.

16. The method of claim 1, wherein the antibody or antigen-binding fragment is administered to the subject once a month.

17. The method of claim 1, wherein the antibody or antigen-binding fragment is administered to the subject in a pharmaceutical formulation further comprising L-histidine, histidine HCl monohydrate, sucrose, and polysorbate 20.

18. The method of claim 1, wherein administering comprises administering intravenously or subcutaneously.

* * * * *

SEQUENCE LISTING

```
<160> NUMBER OF SEQ ID NOS: 69

<210> SEQ ID NO 1
<211> LENGTH: 625
<212> TYPE: PRT
<213> ORGANISM: Homo sapiens

<400> SEQUENCE: 1

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
            20                  25                  30
```

-continued

```
Gly Asp Ile Thr Thr Val Phe Thr Pro Ser Ala Lys Tyr Cys Gln Val
             35                  40                  45

Val Cys Thr Tyr His Pro Arg Cys Leu Leu Phe Thr Phe Thr Ala Glu
 50                  55                  60

Ser Pro Ser Glu Asp Pro Thr Arg Trp Phe Thr Cys Val Leu Lys Asp
 65                  70                  75                  80

Ser Val Thr Glu Thr Leu Pro Arg Val Asn Arg Thr Ala Ala Ile Ser
                 85                  90                  95

Gly Tyr Ser Phe Lys Gln Cys Ser His Gln Ile Ser Ala Cys Asn Lys
                100                 105                 110

Asp Ile Tyr Val Asp Leu Asp Met Lys Gly Ile Asn Tyr Asn Ser Ser
             115                 120                 125

Val Ala Lys Ser Ala Gln Glu Cys Gln Glu Arg Cys Thr Asp Asp Val
            130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
    210                 215                 220

Val Ser Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
                245                 250                 255

Leu Lys Thr Ser Glu Ser Gly Leu Pro Ser Thr Arg Ile Lys Lys Ser
            260                 265                 270

Lys Ala Leu Ser Gly Phe Ser Leu Gln Ser Cys Arg His Ser Ile Pro
        275                 280                 285

Val Phe Cys His Ser Ser Phe Tyr His Asp Thr Asp Phe Leu Gly Glu
    290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
            340                 345                 350

Asn Gly Ser Pro Thr Lys Ile Leu His Gly Arg Gly Ile Ser Gly
        355                 360                 365

Tyr Thr Leu Arg Leu Cys Lys Met Asp Asn Glu Cys Thr Thr Lys Ile
    370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
            420                 425                 430

Phe Tyr Gly Val Glu Ser Pro Lys Ile Leu Arg Val Tyr Ser Gly Ile
        435                 440                 445

Leu Asn Gln Ser Glu Ile Lys Glu Asp Thr Ser Phe Phe Gly Val Gln
```

```
                450             455             460
Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
                500                 505                 510

Asp Cys Trp Val Thr Gly Trp Gly Tyr Arg Lys Leu Arg Asp Lys Ile
                515                 520                 525

Gln Asn Thr Leu Gln Lys Ala Lys Ile Pro Leu Val Thr Asn Glu Glu
                530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
                580                 585                 590

Thr Ser Trp Gly Glu Gly Cys Ala Gln Arg Glu Arg Pro Gly Val Tyr
                595                 600                 605

Thr Asn Val Val Glu Tyr Val Asp Trp Ile Leu Glu Lys Thr Gln Ala
                610                 615                 620

Val
625

<210> SEQ ID NO 2
<211> LENGTH: 3278
<212> TYPE: DNA
<213> ORGANISM: Homo sapiens

<400> SEQUENCE: 2
aggcacacag gcaaaatcaa gttctacatc tgtccctgtg tatgtcactt gtttgaatac      60
gaaataaaat taaaaaaata aattcagtgt attgagaaag caagcaattc tctcaaggta     120
tatttctgac atactaagat tttaacgact tcacaaaata tgctgtactg agagagaatg     180
ttacataaca ttgagaacta gtacaagtaa atattaaagt gaagtgacca tttcctacac     240
aagctcattc agaggaggat gaagaccatt ttggaggaag aaaagcaccc ttattaagaa     300
ttgcagcaag taagccaaca aggtcttttc aggatgattt tcttatatca agtggtacat     360
ttcattttat ttacttcagt ttctggtgaa tgtgtgactc agttgttgaa ggacacctgc     420
tttgaaggag gggacattac tacggtcttc acaccaagcg ccaagtactg ccaggtagtc     480
tgcacttacc acccaagatg tttactcttc actttcacgg cggaatcacc atctgaggat     540
cccacccgat ggtttacttg tgtcctgaaa gacagtgtta cagaaacact gccaagagtg     600
aataggacag cagcgatttc tgggtattct ttcaagcaat gctcacacca ataagcgct      660 tgcaacaaag acatttatgt ggacctagac atgaagggca taaactataa cagctcagtt     720
gccaagagtg ctcaagaatg ccaagaaaga tgcacggatg acgtccactg ccactttttc     780
acgtacgcca caaggcagtt tcccagcctg gagcatcgta acatttgtct actgaagcac     840
acccaaacag ggacaccaac cagaataacg aagctcgata aagtggtgtc tggattttca     900
ctgaaatcct gtgcactttc taatctggct tgtattaggg acattttccc taatacggtg     960
tttgcagaca gcaacatcga cagtgtcatg ctcccgatg cttttgtctg tggccgaatc    1020
tgcactcatc atcccggttg cttgttttt accttctttt cccaggaatg ccccaaagaa    1080
```

| | |
|---|---|
| tctcaaagaa atctttgtct ccttaaaaca tctgagagtg gattgcccag tacacgcatt | 1140 |
| aaaaagagca aagctctttc tggtttcagt ctacaaagct gcaggcacag catcccagtg | 1200 |
| ttctgccatt cttcatttta ccatgacact gatttcttgg gagaagaact ggatattgtt | 1260 |
| gctgcaaaaa gtcacgaggc ctgccagaaa ctgtgcacca atgccgtccg ctgccagttt | 1320 |
| tttacctata ccccagccca agcatcctgc aacgaaggga agggcaagtg ttacttaaag | 1380 |
| ctttcttcaa acggatctcc aactaaaata cttcacggga gaggaggcat ctctggatac | 1440 |
| acattaaggt tgtgtaaaat ggataatgag tgtaccacca aaatcaagcc caggatcgtt | 1500 |
| ggaggaactg cgtctgttcg tggtgagtgg ccgtggcagg tgaccctgca cacaacctca | 1560 |
| cccactcaga gacacctgtg tggaggctcc atcattggaa accagtggat attaacagcc | 1620 |
| gctcactgtt tctatggggt agagtcacct aagattttgc gtgtctacag tggcatttta | 1680 |
| aatcaatctg aaataaaaga ggacacatct ttctttgggg ttcaagaaat aataatccat | 1740 |
| gatcagtata aaatggcaga aagcgggtat gatattgcct tgttgaaact ggaaaccaca | 1800 |
| gtgaattaca cagattctca acgacccata tgcctgcctt ccaaaggaga tagaaatgta | 1860 |
| atatacactg attgctgggt gactggatgg gggtacagaa aactaagaga caaaatacaa | 1920 |
| aatactctcc agaaagccaa gatacccta gtgaccaacg aagagtgcca gaagagatac | 1980 |
| agaggacata aaataaccca taagatgatc tgtgccggct acagggaagg agggaaggac | 2040 |
| gcttgcaagg gagattcggg aggccctctg tcctgcaaac acaatgaggt ctggcatctg | 2100 |
| gtaggcatca cgagctgggg cgaaggctgt gctcaaaggg agcggccagg tgtttacacc | 2160 |
| aacgtggtcg agtacgtgga ctggattctg gagaaaactc aagcagtgtg aatgggttcc | 2220 |
| caggggccat tggagtccct gaaggaccca ggatttgctg ggagagggtg ttgagttcac | 2280 |
| tgtgccagca tgcttcctcc acagtaacac gctgaagggg cttggtgttt gtaagaaaat | 2340 |
| gctagaagaa aacaaactgt cacaagttgt tatgtccaaa actcccgttc tatgatcgtt | 2400 |
| gtagtttgtt tgagcattca gtctctttgt ttttgatcac gcttctatgg agtccaagaa | 2460 |
| ttaccataag gcaatatttc tgaagattac tatataggca gatatagcag aaaataacca | 2520 |
| agtagtggca gtggggatca ggcagaagaa ctggtaaaag aagccaccat aaatagattt | 2580 |
| gttcgatgaa agatgaaaac tggaagaaag gagaacaaag acagtcttca ccattttgca | 2640 |
| ggaatctaca ctctgcctat gtgaacacat ttcttttgta aagaaagaaa ttgattgcat | 2700 |
| ttaatggcag attttcagaa tagtcaggaa ttcttgtcat ttccatttta aaatatatat | 2760 |
| taaaaaaaat cagttcgagt agacacgagc taagagtgaa tgtgaagata acagaatttc | 2820 |
| tgtgtggaag aggattacaa gcagcaattt acctggaagt gataccttag ggcaatctt | 2880 |
| gaagatacac tttcctgaaa atgatttgt gatggattgt atatttattt aaaatatctt | 2940 |
| gggaggggag gctgatggag ataggagca tgctcaaacc tccctaagac aagctgctgc | 3000 |
| tgtgactatg ggctcccaaa gagctagatc gtatatttat ttgacaaaaa tcaccataga | 3060 |
| ctgcatccat actacagaga aaaacaatt agggcgcaaa tggatagtta cagtaaagtc | 3120 |
| ttcagcaagc agctgcctgt attctaagca ctgggatttt ctgtttcgtg caaatattta | 3180 |
| tctcattatt gttgtgatct agttcaataa cctagaattt gaattgtcac cacatagctt | 3240 |
| tcaatctgtg ccaacaacta tacaattcat caagtgtg | 3278 |

<210> SEQ ID NO 3
<211> LENGTH: 10
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 3

Gly Phe Thr Phe Ser Thr Ala Ala Met Ser
1               5                   10

<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Ile Ser Gly Ser Gly Ser Ser Thr Tyr Tyr Ala Asp Ser Val Lys
1               5                   10                  15

Gly

<210> SEQ ID NO 5
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Leu Ser Tyr Leu Tyr Ser Gly Tyr Tyr Phe Asp Tyr
1               5                   10

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Thr Ala Ala Met Ser
1               5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Phe Thr Phe Ser Thr Ala
1               5

<210> SEQ ID NO 8
<211> LENGTH: 6
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 8

Ser Gly Ser Gly Ser Ser
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Phe Thr Phe Ser Thr Ala Ala
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ile Ser Gly Ser Gly Ser Ser Thr
1               5

<210> SEQ ID NO 11
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ala Arg Glu Leu Ser Tyr Leu Tyr Ser Gly Tyr Tyr Phe Asp Tyr
1               5                   10                  15

<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120
```

<210> SEQ ID NO 13
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
caggtgcagc tgctggaatc aggcggcgga ctggtgcagc ctggcggtag cctgagactg      60
agctgcgctg ctagtggctt cacctttagc accgccgcta tgagctgggt tcgacaggcc     120
ccagggaaag gcctcgagtg ggtctcaggg attagcggta gcggctctag cacctactac     180
gccgatagcg tgaagggccg gttcactatc tctaggata  actctaagaa cacccctgtac    240 ctgcagatga atagcctgag agccgaggac accgccgtct actactgcgc tagagagctg     300
agctacctgt atagcggcta ctacttcgac tactggggtc aaggcaccct ggtcaccgtg     360
tctagc                                                                366
```

<210> SEQ ID NO 14
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

165                 170                 175
Ala Val Leu Gln Ser Ser Gly Leu Tyr Ser Leu Ser Val Val Thr
            180                 185                 190

Val Pro Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Ala Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Ala Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 15
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
caggtgcagc tgctggaatc aggcggcgga ctggtgcagc ctggcggtag cctgagactg    60
agctgcgctg ctagtggctt cacctttagc accgccgcta tgagctgggt tcgacaggcc   120
ccagggaaag gcctcgagtg gtctcaggg attagcggta gcggtctag cacctactac   180 gccgatagcg tgaagggccg gttcactatc tctagggata actctaagaa caccctgtac   240
ctgcagatga atagcctgag agccgaggac accgccgtct actactgcgc tagagagctg   300
agctacctgt atagcggcta ctacttcgac tactgggtc aaggcaccct ggtcaccgtg   360

```
tctagcgcta gcactaaggg cccctccgtg ttccctctgg cccttccag caagtctacc    420 tccggcggca cagctgctct gggctgcctg gtcaaggact acttccctga gcctgtgaca    480
gtgtcctgga actctggcgc cctgacctct ggcgtgcaca ccttccctgc cgtgctgcag    540
tcctccggcc tgtactccct gtcctccgtg gtcacagtgc cttcaagcag cctgggcacc    600
cagacctata tctgcaacgt gaaccacaag ccttccaaca ccaaggtgga caagcgggtg    660
gagcctaagt cctgcgacaa gacccacacc tgtcctccct gccctgctcc tgaactgctg    720
ggcggccctt ctgtgttcct gttccctcca aagcccaagg acaccctgat gatctcccgg    780
acccctgaag tgacctgcgt ggtggtggcc gtgtcccacg aggatcctga agtgaagttc    840
aattggtacg tggacggcgt ggaggtgcac aacgccaaga ccaagcctcg ggaggaacag    900
tacaactcca cctaccgggt ggtgtccgtg ctgaccgtgc tgcaccagga ctggctgaac    960
ggcaaagagt acaagtgcaa agtctccaac aaggccctgg ccgcccctat cgaaaagaca   1020
atctccaagg ccaagggcca gcctagggaa cccagggtgt acaccctgcc acccagccgg   1080
gaggaaatga ccaagaacca ggtgtccctg acctgtctgg tcaagggctt ctacccttcc   1140
gatatcgccg tggagtggga gtctaacggc agcctgagaa caactacaa gaccacccct   1200 cctgtgctgg actccgacgg ctccttcttc ctgtactcca aactgaccgt ggacaagtcc   1260
cggtggcagc agggcaacgt gttctcctgc tccgtgatgc acgaggccct gcacaaccac   1320
tacacccaga gtccctgtc cctgtctccc ggcaag                              1356
```

```
<210> SEQ ID NO 16
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ser Gly Ser Ser Ser Asn Ile Gly Ser Asn Asp Val Ser
1               5                   10

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Lys Asn Tyr Asn Arg Pro Ser
1               5

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Ala Trp Asp Gln Arg Gln Phe Asp Val Val
1               5                   10
```

```
<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Ser Ser Asn Ile Gly Ser Asn Asp
1               5

<210> SEQ ID NO 20
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Lys Asn Tyr
1

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Trp Asp Gln Arg Gln Phe Asp Val
1               5

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Ser Asn Ile Gly Ser Asn Asp
1               5

<210> SEQ ID NO 23
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

Asp Val Ser Trp Tyr Gln Gln Leu Pro Gly Thr Ala Pro Lys Leu Leu
            35                  40                  45

Ile Tyr Lys Asn Tyr Asn Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ser Ala Trp Asp Gln Arg Gln
            85                  90                  95

Phe Asp Val Val Phe Gly Gly Gly Thr Lys Leu Thr Val Leu
            100                 105                 110

<210> SEQ ID NO 24
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
cagtcagtcc tgactcagcc ccctagcgct agtggcaccc ctggtcaaag agtgactatt      60
agctgtagcg gctctagctc taatatcggc tctaacgacg tcagctggta tcagcagctg     120
cccggcaccg cccctaagct gctgatctat aagaactata ataggcctag cggcgtgccc     180
gataggttta gcggatctaa atcagggact tctgctagtc tggctattag cggcctgcag     240
tcagaggacg aggccgacta ctactgtagc gcctgggatc agcgtcagtt cgacgtggtg     300
ttcggcggag gcactaagct gaccgtgctg                                      330

<210> SEQ ID NO 25
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
            20                  25                  30

Asp Val Ser Trp Tyr Gln Gln Leu Pro Gly Thr Ala Pro Lys Leu Leu
            35                  40                  45

Ile Tyr Lys Asn Tyr Asn Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ser Ala Trp Asp Gln Arg Gln
            85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys

```
                145                 150                 155                 160
Ala Gly Val Glu Thr Thr Thr Pro Ser Lys Gln Ser Asn Asn Lys Tyr
                    165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215
```

<210> SEQ ID NO 26
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
cagtcagtcc tgactcagcc ccctagcgct agtggcaccc ctggtcaaag agtgactatt      60
agctgtagcg gctctagctc taatatcggc tctaacgacg tcagctggta tcagcagctg     120
cccggcaccg cccctaagct gctgatctat aagaactata ataggcctag cggcgtgccc     180
gataggttta gcggatctaa atcagggact tctgctagtc tggctattag cggcctgcag     240
tcagaggacg aggccgacta ctactgtagc gcctgggatc agcgtcagtt cgacgtggtg     300
ttcggcggag gcactaagct gaccgtgctg ggtcaaccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca caagtacgc cgccagcagc      540
tacctgagcc tgacccccga gcagtggaag agccacaggt cctacagctg ccaggtgacc     600
cacgagggca gcaccgtgga aaagaccgtg gccccaaccg agtgcagc                  648
```

<210> SEQ ID NO 27
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

```
Thr Ile Asp Ser Trp Gly Asp Asp Thr Asp Tyr Ala Asp Ser Val Lys
1               5                   10                  15

Gly
```

<210> SEQ ID NO 28
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

```
Asp Ser Trp Gly Asp Asp
1               5
```

```
<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ile Asp Ser Trp Gly Asp Asp Thr
1               5

<210> SEQ ID NO 30
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Asp Ser Trp Gly Asp Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120

<210> SEQ ID NO 31
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
caggtgcaat tgctggaaag cggcggtggc ctggtgcagc cgggtggcag cctgcgtctg      60
agctgcgcgg cgtccggatt caccttttct actgctgcta tgtcttgggt gcgccaggcc     120
ccgggcaaag gtctcgagtg gtttccact atcgactctt ggggcgacga cactgactat      180
gcggatagcg tgaaaggccg ctttaccatc agccgcgata attcgaaaaa caccctgtat     240
ctgcaaatga acagcctgcg tgcggaagat acggccgtgt attattgcgc gcgtgaactg     300
tcttacctgt actctggtta ctacttcgat tactggggcc aaggcaccct ggtgactgtt     360
agctca                                                               366
```

-continued

```
<210> SEQ ID NO 32
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Asp Ser Trp Gly Asp Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 33
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
caggtgcaat tgctggaaag cggcggtggc ctggtgcagc cgggtggcag cctgcgtctg      60
agctgcgcgg cgtccggatt caccttttct actgctgcta tgtcttgggt gcgccaggcc     120
ccgggcaaag gtctcgagtg gtttccact atcgactctt ggggcgacga cactgactat      180
gcggatagcg tgaaaggccg ctttaccatc agccgcgata attcgaaaaa caccctgtat     240
ctgcaaatga acagcctgcg tgcggaagat acggccgtgt attattgcgc gcgtgaactg     300
tcttacctgt actctggtta ctacttcgat tactggggcc aaggcaccct ggtgactgtt     360
agctcagcct ccaccaaggg tccatcggtc ttccccctgg cacccctcctc caagagcacc     420 tctgggggca gcggccct gggctgcctg gtcaaggact acttcccga accggtgacg      480 gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaagcagcg     720
gggggaccgt cagtcttcct cttccccca aaacccaagg acaccctcat gatctcccgg      780 accccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgggt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gaggagatga ccaagaacca ggtcagcctg acctgcctgg tcaaaggctt ctatcccagc    1140
gacatcgccg tggagtggga gagcaatggg cagccggaga caactacaa gaccacgcct    1200 cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356

<210> SEQ ID NO 34
```

```
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34
```

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110

```
<210> SEQ ID NO 35
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
```

| | | |
|---|---|---|
| gatatcgtgc tgacccagcc gccgagcgtg agcggtgcac cgggccagcg cgtgaccatt | 60 |
| agctgtagcg gcagcagcag caacattggt tctaacgacg tgtcttggta ccagcagctg | 120 |
| ccgggcacgg cgccgaaact gctgatctac aaaaactaca accgcccgag cggcgtgccg | 180 |
| gatcgcttta gcggatccaa aagcggcacc agcgccagct ggcgattac cggcctgcaa | 240 |
| gcagaagacg aagcggatta ttactgctct gcttgggacc agcgtcagtt cgacgttgtg | 300 |
| tttggcggcg gcacgaagtt aaccgtccta | 330 |

```
<210> SEQ ID NO 36
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36
```

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

```
Gly Ser Lys Ser Gly Thr Ser Ala Ser Leu Ala Ile Thr Gly Leu Gln
 65                  70                  75                  80

Ala Glu Asp Glu Ala Asp Tyr Tyr Cys Ser Ala Trp Asp Gln Arg Gln
                 85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 37
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
gatatcgtgc tgacccagcc gccgagcgtg agcggtgcac cgggccagcg cgtgaccatt    60
agctgtagcg gcagcagcag caacattggt tctaacgacg tgtcttggta ccagcagctg   120
ccgggcacgg cgccgaaact gctgatctac aaaaactaca accgcccgag cggcgtgccg   180
gatcgcttta gcggatccaa aagcggcacc agcgccagcc tggcgattac cggcctgcaa   240
gcagaagacg aagcggatta ttactgctct gcttgggacc agcgtcagtt cgacgttgtg   300
tttggcggcg gcacgaagtt aaccgtccta ggtcagccca aggctgcccc ctcggtcact   360
ctgttcccgc cctcctctga ggagcttcaa gccaacaagg ccacactggt gtgtctcata   420
agtgacttct acccgggagc cgtgacagtg gcctggaagg cagatagcag ccccgtcaag   480
gcgggagtgg agaccaccac accctccaaa caaagcaaca caagtacgc ggccagcagc   540
tatctgagcc tgacgcctga gcagtggaag tcccacagaa gctacagctg ccaggtcacg   600
catgaaggga gcaccgtgga agacagtgtg ccccctacag aatgttca                648
```

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Ser Ile Glu Tyr Tyr Asp Thr Asp Thr His Tyr Ala Asp Ser Val Lys
 1               5                  10                  15
```

Gly

<210> SEQ ID NO 39
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Glu Tyr Tyr Asp Thr Asp
1               5

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ile Glu Tyr Tyr Asp Thr Asp Thr
1               5

<210> SEQ ID NO 41
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Ser Ile Glu Tyr Tyr Asp Thr Asp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser
        115                 120

<210> SEQ ID NO 42
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42

```
caggtgcaat tgctggaaag cggcggtggc ctggtgcagc cgggtggcag cctgcgtctg      60
agctgcgcgg cgtccggatt cacctttttct actgctgcta tgtcttgggt gcgccaggcc    120
ccgggcaaag gtctcgagtg ggtttcctct atcgaatact acgacactga cactcattat    180
gcggatagcg tgaaaggccg ctttaccatc agccgcgata attcgaaaaa cacccctgtat   240 ctgcaaatga acagcctgcg tgcggaagat acggccgtgt attattgcgc gcgtgaactg    300
tcttacctgt actctggtta ctacttcgat tactggggcc aaggcaccct ggtgactgtt    360
agctca                                                                366
```

<210> SEQ ID NO 43
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Ser Ile Glu Tyr Tyr Asp Thr Asp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
```

|   |   |   | 275 |   |   | 280 |   |   | 285 |   |   |
|---|---|---|---|---|---|---|---|---|---|---|---|

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                    325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 44
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

| caggtgcaat | tgctggaaag | cggcggtggc | ctggtgcagc | cgggtggcag | cctgcgtctg | 60 |
| agctgcgcgg | cgtccggatt | cacctttttct | actgctgcta | tgtcttgggt | gcgccaggcc | 120 |
| ccgggcaaag | gtctcgagtg | ggtttcctct | atcgaatact | acgacactga | cactcattat | 180 |
| gcggatagcg | tgaaaggccg | ctttaccatc | agccgcgata | attcgaaaaa | cacccctgtat | 240 |
| ctgcaaatga | acagcctgcg | tgcggaagat | acggccgtgt | attattgcgc | gcgtgaactg | 300 |
| tcttacctgt | actctggtta | ctacttcgat | tactgggggcc | aaggcaccct | ggtgactgtt | 360 |
| agctcagcct | ccaccaaggg | tccatcggtc | ttccccctgg | caccctcctc | caagagcacc | 420 |
| tctgggggca | gcggccct | gggctgcctg | gtcaaggact | acttcccga | accggtgacg | 480 |
| gtgtcgtgga | actcaggcgc | cctgaccagc | ggcgtgcaca | ccttcccggc | tgtcctacag | 540 |
| tcctcaggac | tctactccct | cagcagcgtg | gtgaccgtgc | cctccagcag | cttgggcacc | 600 |
| cagacctaca | tctgcaacgt | gaatcacaag | cccagcaaca | ccaaggtgga | caagagagtt | 660 |
| gagcccaaat | cttgtgacaa | aactcacaca | tgcccaccgt | gcccagcacc | tgaagcagcg | 720 |
| gggggaccgt | cagtcttcct | cttccccccca | aaacccaagg | acaccctcat | gatctcccgg | 780 |
| acccctgagg | tcacatgcgt | ggtggtggac | gtgagccacg | aagaccctga | ggtcaagttc | 840 |
| aactggtacg | tggacggcgt | ggaggtgcat | aatgccaaga | caaagccgcg | ggaggagcag | 900 |
| tacaacagca | cgtaccgggt | ggtcagcgtc | ctcaccgtcc | tgcaccagga | ctggctgaat | 960 |

-continued

```
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga caactacaa gaccacgcct    1200 cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                             1356
```

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

```
Thr Ile Glu Tyr Ser Ser Gln Glu Thr Tyr Tyr Ala Asp Ser Val Lys
1               5                   10                  15

Gly
```

<210> SEQ ID NO 46
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

```
Glu Tyr Ser Ser Gln Glu
1               5
```

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

```
Ile Glu Tyr Ser Ser Gln Glu Thr
1               5
```

<210> SEQ ID NO 48
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30
```

```
Ala Met Ser Trp Val Arg Gln Ala Pro Gly Lys Gly Leu Glu Trp Val
         35                  40                  45

Ser Thr Ile Glu Tyr Ser Ser Gln Glu Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Ser Tyr Leu Tyr Ser Gly Tyr Tyr Phe Asp Tyr Trp
             100                 105                 110

Gly Gln Gly Thr Leu Val Thr Val Ser Ser
             115                 120
```

<210> SEQ ID NO 49
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49

```
caggtgcaat tgctggaaag cggcggtggc ctggtgcagc cgggtggcag cctgcgtctg      60
agctgcgcgg cgtccggatt cacctttct actgctgcta tgtcttgggt gcgccaggcc    120
ccgggcaaag gtctcgagtg ggtttccact atcgaatact ctagccagga aacttactat    180
gcggatagcg tgaaaggccg ctttaccatc agccgcgata ttcgaaaaaa caccctgtat    240
ctgcaaatga acagcctgcg tgcggaagat acggccgtgt attattgcgc gcgtgaactg    300
tcttacctgt actctggtta ctacttcgat tactggggcc aaggcaccct ggtgactgtt    360
agctca                                                               366
```

<210> SEQ ID NO 50
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

```
Gln Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Ala
             20                  25                  30

Ala Met Ser Trp Val Arg Gln Ala Pro Gly Lys Gly Leu Glu Trp Val
         35                  40                  45

Ser Thr Ile Glu Tyr Ser Ser Gln Glu Thr Tyr Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Ser Tyr Leu Tyr Ser Gly Tyr Tyr Phe Asp Tyr Trp
             100                 105                 110

Gly Gln Gly Thr Leu Val Thr Val Ser Ser Ala Ser Thr Lys Gly Pro
             115                 120                 125
```

```
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 51
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
caggtgcaat tgctggaaag cggcggtggc ctggtgcagc cgggtggcag cctgcgtctg    60
agctgcgcgg cgtccggatt caccttttct actgctgcta tgtcttgggt gcgccaggcc   120
```

-continued

```
ccgggcaaag gtctcgagtg ggtttccact atcgaatact ctagccagga aacttactat    180
gcggatagcg tgaaaggccg ctttaccatc agccgcgata attcgaaaaa cacccctgtat   240 ctgcaaatga acagcctgcg tgcggaagat acggccgtgt attattgcgc gcgtgaactg    300
tcttacctgt actctggtta ctacttcgat tactggggcc aaggcaccct ggtgactgtt    360
agctcagcct ccaccaaggg tccatcggtc ttccccctgg cacctcctc caagagcacc    420 tctggggca gcggccct gggctgcctg gtcaaggact acttccccga accggtgacg       480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga cagagagtt     660 gagcccaaat cttgtgacaa aactcacaca tgcccaccgt gcccagcacc tgaagcagcg    720
gggggaccgt cagtcttcct cttcccccca aaacccaagg acaccctcat gatctcccgg    780 accctgagg tcacatgcgt ggtggtggac gtgagccacg aagaccctga ggtcaagttc      840
aactggtacg tggacggcgt ggaggtgcat aatgccaaga caaagccgcg ggaggagcag    900
tacaacagca cgtaccgggt ggtcagcgtc ctcaccgtcc tgcaccagga ctggctgaat    960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gaggagatga ccaagaacca ggtcagcctg acctgcctgg tcaaaggctt ctatcccagc    1140
gacatcgccg tggagtggga gagcaatggg cagccggaga acaactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356
```

<210> SEQ ID NO 52
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52

```
caagtgcagc tgcttgaatc tggcggcgga ctggtgcagc ctggcggctc cctgagactg    60
tcttgcgccg cctccggctt caccttctcc accgccgcta tgtcctgggt ccgacaggct   120
cccggcaagg gcctggaatg ggtgtccacc attgagtact ccagccagga aacctactac    180
gccgactccg tgaagggccg gttcaccatc tcccgggaca ctccaagaa cacccctgtac    240 ctgcagatga actccctgcg ggccgaggac accgccgtgt actactgcgc cagagagctg    300
tcctacctgt actccggcta ctacttcgac tactggggcc agggcaccct ggtcaccgtg    360
tcctct                                                              366
```

<210> SEQ ID NO 53
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Thr Ile Glu Tyr Ser Ser Gln Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 54
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54

| | | |
|---|---|---|
| caagtgcagc tgcttgaatc tggcggcgga ctggtgcagc ctggcggctc cctgagactg | 60 |
| tcttgcgccg cctccggctt caccttctcc accgccgcta tgtcctgggt ccgacaggct | 120 |
| cccggcaagg gcctggaatg ggtgtccacc attgagtact ccagccagga aacctactac | 180 |
| gccgactccg tgaagggccg gttcaccatc tcccgggaca actccaagaa cacccctgtac | 240 |
| ctgcagatga actccctgcg ggccgaggac accgccgtgt actactgcgc cagagagctg | 300 |
| tcctacctgt actccggcta ctacttcgac tactggggcc agggcacccct ggtcaccgtg | 360 |
| tcctctgcta gcaccaaggg ccccctccgtg ttccctctgg cccccttccag caagtctacc | 420 |
| tccggcggca cagctgctct gggctgcctg gtcaaggact acttccctga gcctgtgaca | 480 |
| gtgtcctgga actctggcgc cctgacctct ggcgtgcaca ccttccctgc cgtgctgcag | 540 |
| tcctccggcc tgtactccct gtcctccgtg gtcacagtgc cttcaagcag cctgggcacc | 600 |
| cagacctata tctgcaacgt gaaccacaag ccttccaaca ccaaggtgga caagcgggtg | 660 |
| gagcctaagt cctgcgacaa gacccacacc tgtcctccct gccctgctcc tgaagctgct | 720 |
| ggcggcccctt ctgtgttcct gttccctcca agcccaagg acaccctgat gatctcccgg | 780 |
| acccctgaag tgacctgcgt ggtggtggac gtgtcccacg aggatcctga agtgaagttc | 840 |
| aattggtacg tggacggcgt ggaggtgcac aacgccaaga ccaagcctcg ggaggaacag | 900 |
| tacaactcca cctaccgggt ggtgtccgtg ctgaccgtgc tgcaccagga ctggctgaac | 960 |
| ggcaaagagt acaagtgcaa agtctccaac aaggccctgc ctgcccctat cgaaaagaca | 1020 |
| atctccaagg ccaagggcca gcctagggaa ccccaggtgt acaccctgcc acccagccgg | 1080 |
| gaggaaatga ccaagaacca ggtgtccctg acctgtctgg tcaagggctt ctacccttcc | 1140 |
| gatatcgccg tggagtggga gtctaacggc cagcctgaga caactacaa gaccaccccct | 1200 |
| cctgtgctgg actccgacgg ctccttcttc ctgtactcca aactgaccgt ggacaagtcc | 1260 |
| cggtggcagc agggcaacgt gttctcctgc tccgtgatgc acgaggccct gcacaaccac | 1320 |
| tacacccaga gtccctgtc cctgtctccc ggcaag | 1356 |

<210> SEQ ID NO 55
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
                20                  25                  30

Asp Val Ser Trp Tyr Gln Gln Leu Pro Gly Thr Ala Pro Lys Leu Leu
            35                  40                  45

Ile Tyr Lys Asn Tyr Asn Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110

<210> SEQ ID NO 56
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
cagagcgtgc tgacacagcc tccctccgtg tctggcgccc ctggccagag agtgaccatc      60
tcctgctccg gctcctcctc aacatcggc tccaacgacg tgtcctggta tcagcagctg     120
cccggcaccg cccctaagct gctgatctac aagaactaca accggccctc cggcgtgccc     180
gaccggttct ctggctccaa gtctggcacc tccgcctccc tggctatcac cggcctgcag     240
gctgaggacg aggccgacta ctactgctcc gcctgggacc agcggcagtt cgacgtggtg     300
ttcggcggag gcaccaagct gaccgtgctg                                     330

<210> SEQ ID NO 57
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Ser Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
                20                  25                  30

Asp Val Ser Trp Tyr Gln Gln Leu Pro Gly Thr Ala Pro Lys Leu Leu
            35                  40                  45

Ile Tyr Lys Asn Tyr Asn Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

```
Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 58
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
cagagcgtgc tgacacagcc tccctccgtg tctggcgccc tggccagag agtgaccatc      60 tcctgctccg gctcctcctc aacatcggc tccaacgacg tgtcctggta tcagcagctg     120
cccggcaccg cccctaagct gctgatctac aagaactaca accggccctc cggcgtgccc     180
gaccggttct ctggctccaa gtctggcacc tccgcctccc tggctatcac cggcctgcag     240
gctgaggacg aggccgacta ctactgctcc gcctgggacc agcggcagtt cgacgtggtg     300
ttcggcggag gcaccaagct gaccgtgctg ggcagccta aggctgcccc cagcgtgacc     360
ctgttccccc ccagcagcga ggagctgcag gccaacaagg ccaccctggt gtgcctgatc     420
agcgacttct acccaggcgc cgtgaccgtg gcctggaagg ccgacagcag ccccgtgaag     480
gccggcgtgg agaccaccac ccccagcaag cagagcaaca acaagtacgc cgccagcagc     540
tacctgagcc tgaccccga gcagtggaag agccacaggt cctacagctg ccaggtgacc     600
cacgagggca gcaccgtgga aaagaccgtg gccccaaccg agtgcagc                 648

<210> SEQ ID NO 59
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: source
<223> OTHER INFORMATION: /note="See specification as filed for detailed
``` description of substitutions and preferred embodiments"

<400> SEQUENCE: 59

Xaa Ile Xaa Xaa Xaa Xaa Xaa Xaa Thr Xaa Tyr Ala Asp Ser Val Lys
1               5                   10                  15

Gly

<210> SEQ ID NO 60
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(6)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 60

Xaa Xaa Xaa Xaa Xaa Xaa
1               5

<210> SEQ ID NO 61
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(7)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 61

Ile Xaa Xaa Xaa Xaa Xaa Xaa Thr
1               5

<210> SEQ ID NO 62
<211> LENGTH: 452
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Ala
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Leu Ser Tyr Leu Tyr Ser Gly Tyr Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 63
<211> LENGTH: 1356
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
caggtgcaat tgctggaaag cggcggtggc ctggtgcagc cgggtggcag cctgcgtctg      60
agctgcgcgg cgtccggatt cacctttct actgctgcta tgtcttgggt gcgccaggcc     120
ccgggcaaag gtctcgagtg gtttccggt atctctggtt ctggttcttc tacctactat     180
gcggatagcg tgaaaggccg ctttaccatc agccgcgata attcgaaaaa cacccctgtat   240
ctgcaaatga acagcctgcg tgcggaagat acggccgtgt attattgcgc gcgtgaactg    300
tcttacctgt actctggtta ctacttcgat tactggggcc aaggcaccct ggtgactgtt    360
agctcagcct ccaccaaggg tccatcggtc ttccccctgg caccctcctc caagagcacc   420
tctgggggca gcgcgccct gggctgcctg gtcaaggact acttccccga accggtgacg    480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacc   600
cagacctaca tctgcaacgt gaatcacaag cccagcaaca ccaaggtgga caagagagtt    660
gagcccaaat cttgtgacaa aactcacaca tgcccaccgt gcccagcacc tgaagcagcg   720
gggggaccgt cagtcttcct cttccccca aacccaagg acaccctcat gatctcccgg     780
accctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgggt ggtcagcgtc ctcaccgtcc tgcaccagga ctggctgaat    960
ggcaaggagt acaagtgcaa ggtctccaac aaagcccctcc cagcccccat cgagaaaacc  1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga caactacaa gaccacgcct    1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaa                             1356
```

<210> SEQ ID NO 64
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln

```
                   65                  70                  75                  80
Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu
            100                 105                 110
```

<210> SEQ ID NO 65
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

```
gatatcgtgc tgacccagcc gccgagcgtg agcggtgcac cgggccagcg cgtgaccatt      60
agctgtagcg gcagcagcag caacattggt tctaacgacg tgtcttggta ccagcagctg     120
ccgggcacgg cgccgaaact gctgatctac aaaaactaca accgcccgag cggcgtgccg     180
gatcgcttta gcggatccaa aagcggcacc agcgccagcc tggcgattac cggcctgcaa     240
gcagaagacg aagcggatta ttactgctct gcttgggacc agcgtcagtt cgacgttgtg     300
tttggcggcg gcacgaagtt aaccgtccta                                      330
```

<210> SEQ ID NO 66
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Asp Val Ser Trp Tyr Gln Gln Leu Pro Gly Thr Ala Pro Lys Leu Leu
        35                  40                  45

Ile Tyr Lys Asn Tyr Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ala Trp Asp Gln Arg Gln
                85                  90                  95

Phe Asp Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

```
Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 67
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
gatatcgtgc tgacccagcc gccgagcgtg agcggtgcac cgggccagcg cgtgaccatt      60
agctgtagcg gcagcagcag caacattggt tctaacgacg tgtcttggta ccagcagctg     120
ccgggcacgg cgccgaaact gctgatctac aaaaactaca accgcccgag cggcgtgccg     180
gatcgcttta gcggatccaa aagcggcacc agcgccagcc tggcgattac cggcctgcaa     240
gcagaagacg aagcggatta ttactgctct gcttgggacc agcgtcagtt cgacgttgtg     300
tttggcggcg gcacgaagtt aaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540 tatctgagcc tgacgcctga cagtggaag tcccacagaa gctacagctg ccaggtcacg     600
catgaaggga gcaccgtgga agacagtg gcccctacag aatgttca                    648

<210> SEQ ID NO 68
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 68

His His His His His His
1               5

<210> SEQ ID NO 69
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
caggtgcaat tgctggaaag cggcggtggc ctggtgcagc cgggtggcag cctgcgtctg      60
agctgcgcgg cgtccggatt cacctttct actgctgcta tgtcttggt gcgccaggcc     120 ccgggcaaag gtctcgagtg gtttccggt atctctggtt ctggttcttc tacctactat     180
gcggatagcg tgaaaggccg ctttaccatc agccgcgata attcgaaaaa caccctgtat     240
```

```
ctgcaaatga acagcctgcg tgcggaagat acggccgtgt attattgcgc gcgtgaactg    300
tcttacctgt actctggtta ctacttcgat tactggggcc aaggcaccct ggtgactgtt    360
agctca                                                                366
```